(12) United States Patent
Guichard et al.

(10) Patent No.: US 8,357,654 B2
(45) Date of Patent: *Jan. 22, 2013

(54) MULTIMERIC CD40 LIGANDS, METHOD FOR PREPARING SAME AND USE THEREOF FOR PREPARING DRUGS

(75) Inventors: Gilles Guichard, Wolfisheim (FR); Sylvie Victorine Lucienne Fournel, Strasbourg (FR); Olivier Chaloin, Strasbourg (FR); Nathalie Trouche, Erstein-Krafft (FR); Sêbastien Wieckowski, Ambilly (FR); Johan Hoebeke, Kessel-Lo (BE)

(73) Assignee: Centre National de la Recherche Scientifique, Paris (FR)

( * ) Notice: Subject to any disclaimer, the term of this patent is extended or adjusted under 35 U.S.C. 154(b) by 936 days.

This patent is subject to a terminal disclaimer.

(21) Appl. No.: 11/721,910

(22) PCT Filed: Dec. 15, 2005

(86) PCT No.: PCT/FR2005/003146
§ 371 (c)(1),
(2), (4) Date: Jan. 30, 2009

(87) PCT Pub. No.: WO2006/064133
PCT Pub. Date: Jun. 22, 2006

(65) Prior Publication Data
US 2010/0183642 A1 Jul. 22, 2010

(30) Foreign Application Priority Data
Dec. 15, 2004 (FR) ........................ 04 13331

(51) Int. Cl.
*A61K 38/12* (2006.01)
*C07K 7/64* (2006.01)
(52) U.S. Cl. ......... 514/3.9; 514/21.8; 530/317; 530/321
(58) Field of Classification Search ........................ None
See application file for complete search history.

(56) References Cited

U.S. PATENT DOCUMENTS

| 2003/0053984 A1 | 3/2003 | Tschopp et al. |
| 2004/0047873 A1 | 3/2004 | Al-Shamkhani et al. |
| 2006/0035839 A1 | 2/2006 | Guichard et al. |

FOREIGN PATENT DOCUMENTS

| WO | 9952877 | 10/1999 |
| WO | 0149866 | 7/2001 |
| WO | 0200893 | 1/2002 |
| WO | 03102207 | 12/2003 |

OTHER PUBLICATIONS

CDC "Vaccine Development and Testing" from www.hhs.gov/nvpo/factsheets/fs_tablell-doc1.htm, pp. 1-4. Accessed Feb. 12, 2009.*
Seminars in Immunology., vol. 6, 1994, pp. 295-301, XP002237774 US W.B. Sauners Company, PA.
L K Kiessling et al.: "Synthetic multivalent ligands in the exploration of cell-surface interactions" Current Opinion in Chemical Biology, vol. 4, 2000, pp. 696-703, XP002382114 GB Current Biology LTD, London.
S Fournel et al.: "C3-symmetric peptides scaffolds are functional mimetics of trimeric CD40L" Nature Chemical Biology, vol. 1, No. 7, (Dec. 2005), pp. 377-382, XP002382115 US Nature Publishing Group, New York, NY.

* cited by examiner

*Primary Examiner* — Julie Ha
(74) *Attorney, Agent, or Firm* — Young & Thompson

(57) ABSTRACT

A compound of formula (I) is described, wherein Y represents a macrocycle, the ring of which has 9 to 36 atoms, and is functionalized by three amine or COOH functions; $R_c$ represents a group of formula $H-X_a-X_b-X_c-X_d-X_e-(X_f)_i-$, i represents 0 or 1, $X_a$ is in particular lysine, arginine, or ornithine residues, $X_b$ is in particular glycine, asparagine, L-proline or D-proline residues, $X_c$ and $X_d$ are in particular tyrosine, phenylalanine or 3-nitrotyrosine residues, $X_e$ and $X_f$ are in particular amino acid residues: $NH_2-(CH_2)_n-COOH$, n ranging from 1 to 10, or $NH_2-(CH_2-CH_2-O)_m-CH_2CH_2COOH$, m ranging from 3 to 6, provided that at least one of the amino acid residues $X_a$, $X_b$, $X_c$ and $X_d$ is different from the corresponding amino acid in the sequence of the natural CD40 $^{143}$Lys-Gly-Tyr-Tyr$^{146}$ fragment(SEQ ID NO: 1).

13 Claims, 6 Drawing Sheets

```
                        SEQUENCE LISTING

<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Lys Gly Tyr Tyr
1

<210> SEQ ID NO 2
<211> LENGTH: 5
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (5)..(5)
<223> OTHER INFORMATION: Xaa = Acp

<400> SEQUENCE: 2

Lys Xaa Tyr Tyr Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = Acp
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (5)..(5)
<223> OTHER INFORMATION: Xaa = Acp

<400> SEQUENCE: 3

Xaa Xaa Tyr Tyr Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (5)..(5)
<223> OTHER INFORMATION: Xaa = Acp

<400> SEQUENCE: 4

Lys Xaa Tyr Tyr Xaa
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Xaa = Acp

<400> SEQUENCE: 5

Lys Gly Tyr Xaa
1

<210> SEQ ID NO 6
```

```
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = (D)Pro

<400> SEQUENCE: 6

Lys Xaa Tyr Tyr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = Acp
<220> FEATURE:
<221> NAME/KEY: MISC_FEATURE
<222> LOCATION: (2)..(2)
<223> OTHER INFORMATION: Xaa = (D) Pro

<400> SEQUENCE: 7

Xaa Xaa Tyr Tyr
1

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: BLOCKED, Xaa = Acp
      Acp is protected by tert-Butyloxycarbonyl
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (3)..(3)
<223> OTHER INFORMATION: BLOCKED Tyr is protected by tert-Butyl
<220> FEATURE:
<221> NAME/KEY: MOD_RES
<222> LOCATION: (4)..(4)
<223> OTHER INFORMATION: BLOCKED Tyr is protected by tert-Butyl
<220> FEATURE:
<221> NAME/KEY: MOD_RES
<222> LOCATION: (5)..(5)
<223> OTHER INFORMATION: Xaa = Acp

<400> SEQUENCE: 8

Xaa Xaa Tyr Tyr Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: BLOCKED Lys amino groups are protected by tert-
      Butyloxycarbonyl
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (3)..(3)
<223> OTHER INFORMATION: BLOCKED Tyr is protected by tert-Butyl
<220> FEATURE:
<221> NAME/KEY: MOD_RES
<222> LOCATION: (4)..(4)
<223> OTHER INFORMATION: BLOCKED Tyr is protected by tert-Butyl
<220> FEATURE:
<221> NAME/KEY: MOD_RES
<222> LOCATION: (5)..(5)
<223> OTHER INFORMATION: Xaa = Acp

<400> SEQUENCE: 9

Lys Xaa Tyr Tyr Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Sythetic peptide
<220> FEATURE:
<221> NAME/KEY: MOD_RES
<222> LOCATION: (5)..(5)
<223> OTHER INFORMATION: Xaa = Acp

<400> SEQUENCE: 10

Lys Pro Tyr Tyr Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = (L) (Boc)NHCH((CH2)4NH(Boc))CH2
      Boc is tert-Butyloxycarbonyl
<220> FEATURE:
<221> NAME/KEY: MISC_FEATURE
<222> LOCATION: (2)..(2)
<223> OTHER INFORMATION: Xaa = (D)Pro
<220> FEATURE:
<221> NAME/KEY: MOD_RES
<222> LOCATION: (3)..(3)
<223> OTHER INFORMATION: BLOCKED Tyr is protected by tert-Butyl
<220> FEATURE:
<221> NAME/KEY: MOD_RES
<222> LOCATION: (4)..(4)
<223> OTHER INFORMATION: BLOCKED Tyr is protected by tert-Butyl
<220> FEATURE:
<221> NAME/KEY: MOD_RES
<222> LOCATION: (5)..(5)
<223> OTHER INFORMATION: Xaa = Acp

<400> SEQUENCE: 11

Xaa Xaa Tyr Tyr Xaa
1               5

<210> SEQ ID NO 12
<211> LENGTH: 5
<212> TYPE: PRT
<213> ORGANISM: Artificial Sequence
```

-continued

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: BLOCKED Lys amino groups are protected by tert-
      Butyloxycarbonyl
<220> FEATURE:
<221> NAME/KEY: MISC_FEATURE
<222> LOCATION: (3)..(3)
<223> OTHER INFORMATION: Xaa = DOPA
      DOPA hydroxyl groups are protected by acetonid
<220> FEATURE:
<221> NAME/KEY: MOD_RES
<222> LOCATION: (4)..(4)
<223> OTHER INFORMATION: BLOCKED Tyr is protected by tert-Butyl
<220> FEATURE:
<221> NAME/KEY: MOD_RES
<222> LOCATION: (5)..(5)
<223> OTHER INFORMATION: Xaa = Acp

<400> SEQUENCE: 12

Lys Gly Xaa Tyr Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: BLOCKED Lys amino groups are protected by tert-
      Butyloxycarbonyl
<220> FEATURE:
<221> NAME/KEY: MOD_RES
<222> LOCATION: (3)..(3)
<223> OTHER INFORMATION: BLOCKED Tyr is protected by tert-Butyl
<220> FEATURE:
<221> NAME/KEY: MOD_RES
<222> LOCATION: (4)..(4)
<223> OTHER INFORMATION: BLOCKED Tyr is protected by tert-Butyl
<220> FEATURE:
<221> NAME/KEY: MOD_RES
<222> LOCATION: (5)..(5)
<223> OTHER INFORMATION: Xaa = Acp

<400> SEQUENCE: 13

Lys Gly Tyr Tyr Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = (D) Ala
<220> FEATURE:
<221> NAME/KEY: MOD_RES
<222> LOCATION: (2)..(2)
<223> OTHER INFORMATION: BLOCKED Lys is protected by tert-
      Butyloxycarbonyl
<220> FEATURE:
<221> NAME/KEY: MISC_FEATURE
<222> LOCATION: (3)..(3)
<223> OTHER INFORMATION: Xaa = (D) Lys (Biot)
      Biot is a biotinyl group
<220> FEATURE:
<221> NAME/KEY: MOD_RES
<222> LOCATION: (4)..(4)
```

```
<223>  OTHER INFORMATION: BLOCKED Lys is protected by tert-
       Butyloxycarbonyl
<220>  FEATURE:
<221>  NAME/KEY: MISC_FEATURE
<222>  LOCATION: (5)..(5)
<223>  OTHER INFORMATION: Xaa = (D) Ala
<220>  FEATURE:
<221>  NAME/KEY: MOD_RES
<222>  LOCATION: (6)..(6)
<223>  OTHER INFORMATION: BLOCKED Lys is protected by tert-
       Butyloxycarbonyl

<400>  SEQUENCE: 14

Xaa Lys Xaa Lys Xaa Lys
1               5
```

MULTIMERIC CD40 LIGANDS, METHOD FOR PREPARING SAME AND USE THEREOF FOR PREPARING DRUGS

A subject of the present invention is novel multimeric CD40 ligands, their preparation process, as well as their use for the preparation of medicaments.

A subject of the invention is also molecules capable of activating or inhibiting the immune response.

The importance of the CD40/CD40L pair in the immune response has led numerous groups to use antibodies directed against these two molecules for therapeutic purposes, in order to inhibit or activate the immune system. The administration of anti-CD40L antibodies has produced encouraging results in the treatment of auto-immune diseases such as murine experimental allergic encephalomyelitis (a model of human multiple sclerosis) (Howard et al., 1999) or in the treatment of renal allograft rejection in monkeys (Kirk et al., 1999). In these two cases, the antibodies have inhibited a harmful activity of the immune system. Conversely, the use of agonist anti-CD40 antibodies has made it possible on the one hand to strongly improve the response to peptide-based anti-tumor vaccines in mice (Diehl et al., 1999) and on the other hand, to increase the effectiveness of CD4$^+$ T cells in the fight against murine tumors (Sotomayor et al., 1999; Lode et al., 2000). A tumor regression in murine models was demonstrated after injection of dendritic cells (DCs) transformed by an adenovirus encoding the CD40L (Kikuchi et al., 2000). Finally, an activation of the dendritic cells by the interaction of their CD40 molecule with CD40L is capable of protecting mice from an infection by a parasite, *Trypanosoma Cruzi* (Chaussabel et al., 1999). In all these works, the particular valency of the CD40L molecule, which is combined in trimer form in order to form hexavalent complexes with the CD40, makes it difficult to produce functional antibodies capable of interfering with the functions of the CD40/CD40L pair. The development of the adenovirus coding for CD40L responds in part to this drawback. However, their use is not without problems in humans. Finally, the particular valency of the system makes it difficult to discover synthesis molecules capable of interfering with the CD40/CD40L interaction.

The purpose of the invention is to provide multimeric ligands designed to interfere in protein-protein interactions.

The purpose of the present invention is also the preparation of molecules which can interfere with multivalent protein-protein interactions.

The purpose of the present invention is to provide a synthesis molecule acting on the CD40/CD40L system, by providing novel trimeric CD40 ligands.

The purpose of the present invention is also to provide molecules which can act as adjuvants or immunosuppressants.

The present invention relates to compounds corresponding to the following formula (I):

$$R_c\diagdown Y \diagup R_c \atop | \atop R_c \qquad (I)$$

in which:
Y represents a macrocycle the ring of which comprises 9 to 36 atoms, and is functionalized by three amine or COOH functions, $R_c$, represents a group of formula H—$X_a$—$X_b$—$X_c$—$X_d$—$X_e$—$(X_f)_i$— or H—$X'_a$-L-$X'_b$—$X_c$—$X_d$—$X_e$—$(X_f)_i$—, in which:

i represents 0 or 1, $X_a$ is chosen from the following amino acid residues:
 lysine;
 arginine;
 ornithine;
 the β-amino acids corresponding to lysine, arginine or ornithine, carrying the substitution in α or β position;
 tranexamic acid;
 N-methyl-tranexamic acid;
 8-amino-3,6-dioxaoctanoic acid;
 4(piperidin-4-yl)butanoic acid;
 3(piperidin-4-yl)propionic acid;
 N-(4-aminobutyl)-glycine;
 $NH_2$—$(CH_2)_n$—COOH, n varying from 1 to 10;
 $NH_2$—$(CH_2$—$CH_2$—$O)_m$—$CH_2CH_2COOH$, m varying from 3 to 6;
 4-carboxymethyl-piperazine;
 4-(4-aminophenyl)butanoic acid;
 3-(4-aminophenyl)propanoic acid;
 4-aminophenylacetic acid;
 4-(2-aminoethyl)-1-carboxymethyl-piperazine;
 trans-4-aminocyclohexanecarboxylic acid;
 cis-4-aminocyclohexanecarboxylic acid;
 cis-4-aminocyclohexane acetic acid;
 trans-4-aminocyclohexane acetic acid;
 4-amino-1-carboxymethyl piperidine;
 4-aminobenzoic acid;
 4(2-aminoethoxy)benzoic acid;

$X_b$ is chosen from the following amino acid residues:
 glycine;
 asparagine;
 D-alanine;
 D-valine;
 L-proline substituted or non-substituted in β, γ or δ position;
 D-proline substituted or non-substituted in β, γ or δ position;
 N-alkylated natural amino acids, the alkyl group being a methyl, ethyl or benzyl group;
 acyclic dialkylated amino acids of the following formula:

$$\text{(A)} \quad H_2N-\underset{\underset{R}{|}}{\overset{\overset{R}{|}}{C}}-C(O)OH$$

R representing H, Me, Et, Pr or Bu;
cyclic dialkylated amino acids of the following formula:

$$\text{(B)} \quad H_2N-\underset{}{\overset{(CH_2)_k}{\triangle}}-C(O)OH$$

k representing 1, 2, 3 or 4;

$X_c$ is chosen from the following amino acid residues:
- tyrosine;
- phenylalanine;
- 3-nitro-tyrosine;
- 4-hydroxymethyl-phenylalanine;
- 3,5-dihydroxy-phenylalanine;
- 2,6-dimethyl-tyrosine;
- 3,4-dihydroxy-phenylalanine (DOPA);

$X_d$ is chosen from the following amino acid residues:
- tyrosine;
- phenylalanine;
- 3-nitro-tyrosine;
- 4-hydroxymethyl-phenylalanine;
- 3,5-dihydroxy-phenylalanine;
- 2,6-dimethyl-tyrosine;
- 3,4-dihydroxy-phenylalanine;

$X_e$ is chosen from the following amino acid residues:
- $NH_2$—$(CH_2)_n$—COOH, n varying from 1 to 10;
- $NH_2$—$(CH_2$—$CH_2$—$O)_m$—$CH_2CH_2COOH$, m varying from 3 to 6;
- 8-amino-3,6-dioxaoctanoic acid;
- tranexamic acid;
- N-methyl-tranexamic acid;
- 4(piperidin-4-yl)butanoic acid;
- 3(piperidin-4-yl)propionic acid;
- N-(4-aminobutyl)-glycine;
- 4-carboxymethyl-piperazine;
- 4-(4-aminophenyl)butanoic acid;
- 3-(4-aminophenyl)propanoic acid;
- 4-aminophenylacetic acid;
- 4-(2aminoethyl)-1-carboxymethyl-piperazine;
- trans-4-aminocyclohexanecarboxylic acid;
- cis-4-aminocyclohexanecarboxylic acid;
- cis-4-aminocyclohexane acetic acid;
- trans-4-aminocyclohexane acetic acid;
- 4-amino-1-carboxymethyl piperidine;
- 4-aminobenzoic acid;
- 4(2-aminoethoxy)benzoic acid;

$X_f$ is chosen from the following amino acid residues:
- $NH_2$—$(CH_2)_n$—COOH, n varying from 1 to 10;
- $NH_2$—$(CH_2$—$CH_2$—$O)_m$—$CH_2CH_2COOH$, m varying from 3 to 6;
- 8-amino-3,6-dioxaoctanoic acid;
- tranexamic acid;
- N-methyl-tranexamic acid;
- 4(piperidin-4-yl)butanoic acid;
- 3(piperidin-4-yl)propionic acid;
- N-(4-aminobutyl)-glycine;
- 4-carboxymethyl-piperazine;
- 4-(4-aminophenyl)butanoic acid;
- 3-(4-aminophenyl)propanoic acid;
- 4-aminophenylacetic acid;
- 4-(2aminoethyl)-1-carboxymethyl-piperazine;
- trans-4-aminocyclohexanecarboxylic acid;
- cis-4-aminocyclohexanecarboxylic acid;
- cis-4-aminocyclohexane acetic acid;
- trans-4-aminocyclohexane acetic acid;
- 4-amino-1-carboxymethyl piperidine;
- 4-aminobenzoic acid;
- 4(2-aminoethoxy)benzoic acid;

-L- represents a pseudopeptide-type bond between the $X'_a$ and $X'_b$ residues, chosen in particular from the list below:

-L-=-ψ($CH_2CH_2$)—; -ψ(CH($F_k$)=CH($F_k'$))-; -ψ($CH_2$NH)—; -ψ(NHCO)—; -ψ(NHCONH)—; -ψ(CO—O)—; -ψ(CS—NH)—; -ψ(CH(OH)—CH(OH))—; -ψ(S—$CH_2$)—; -ψ($CH_2$—S)—; -ψ(CH(CN)—$CH_2$)—; -ψ(CH(OH))—; -ψ(COCH$_2$)—; -ψ(CH(OH)CH$_2$)—; -ψ(CH(OH)CH$_2$NH)—; -ψ(CH$_2$)—; -ψ(CH($F_k$))—; -ψ(CH$_2$O)—; -ψ(CH$_2$—NHCONH)—; -ψ(CH($F_k$)NHCONF$_k'$)—; -ψ(CH$_2$—CONH)—; -ψ(CH($F_k$)CONH)—; -ψ(CH($F_k$)CH($F_k'$)CONH)—;

or -ψ(CH$_2$N)—; -ψ(NHCON)—; -ψ(CS—N)—; -ψ(CH(OH)CH$_2$N)—; -ψ(CH$_2$—NHCON)—; -ψ(CH$_2$—CON)—; -ψ(CH($F_k$)CON)—; -ψ(CH($F_k$)CH($F_k'$)CON)— when $X'_b$ represents the side chain of a proline, these pseudopeptide bonds being in particular described in the article of Spatola (1983), $F_k$ and $F_k'$ representing, independently of one another, a hydrogen, a halogen, an alkyl group of 1 to 20 carbon atoms, or an aryl group the ring structure of which contains from 5 to 20 carbon atoms, $X'_a$ represents the side chain of lysine, arginine or ornithine; and $X'_b$ represents the side chain of one of the following amino acid residues:
- glycine;
- asparagine;
- D-alanine;
- D-valine;
- L-proline substituted or non-substituted in β, γ or δ position;
- D-proline substituted or non-substituted in β, γ or δ position;
- N-alkylated natural amino acids, the alkyl group being a methyl, ethyl or benzyl group;
- acyclic dialkylated amino acids of the following formula:

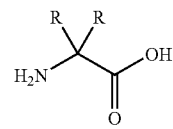

(A)

R representing H, Me, Et, Pr or Bu;
cyclic dialkylated amino acids of the following formula:

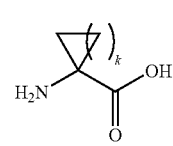

(B)

k representing 1, 2, 3 or 4;
providing that at least one of the amino acid residues $X_a$, $X_b$, $X_c$ and $X_d$ is different from the corresponding amino acid in the sequence of the [143]Lys-Gly-Tyr-Tyr[146] (SEQ ID NO: 1) fragment of natural CD40L.

Thus, the H—$X'_a$-L-$X'_b$— group can for example be represented by one of the following formulae:

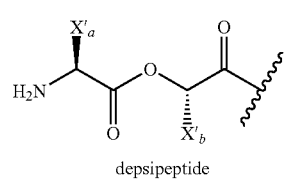

depsipeptide

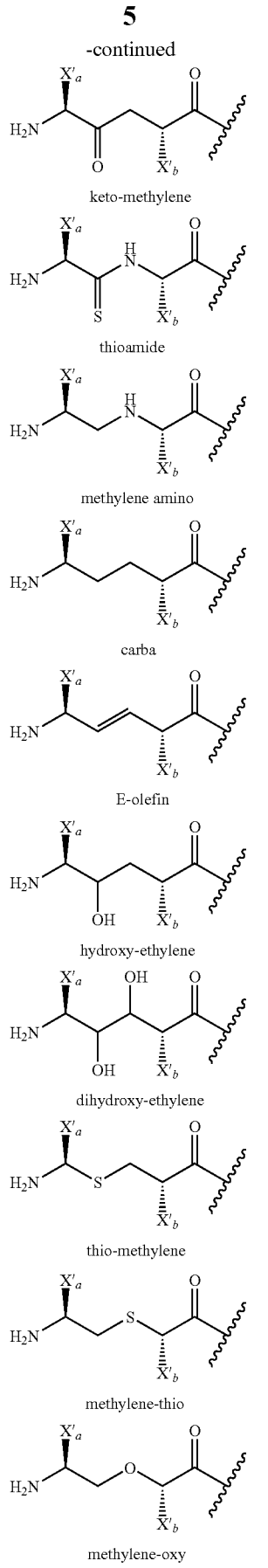
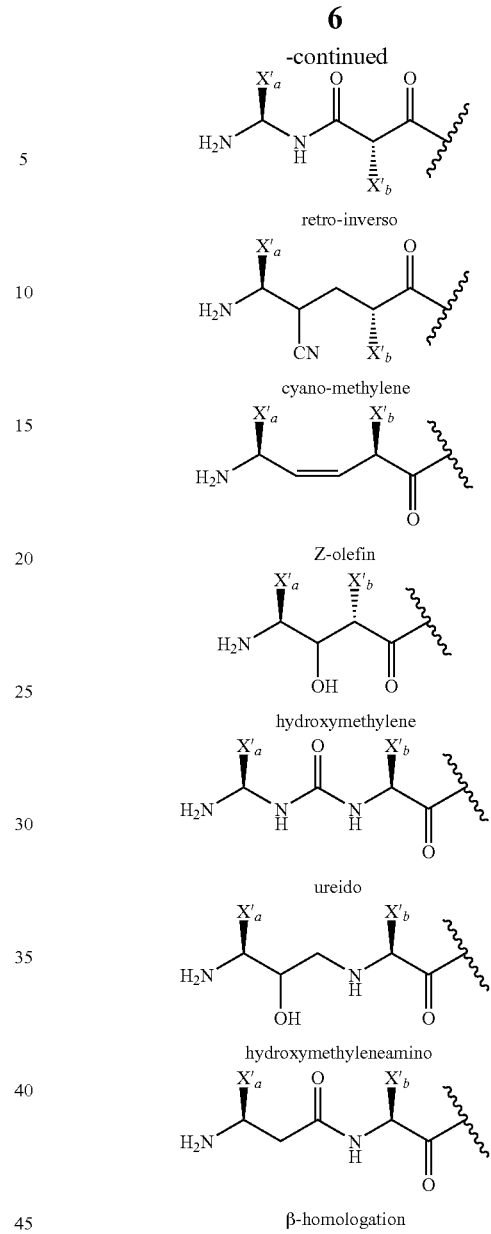

The compounds of the invention correspond to formula (I) as defined above in which the $X_a$—$X_b$—$X_c$—$X_d$ chaining is different from the Lys-Gly-Tyr-Tyr (SEQ ID NO: 1) chaining.

When the Y group is functionalized by three COOH functions, Y is bound to $R_c$ by a —CO— group, and when Y is functionalized by three amine functions, Y is bound to $R_c$ by an —NH— group.

The compounds of the invention can also be represented by the following formula:

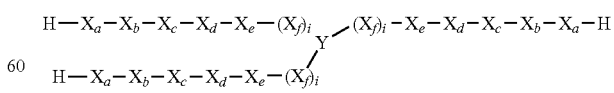

Y, $X_a$, $X_b$, $X_c$, $X_d$, $X_e$, $X_f$ and i being as defined above.

The $X_e$—$(X_f)_i$— group serves as an arm for binding H—$X_a$—$X_b$—$X_c$—$X_d$— to Y.

The compounds of the invention are compounds with $C_3$ symmetry and correspond to novel trimeric CD40 ligands.

Within the framework of the present invention, the expression "amino acids" designates in particular natural or non-natural amino acids, in particular alpha-, beta-, gamma-, delta-amino acids, or ω-amino acids.

The term "macrocycle" designates a ring comprising nitrogen, carbon or oxygen atoms, the total number of atoms of which is greater than or equal to 9.

The expression "β-amino acids corresponding to lysine, arginine or ornithine, carrying the substitution in α or β" position designates compounds corresponding to one of the following formulae: $H_2N-CH_2-CH(R_b)-COOH$ (α position) or $H_2N-CH(R_b)-CH_2COOH$ (β position), $R_b$ corresponding to lysine, arginine or ornithine residue.

More precisely, $X_a$ is chosen from the following groups:

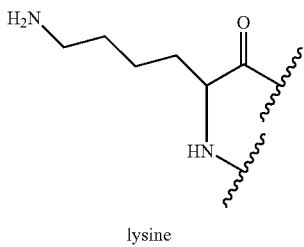

lysine

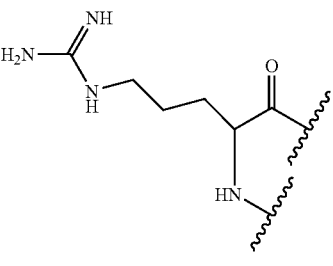

arginine

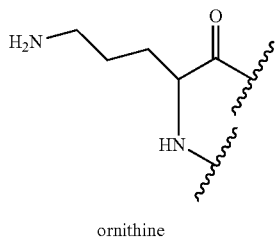

ornithine

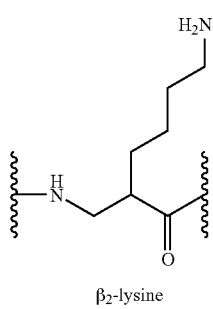

β2-lysine

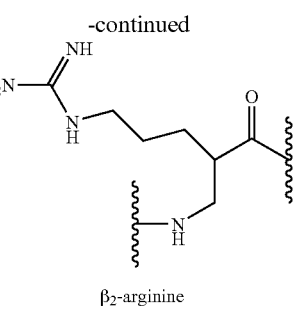

β2-arginine

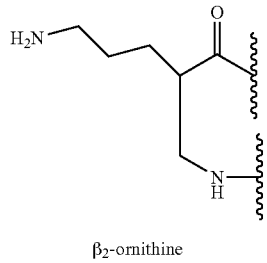

β2-ornithine

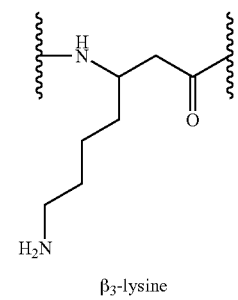

β3-lysine

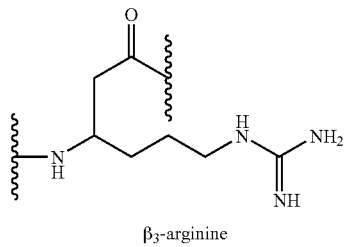

β3-arginine

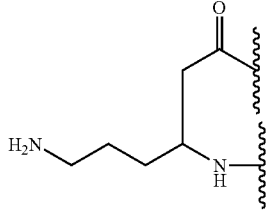

β3-ornithine

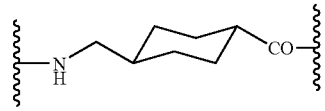

tranexamic acid

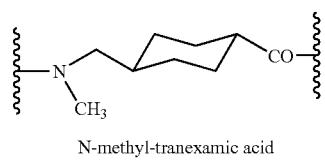

N-methyl-tranexamic acid

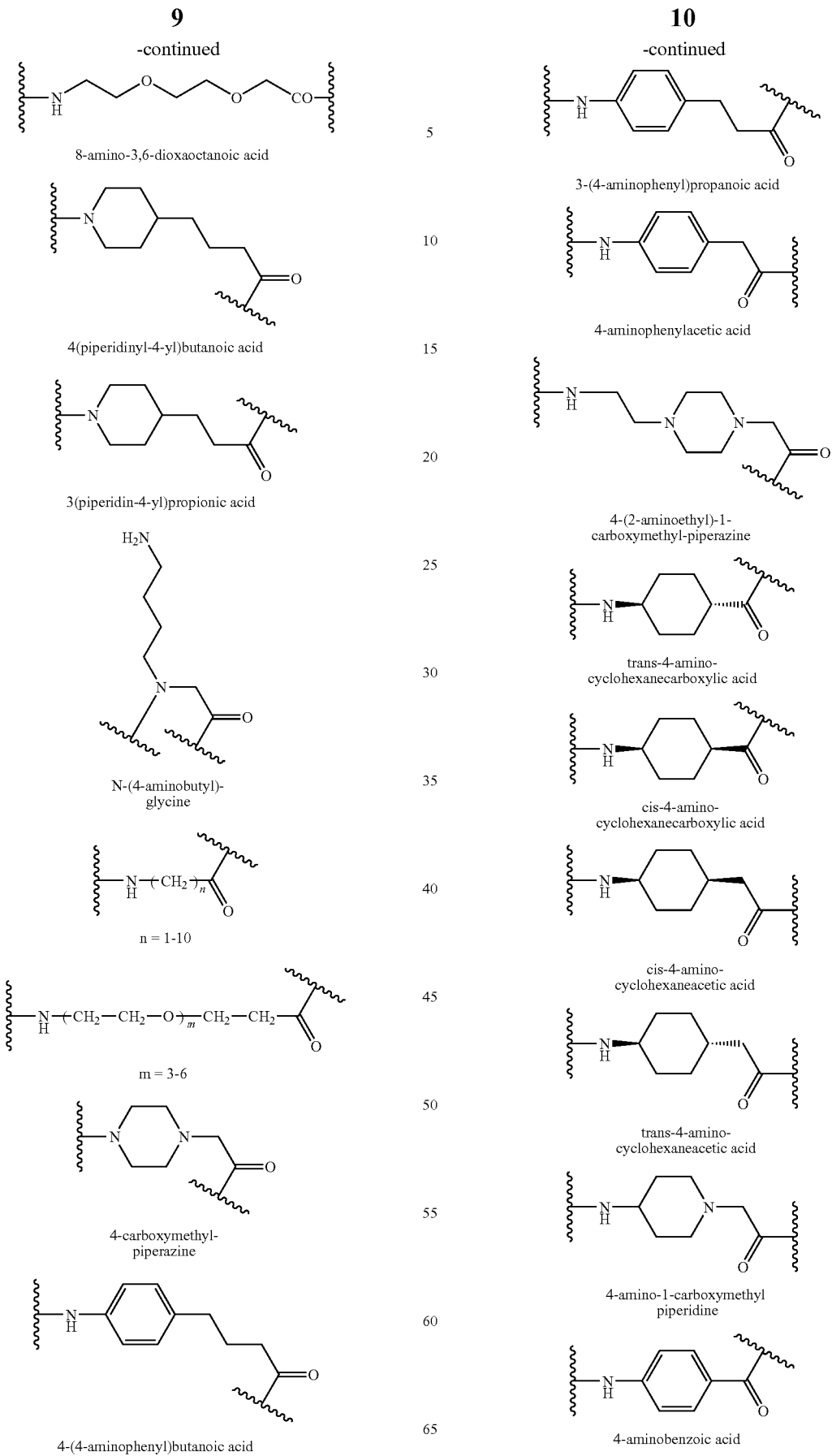

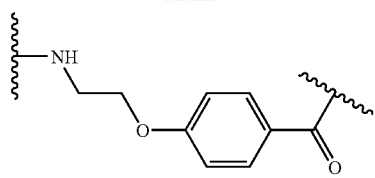

4(2-aminoethoxy)benzoic acid $X_b$ is chosen from the following groups:

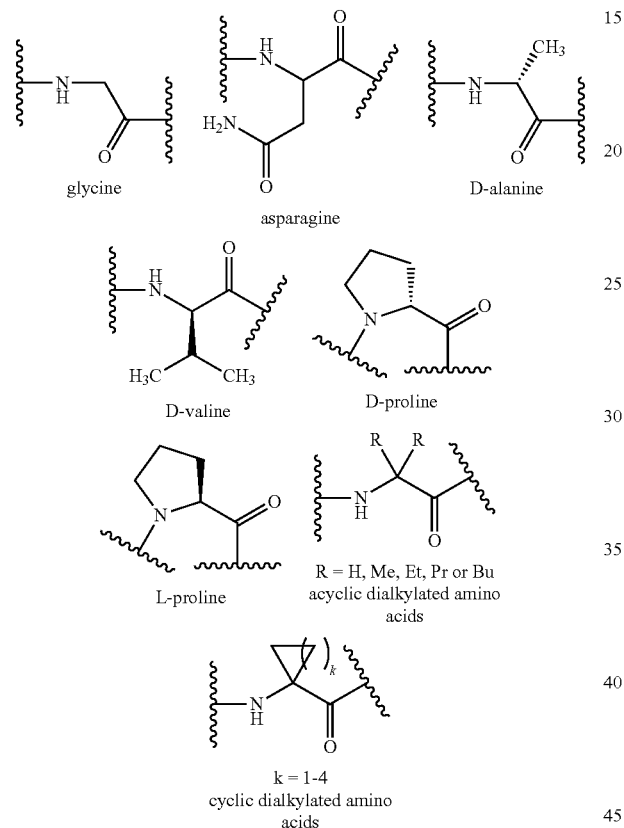

glycine  
asparagine  
D-alanine  
D-valine  
D-proline  
L-proline  
R = H, Me, Et, Pr or Bu  
acyclic dialkylated amino acids  
k = 1-4  
cyclic dialkylated amino acids $X_c$ and $X_d$ are chosen from the following groups:

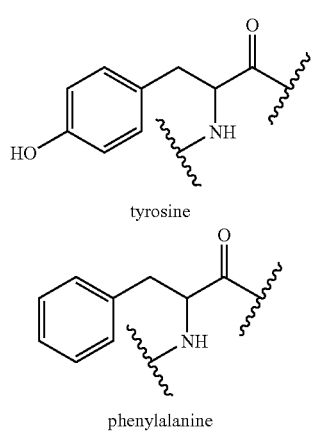

tyrosine phenylalanine

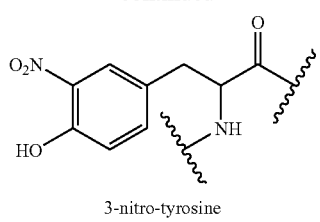

3-nitro-tyrosine

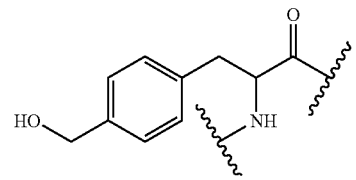

4-hydroxymethyl-phenylalanine

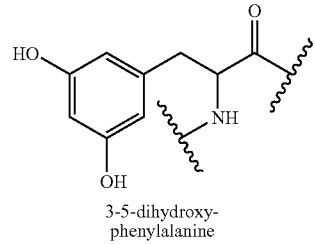

3-5-dihydroxy-phenylalanine

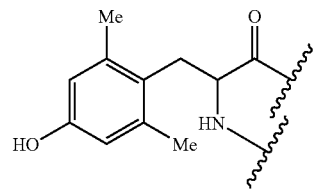

2,6-dimethyl-tyrosine

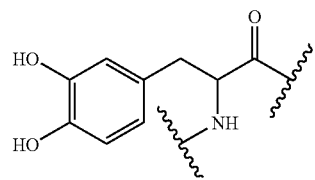

3,4-dihydroxy-phenylalanine (or L-DOPA)

$X_e$ and $X_f$ are chosen from the following groups:

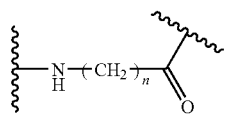

n = 1-10

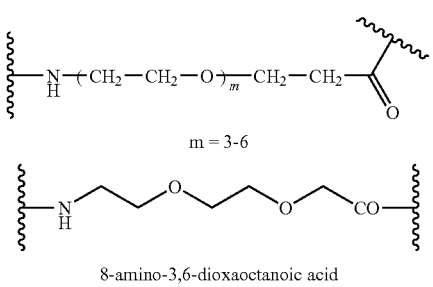

m = 3-6

8-amino-3,6-dioxaoctanoic acid

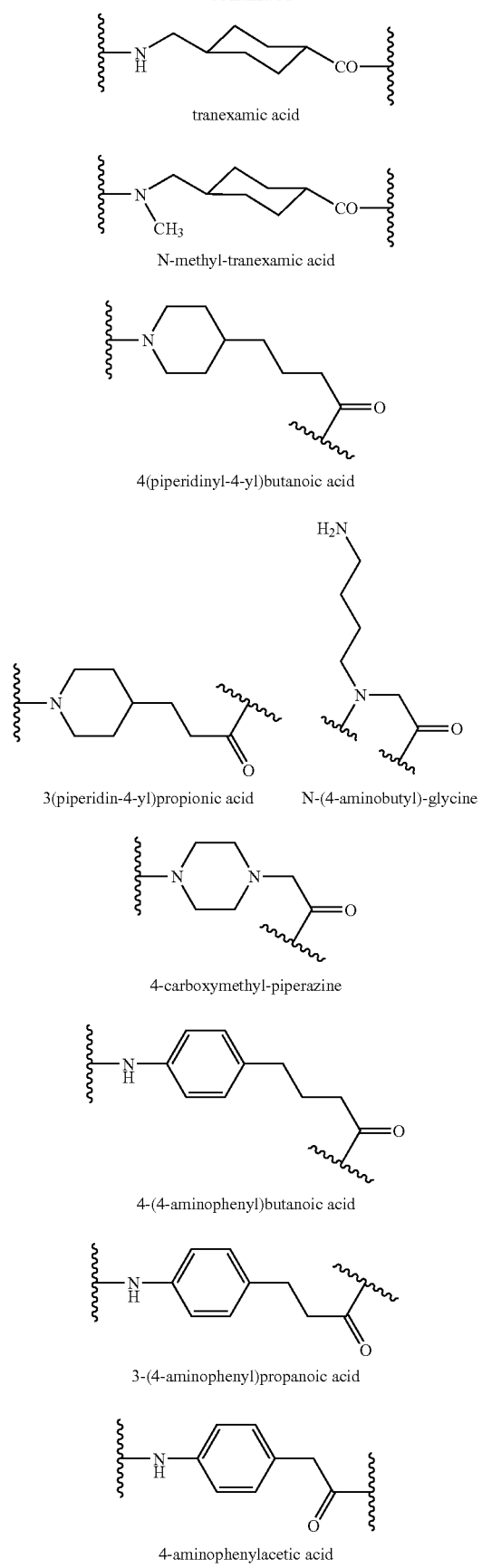
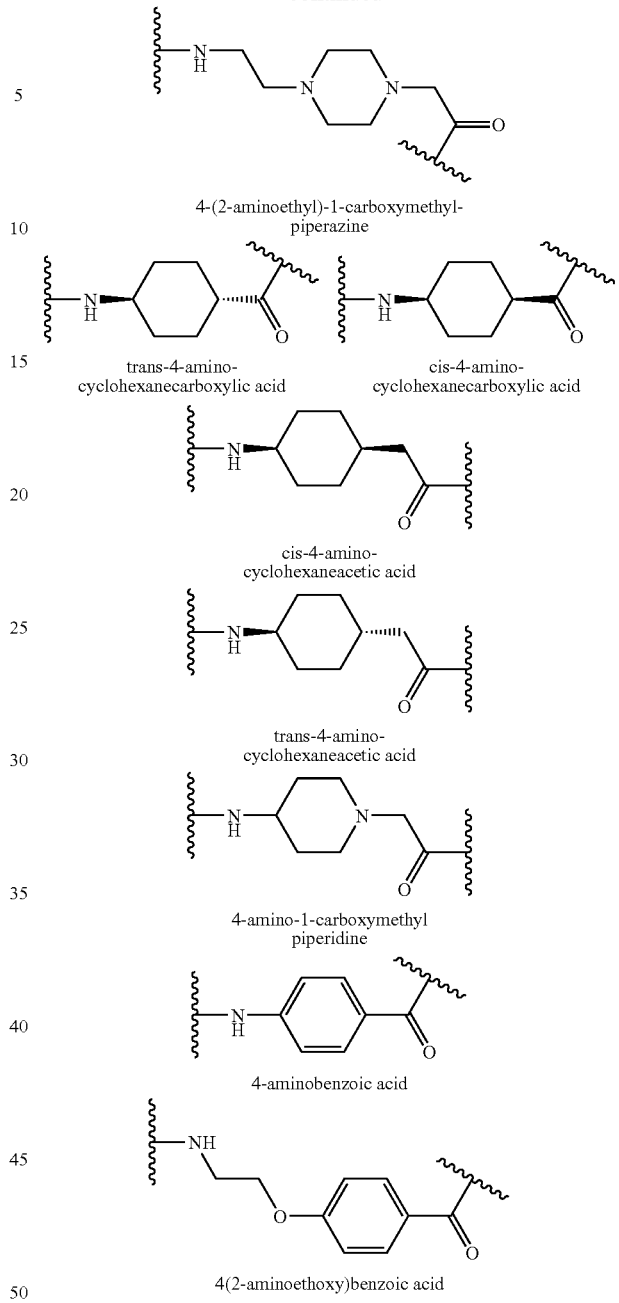

A preferred compound according to the invention is a compound of the abovementioned formula (I) in which:
 $X_a$ is not a lysine residue, and/or
 $X_b$ is not a glycine residue.

The replacement of the lysine residue makes it possible, on the one hand, to optimize the bond of the ligand to CD40, i.e. increase the affinity of the bond of said ligand to CD40 and, on the other hand, to modify the lipophily of this ligand.

The replacement of the glycine residue makes it possible to stabilize the bioactive conformation of the $X_a$—$X_b$—$X_c$—$X_d$ chaining According to a preferred embodiment, the compound of the invention is a compound of formula (I) as defined above, in which $X_a$ is not a lysine residue.

Thus, a preferred compound according to the present invention is characterized in that $X_a$ represents an amino acid residue of formula $NH_2—(CH_2)_n—COOH$, n varying from 1 to 10, and preferably in that $X_a$ represents an aminohexanoic acid residue.

Such compounds correspond to compounds in which the lysine residue of the $^{143}$Lys-Gly-Tyr-Tyr$^{146}$ (SEQ ID NO: 1) fragment of natural CD40 is replaced by an amino acid residue of formula $NH_2—(CH_2)_n—COOH$, n varying from 1 to 10.

A preferred compound of the invention is a compound corresponding to one of the following formulae:

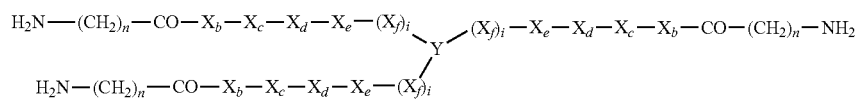

n being as defined above

The preferred compound corresponding to n=5 corresponds to the following formula:

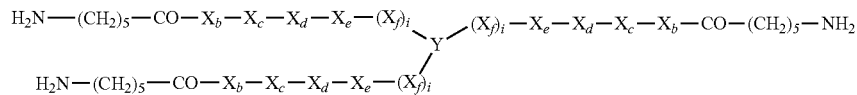

The replacement in this compound of said lysine residue by aminohexanoic acid makes it possible to modulate the lipophily of the ligand of the invention while preserving some of the effective functions of said ligand, resulting from its interaction with CD40 (apoptosis test on lymphomas, see experimental part).

Preferably, the compound of the invention is a compound of formula (I) as defined above, in which $X_a$ is not a lysine residue and in which the $X_b$, $X_c$ and $X_d$ residues are identical to the residues of the natural sequence of CD40L.

The present invention also relates to compounds of formula (I) as defined above, characterized in that $X_b$ is not a glycine residue.

Thus, a preferred compound according to the present invention is characterized in that $X_b$ represents a D-proline residue. Such a compound corresponds to the following formula:

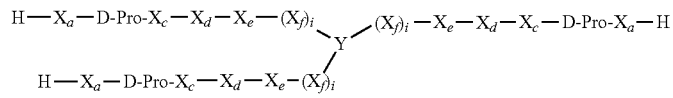

The replacement in this compound of the glycine residue of the $^{143}$Lys-Gly-Tyr-Tyr$^{146}$ (SEQ ID NO: 1) fragment of natural CD40 by a D-proline residue makes it possible to stabilize said ligand by stabilizing the type II' folding formed by the $^{143}$Lys-Gly-Tyr-Tyr$^{146}$ (SEQ ID NO: 1) loop of natural CD40. Thus, such a stabilization makes it possible to obtain more selective ligands, in particular by their capacity to induce a more specific apoptosis of the B lymphomas relative to the natural CD40 ligands, which are useful in particular within the framework of the apoptosis of lymphomas.

Preferably, the compound of the invention is a compound of formula (I) as defined above, in which $X_b$ is not a glycine residue and in which the $X_a$, $X_c$ and $X_d$ residues are identical to the residues of the natural sequence of CD40L.

A preferred compound according to the present invention is a compound in which $X_b$ represents an L-proline residue. The replacement in this compound of the glycine residue of the $^{143}$ Lys-Gly-Tyr-Tyr$^{146}$(SEQ ID NO: 1) fragment of natural CD40 by an L-proline residue makes it possible to obtain a ligand which has the same binding properties as the natural ligand to CD40, but which does not have the associated biological properties: this ligand therefore has no effect on the apoptosis of B lymphomas.

The present invention also relates to compounds of formula (I) as defined above, in which:

$X_a$ is not a lysine residue, and $X_b$ is not a glycine residue.

Preferably, the abovementioned compounds are characterized in that $X_a$ preferably represents an amino acid residue of formula $NH_2—(CH_2)_n—COOH$, n varying from 1 to 10, and in particular an aminohexanoic acid residue, and $X_b$ preferably represents a D-proline residue.

Such compounds correspond to one of the following general formulae:

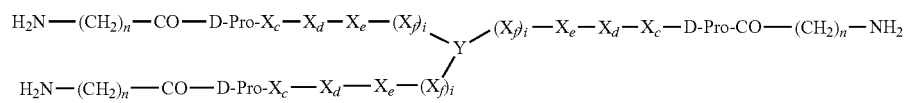

-continued

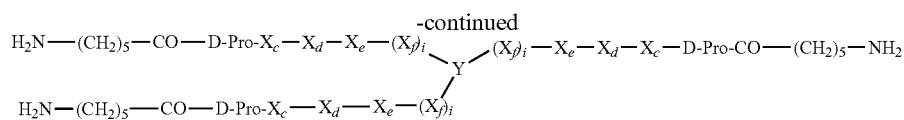

The present invention also relates to biotin-labelled compounds corresponding to formula (I) as defined above.

These compounds are used for preparing functionalized ligands making it possible to multimerize the ligands of the invention from a polymer. For this purpose it is possible in particular to use streptavidin which can bind to several biotins.

Thus, the present invention also relates to the ligands of the invention in multimeric form, i.e. corresponding to a polymer molecule to which several ligands according to the invention are bound, as well as the use of these multimerized ligands as labels.

These compounds can also make it possible to purify the CD40 receptor by the use of columns grafted by these compounds or to easily detect the CD40 receptor on the surface of the cells by using these labelled compounds, in particular within the framework of an immunotherapy of tumors with dendritic cells.

The present invention relates to compounds of formula (I) as defined above, characterized in that Y corresponds to the following formula (II):

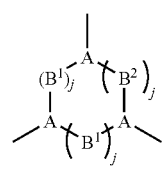

(II)

in which:

j is 0 or 1;

A represents an amino acid residue or an amino acid derivative chosen from any one of:

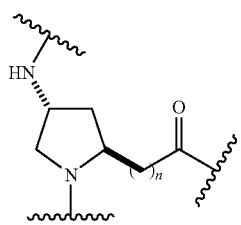
(1)

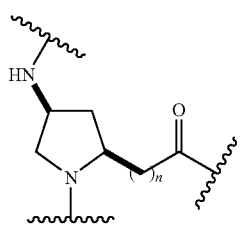
(2)

-continued

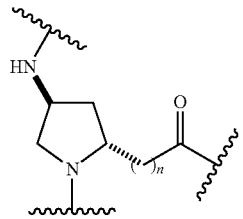
(3)

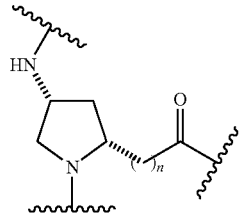
(4)

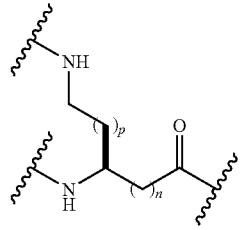
(5)

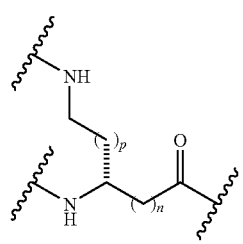
(6)

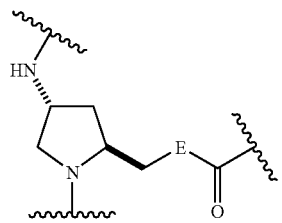
(7)

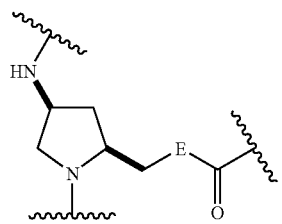
(8)

-continued (9)
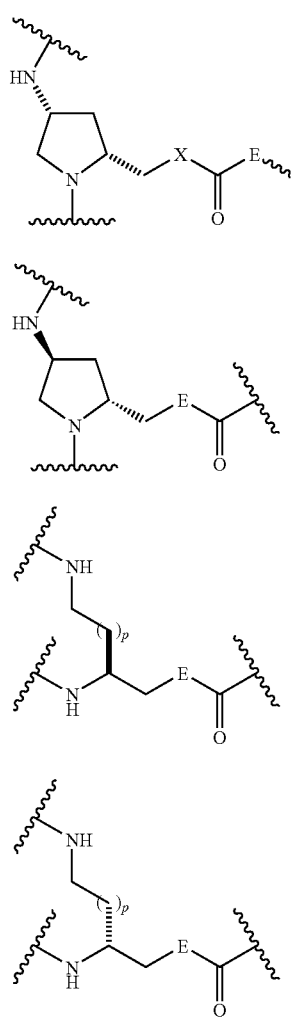

(10)

(11)

(12)

n representing 0, 1, 2 or 3;
p representing 0, 1, 2 or 3;
E representing NH or O;
B¹ is an amino acid residue or an amino acid derivative chosen independently from:

(13)

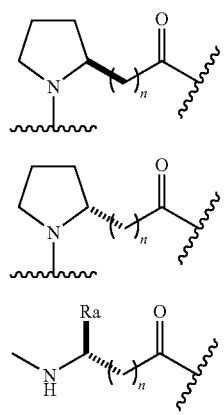

(14)

(15)

-continued

(16)
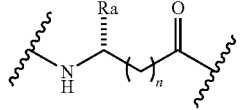

(17)
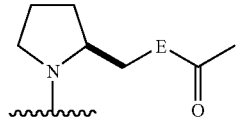

(18)
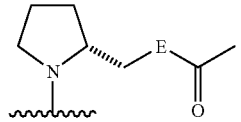

(19)
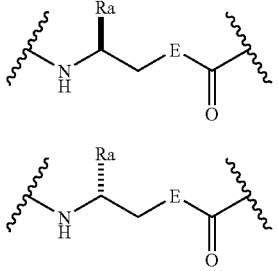

(20)

n representing 0, 1, 2 or 3;
p representing 0, 1, 2 or 3;
E representing NH or O;
Ra representing the chain of a proteinogenic amino acid, C1-C8 alkylated;
B² can be identical to B¹ or chosen independently from the following groups:

(13)
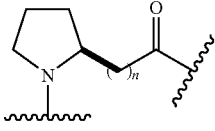

(14)
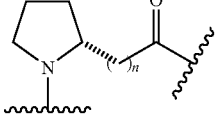

(15)
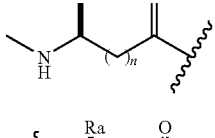

(16)

(17)
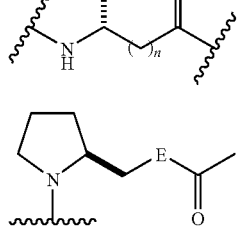

-continued (18)

(19)

(20)

(21)

(22)

(23)

(24)

n representing 0, 1, 2 or 3;
p representing 0, 1, 2 or 3;
E representing NH or O;
Ra representing the chain of a proteinogenic amino acid, C1-C8 alkylated;
D representing one of the following groups: (+)-Biotinyl-, (+)-Biotinyl-$X_g$—, HS—$(CH_2)_q$—CO—, Pys-S—$(CH_2)_q$—CO—, Npys-S—$(CH_2)_q$—CO—, HS—$(CH_2)_q$—CO—$X_g$—, Pys-S—$(CH_2)_q$—CO—$X_g$—, Npys-S—$(CH_2)_q$—CO—$X_g$
q representing an integer varying from 2 to 6;
$X_g$ corresponding to the residue of one of the following groups:

—$NH_2$—$(CH_2)_n$—COOH, n varying from 1 to 10;
—$NH_2$—$(CH_2$—$CH_2$—$O)_m$—$CH_2CH_2COOH$, m varying from 3 to 6;
8-amino-3,6-dioxaoctanoic acid;
tranexamic acid;
N-methyl-tranexamic acid;
4(piperidin-4-yl)butanoic acid;
3(piperidin-4-yl)-propionic acid;
N-(4-aminobutyl)-glycine;
4-carboxymethyl-piperazine;
4-(4-aminophenyl)butanoic acid;
3-(4-aminophenyl)propanoic acid;
4-aminophenylacetic acid;
4(2aminoethyl)-1-carboxymethyl-piperazine;
trans-4-aminocyclohexane carboxylic acid;
cis-4-aminocyclohexane carboxylic acid;
cis-4-aminocyclohexane acetic acid;
trans-4-aminocyclohexane acetic acid;
4-amino-1-carboxymethyl piperidine;
4-aminobenzoic acid;
4(2-aminoethoxy)benzoic acid.

In the abovementioned formula (II), A is a group of formula (1), (2), (3), (4), (5), (6), (7), (8), (9), (10), (11) or (12); $B^1$ is a group of formula (13), (14), (15), (16), (17), (18), (19) or (20) and $B^2$ is a group of formula (13), (14), (15), (16), (17), (18), (19), (20), (21), (22), (23) or (24).

$X_g$ corresponds to the same definitions as $X_e$ and $X_f$.

The term "Pys" designates the pyridine sulphenyl group and the term "Npys" designates the nitropyridine sulphenyl group.

The biotin corresponds to the formula

A biotinyl group therefore corresponds to the following formula:

The expression "chain of a proteinogenic amino acid" designates a side chain of an amino acid present in the proteins, corresponding or not corresponding to one of the 20 amino acids of the genetic code.

The compounds of formula (II) correspond to one of the following general formulae:

(II-a)

-continued

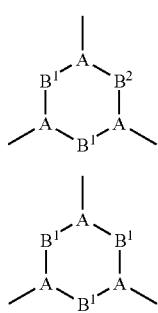
(II-b)

(II-c)

The present invention also relates to the compounds as defined above, corresponding to one of the following formulae:

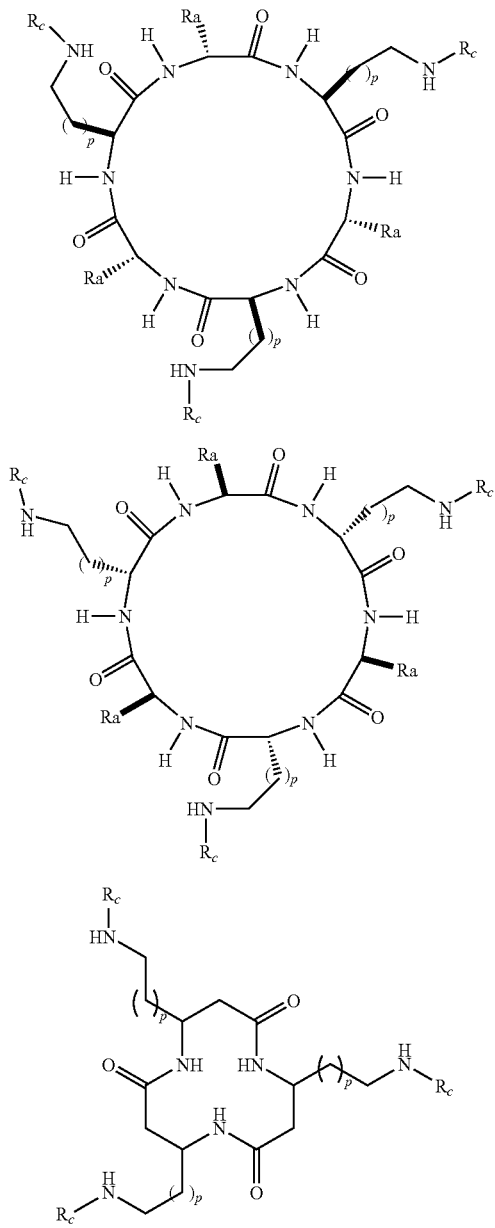

(III)

(IV)

(V)

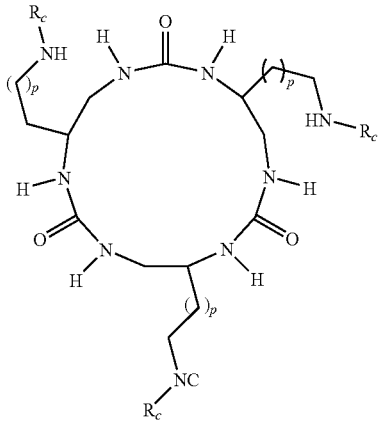

(VI)

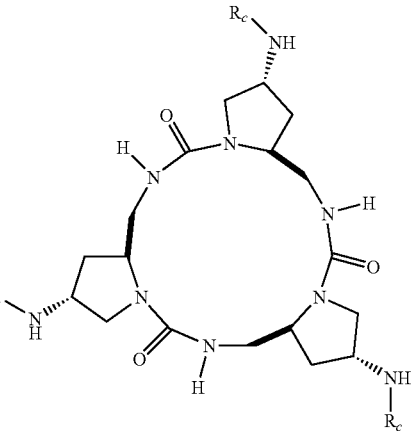

(VII)

Ra, $R_c$ and p being as defined above.

The compound of formula (III) corresponds to a compound of formula (I) with Y corresponding to formula (II-c) as defined above, in which A is a group of formula (5) and $B^1$ is a group of formula (16) where n=0.

The compound of formula (IV) corresponds to a compound of formula (I) with Y corresponding to formula (II-c) as defined above, in which A is a group of formula (6) and $B^1$ is a group of formula (15) where n=0.

The compound of formula (V) corresponds to a compound of formula (I) with Y corresponding to formula (II-a) as defined above, in which A is a group of formula (5) where n=1.

The compound of formula (VI) corresponds to a compound of formula (I) with Y corresponding to formula (II-a) as defined above, in which A is a group of formula (11) where E=NH.

The compound of formula (VII) corresponds to a compound of formula (I) with Y corresponding to formula (II-a) as defined above, in which A is a group of formula (10) where E=NH.

These different compounds are particularly useful to the extent that their structures are rigid and flat cyclic structures with well-defined conformations making it possible to orient and position the residues in contact with the receptor ($X_a$, $X_b$, $X_c$ and $X_d$), with a preferential geometry and distance for the interaction.

According to an advantageous embodiment, the compounds of the present invention correspond to the following formula (III-a):

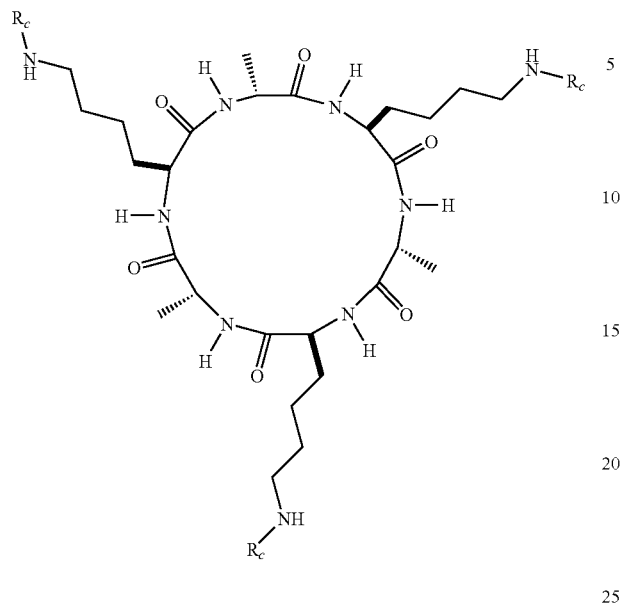

(III-a)

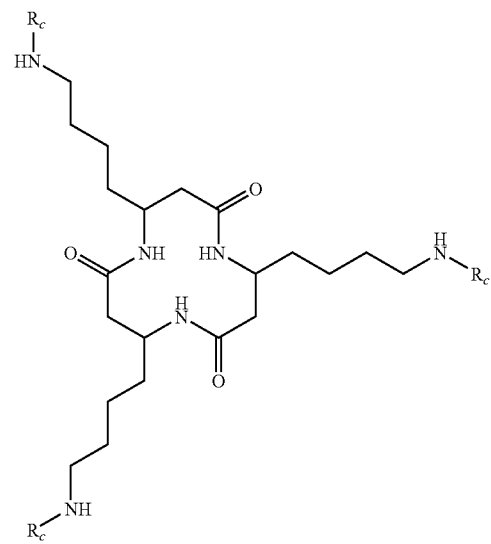

(V-a)

The compound of formula (III-a) corresponds to a compound of formula (III), in which $R_a$ represents a methyl group and p=3.

According to an advantageous embodiment, the compounds of the present invention correspond to the following formula (V-a):

The compound of formula (V-a) corresponds to a compound of formula (V), in which p=3.

According to an advantageous embodiment, the compounds of the present invention correspond to one of the following formulae:

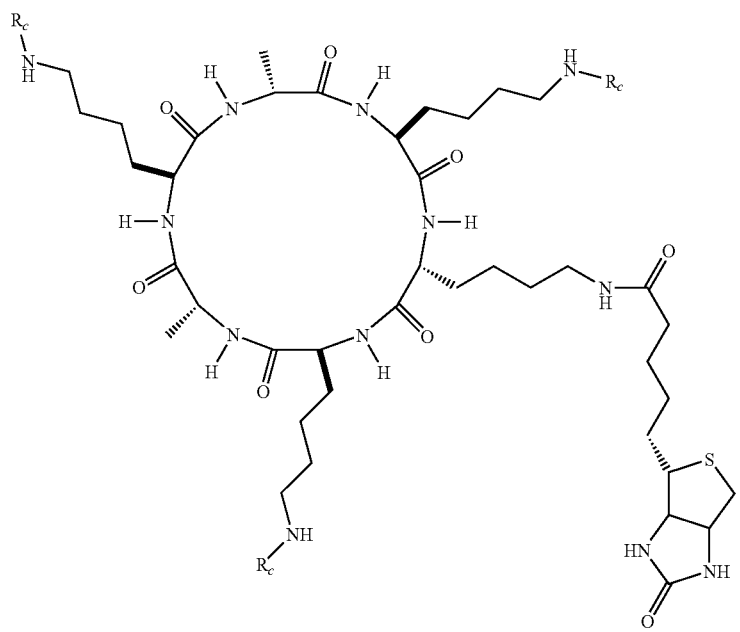

(III-b)

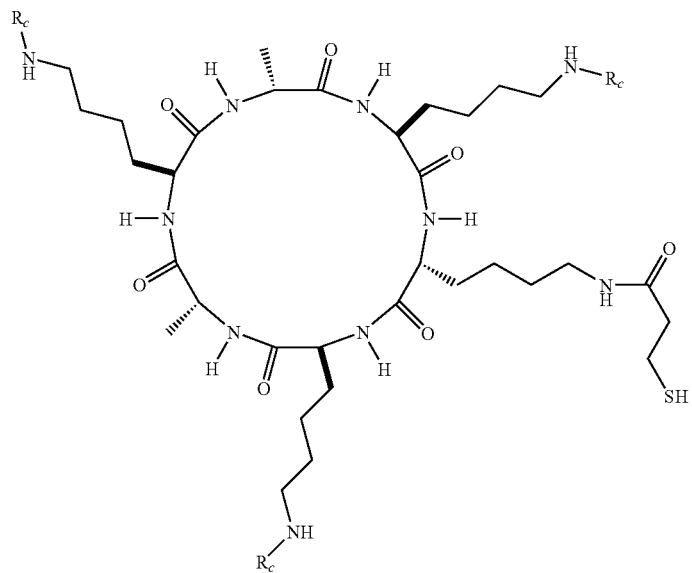

(III-c)

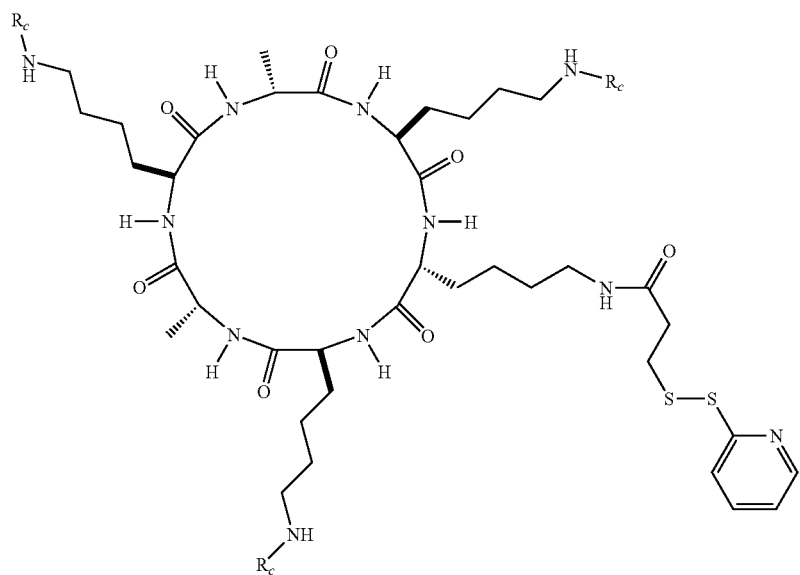

(III-d)

$R_c$ being as defined above.

The abovementioned compounds of formulae (III-b), (III-c) and (III-d) correspond to compounds of formula (III-a) labelled respectively by biotin, by a —CO—(CH$_2$)$_2$—SH and

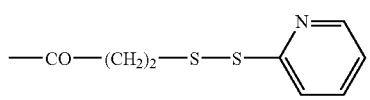

group. More exactly, these compounds are compounds of formula (I) with Y corresponding to formula (II-b) as defined above, in which A is a group of formula (5), B$^1$ is a group of formula (16) where n=0 and B$^2$ is a group of formula (22) where p=3.

In the compound of formula (III-b), D is a biotinyl group.

In the compound of formula (III-c), D is a —CO—(CH$_2$)$_q$—SH group, where q=2.

In the compound of formula (III-d), D is a —CO—(CH$_2$)$_q$—S-pys group, where q=2.

The preferred compounds of the invention are compounds of formula (I) as defined above, in which $R_c$ is:

H-Lys-(D)Pro-Tyr-Tyr-NH—(CH$_2$)$_5$—CO— (SEQ ID NO: 2) or

Ahx-(D)Pro-Tyr-Tyr-NH—(CH$_2$)$_5$—CO— (SEQ ID NO: 3) or

H-Lys-ψ(CH$_2$N)-(D)Pro-Tyr-Tyr-NH—(CH$_2$)$_5$—CO— (SEQ ID NO: 4), -ψ(CH$_2$N)- corresponding to a pseudopeptide bond of methylene-amino type or H-Lys-Gly-DOPA-Tyr-NH—(CH$_2$)$_5$—CO— (SEQ ID NO: 5).

The H-Lys-(D)Pro-Tyr-Tyr-NH—(CH$_2$)$_5$—CO— (SEQ ID NO: 2) group is an $R_c$ group in which i=0, $X_a$ is a lysine residue, $X_b$ is a D-proline residue, $X_c$ is a tyrosine residue, $X_d$ is a tyrosine residue and $X_e$ is a residue of the amino acid of formula NH$_2$—(CH$_2$)$_n$—COOH where n=5.

The H-Lys-ψ(CH$_2$N)-(D)Pro-Tyr-Tyr-NH—(CH$_2$)$_5$—CO— (SEQ ID NO: 4) group is an R$_c$ group in which i=0, X'$_a$ is a lysine residue, X'$_b$ is a D-proline residue, -ψ(CH$_2$N)— is a pseudopeptide bond of methylene-amino type (the CONH group of the peptide bond is replaced by a CH$_2$—N group), X$_c$ is a tyrosine residue, X$_d$ is a tyrosine residue and X$_e$ is a residue of the amino acid of formula NH$_2$—(CH$_2$)$_n$—COOH where n=5.

The H-Lys-Gly-DOPA-Tyr-NH—(CH$_2$)$_5$—CO— (SEQ ID NO: 5) group is an R$_c$ group in which i=0, X$_a$ is a lysine residue, X$_b$ is a glycine residue, X$_c$ is a residue of DOPA (3,4-dihydroxy-phenylalanine), X$_d$ is a tyrosine residue and X$_e$ is a residue of the amino acid of formula NH$_2$—(CH$_2$)$_n$—COOH where n=5.

Such compounds correspond to one of the following formulae:

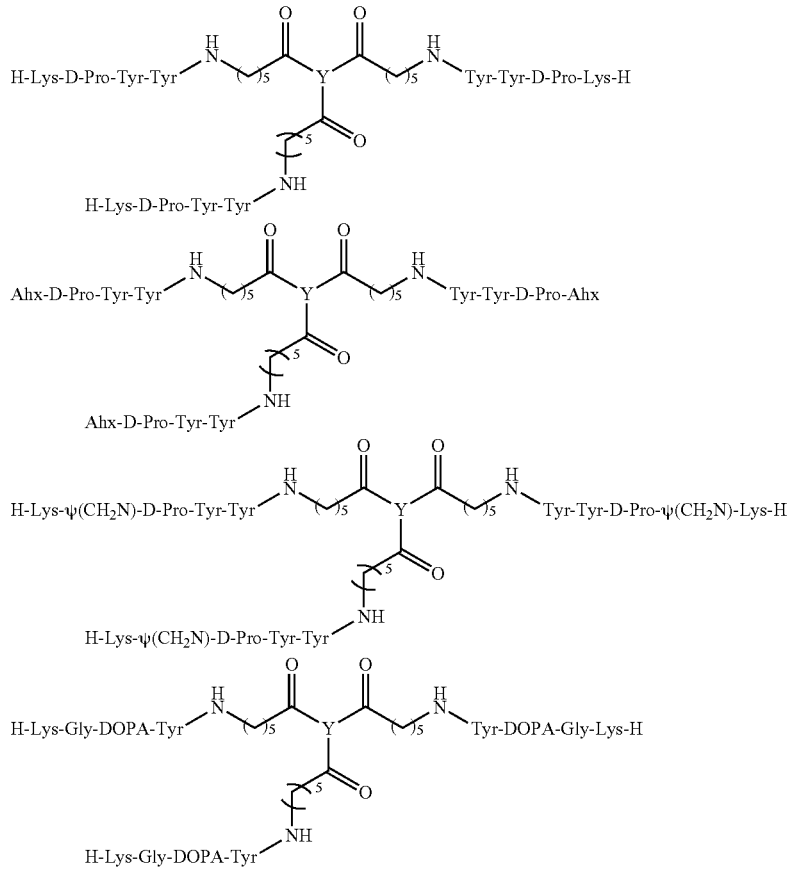

Y being as defined above.

These compounds can also be represented by one of the following formulae:

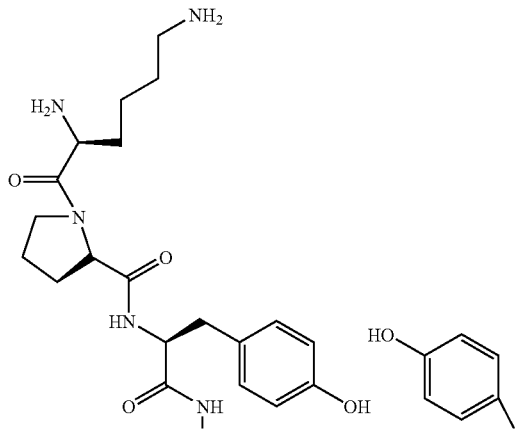

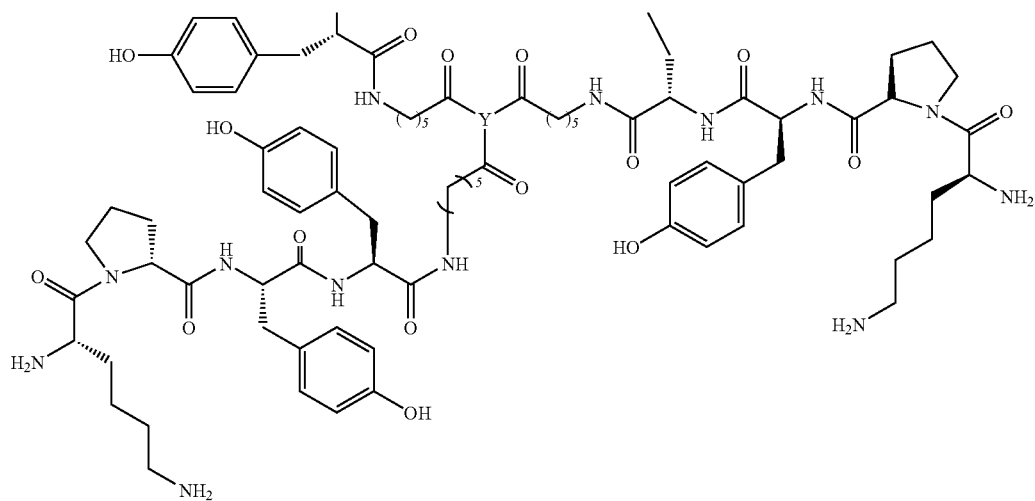
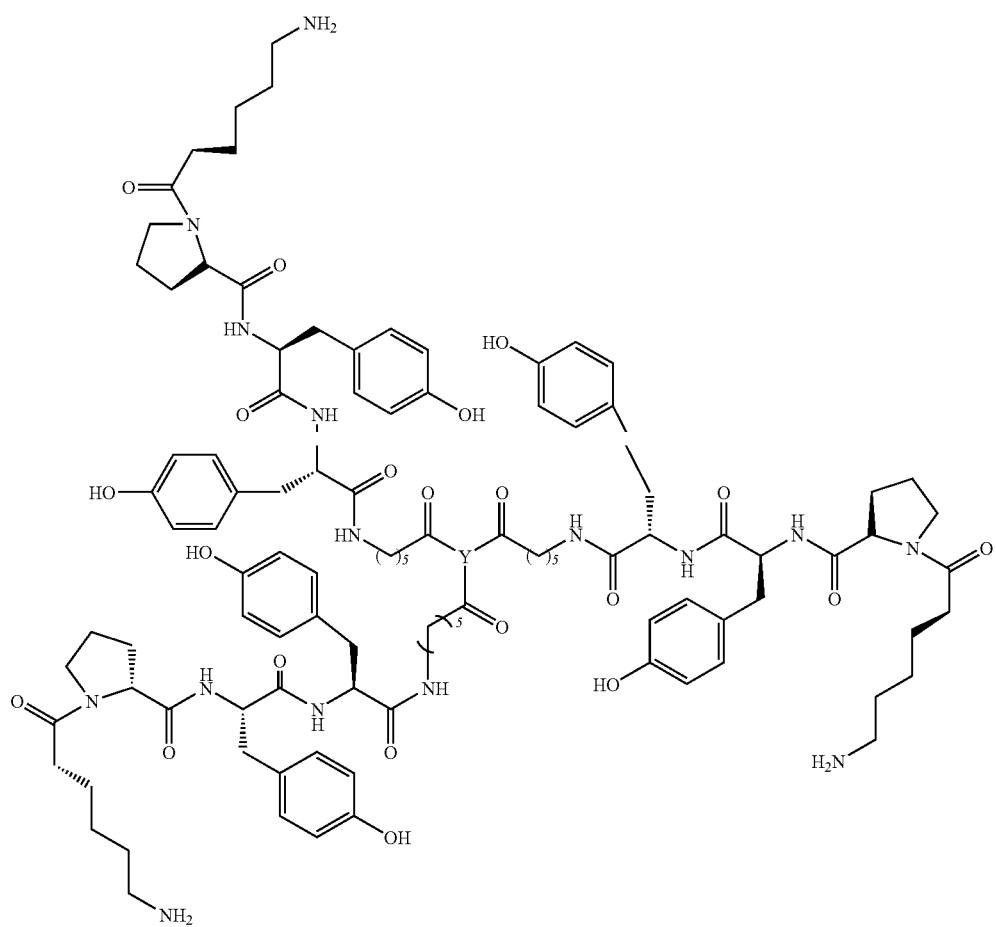

Preferred compounds of the invention correspond to one of the following formulae:
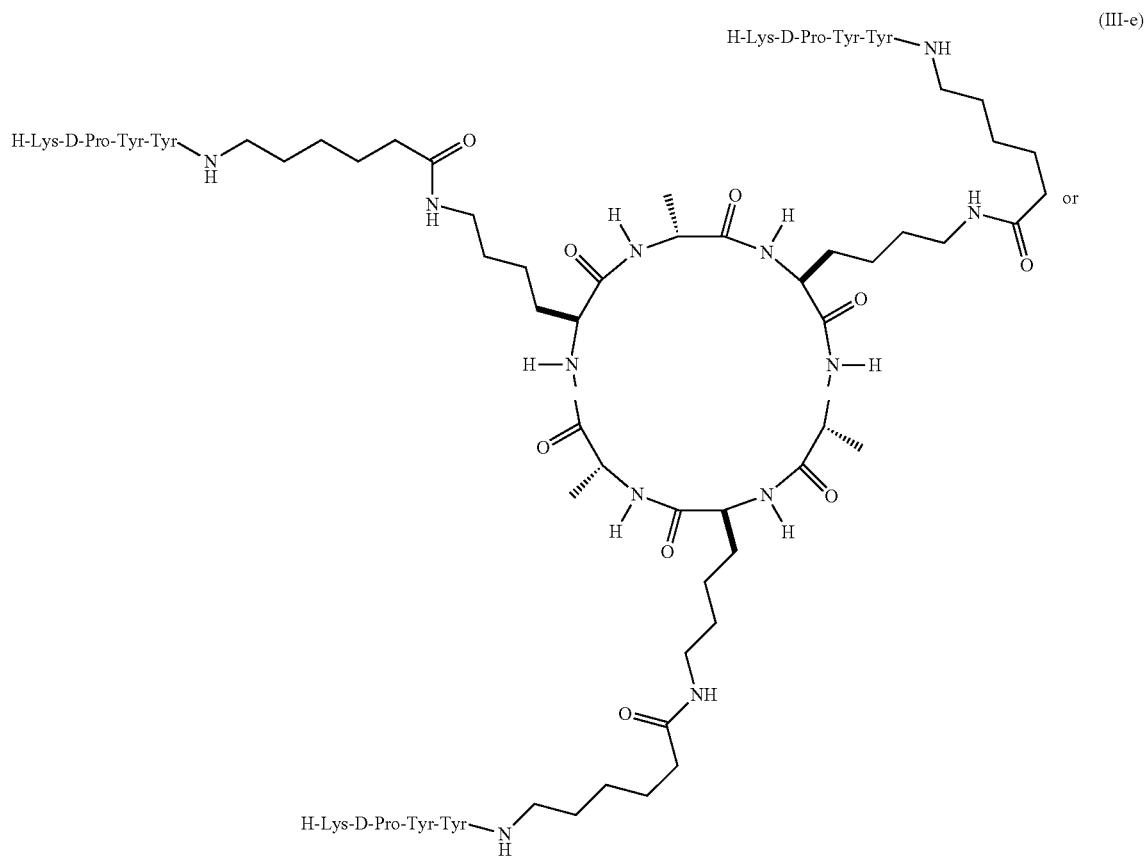
(III-e)
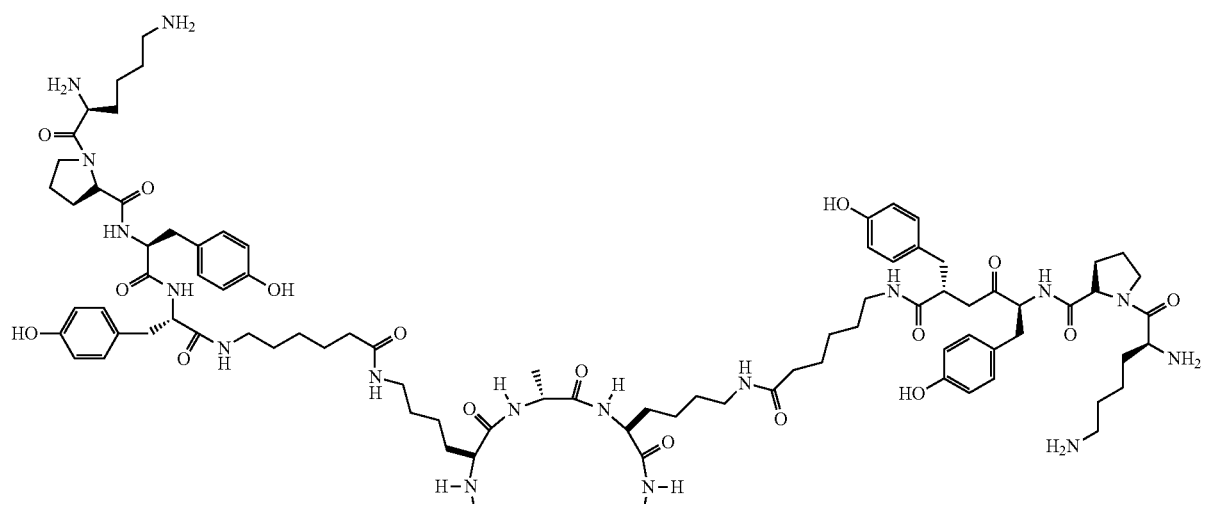

-continued
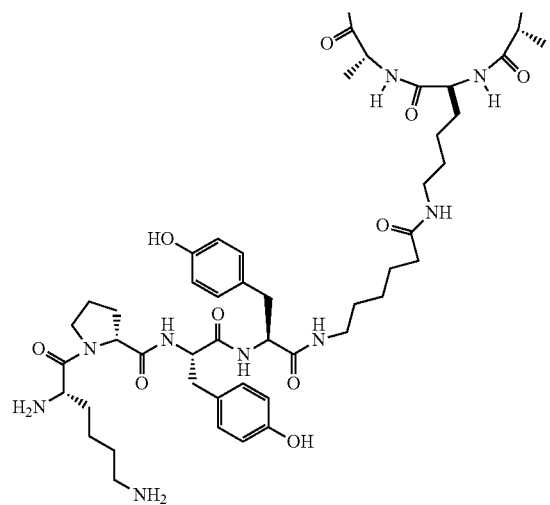
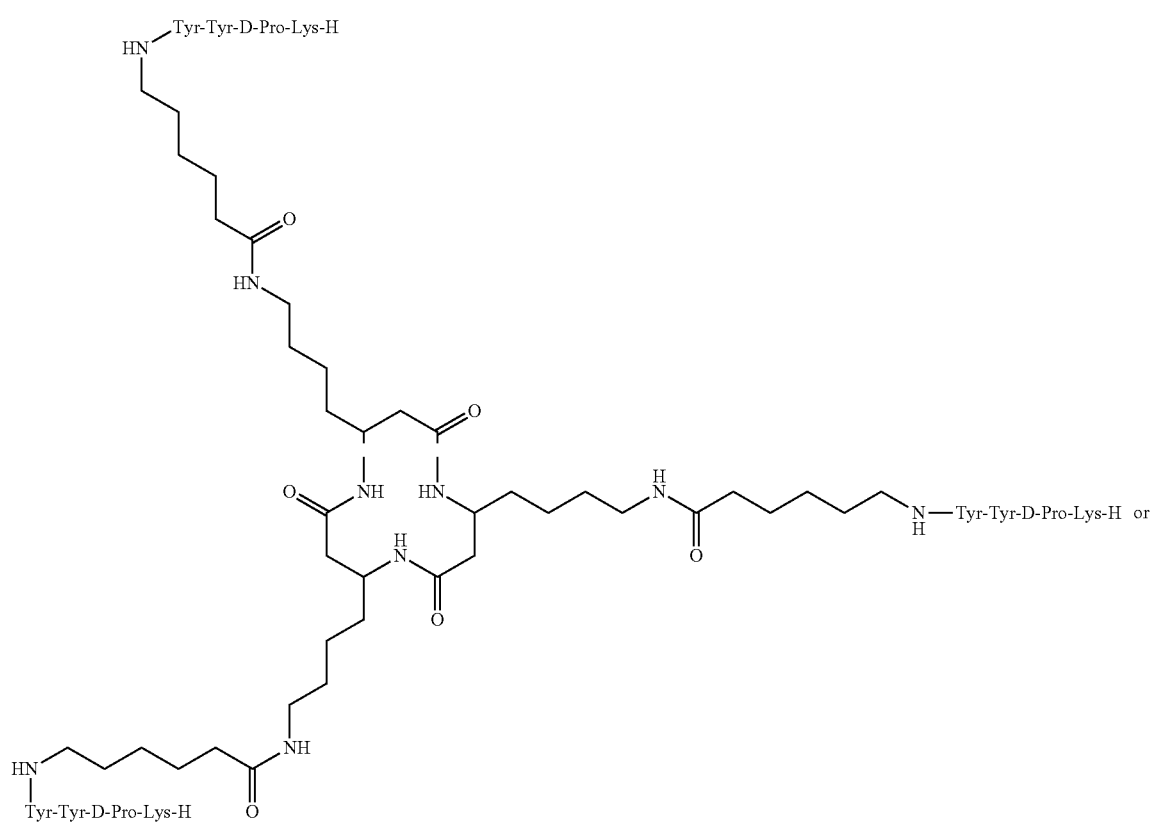
(V-b)

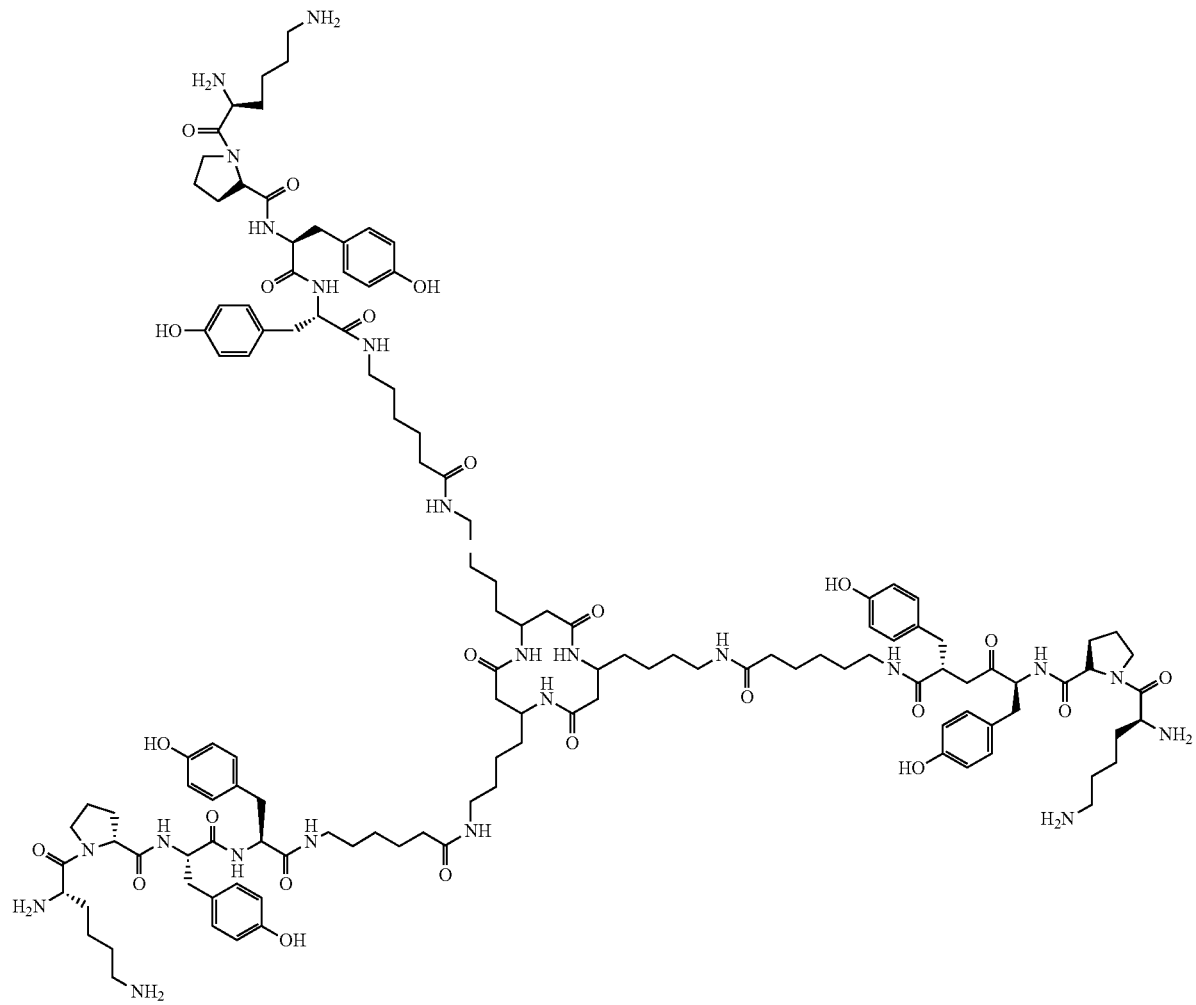
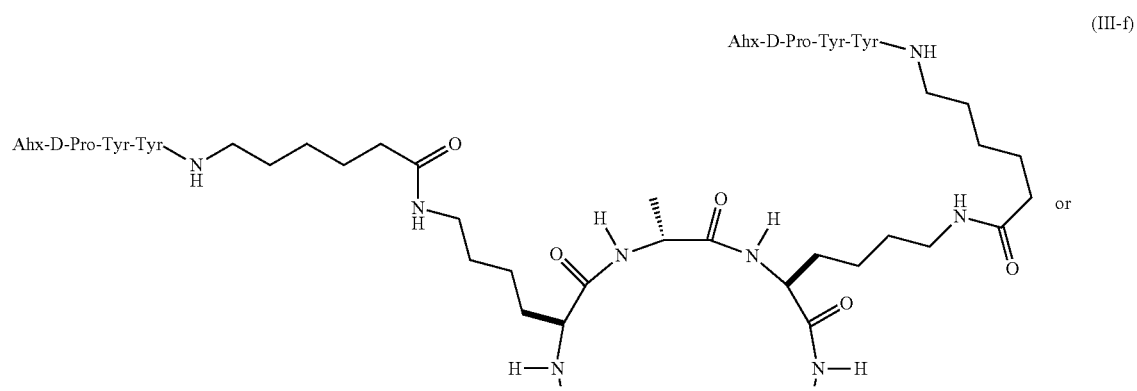
(III-f)

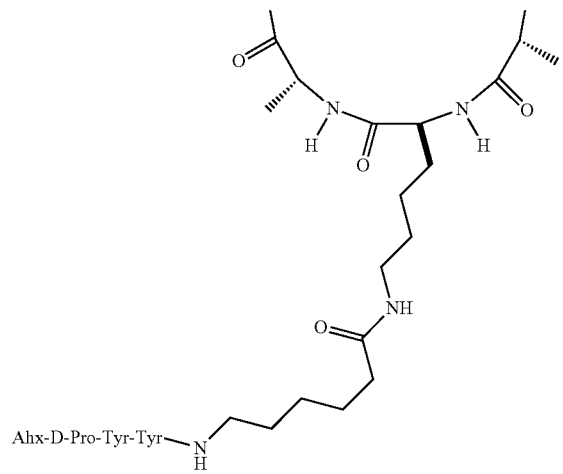
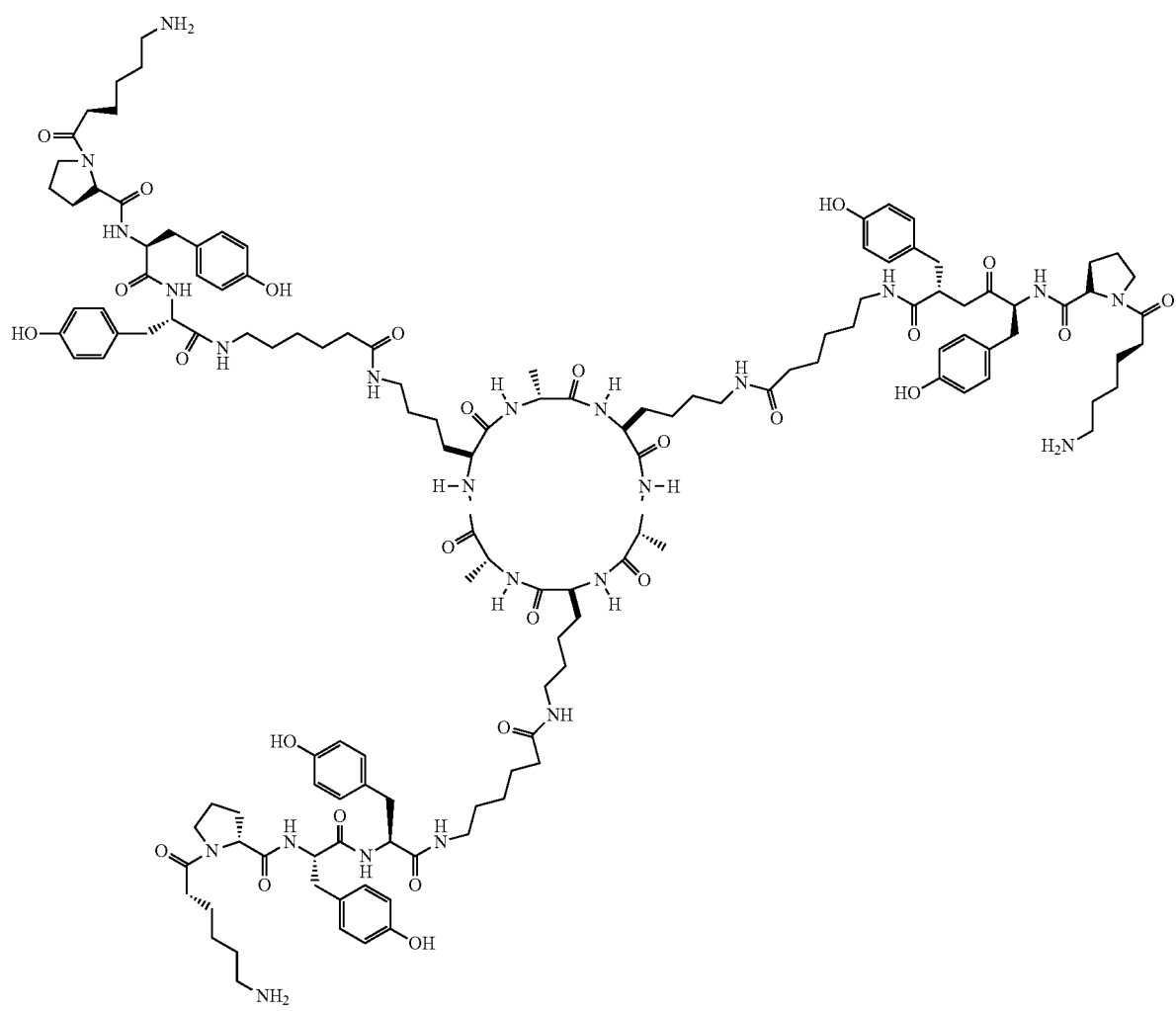

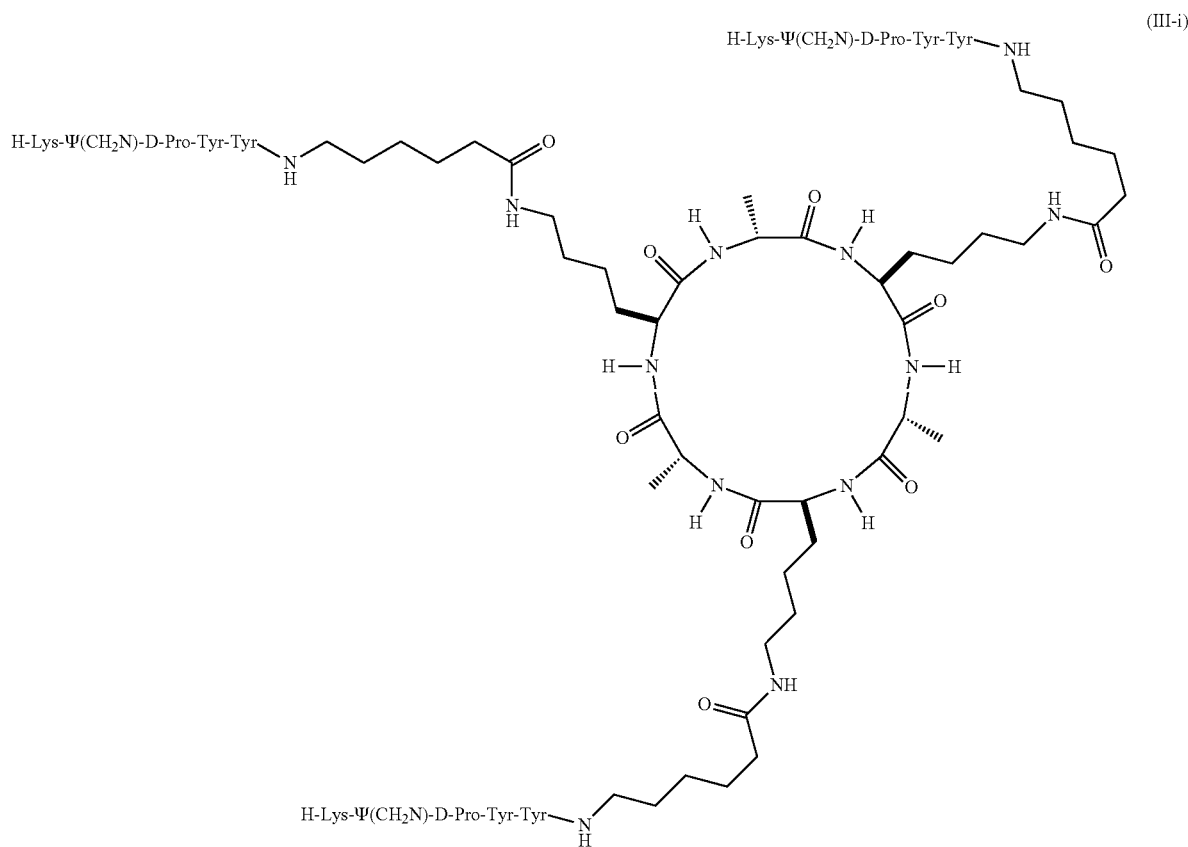

The compound of formula (III-e) is a compound of formula (III-a) in which $R_c$ is H-Lys-(D)Pro-Tyr-Tyr-NH—$(CH_2)_5$—CO— (SEQ ID NO: 2).

The compound of formula (V-b) is a compound of formula (V-a) in which $R_c$ is H-Lys-(D)Pro-Tyr-Tyr-NH—$(CH_2)_5$—CO— (SEQ ID NO: 2).

The compound of formula (III-f) is a compound of formula (III-a) in which $R_c$ is Ahx-(D)Pro-Tyr-Tyr-NH—$(CH_2)_5$—CO— (SEQ ID NO: 3).

The compound of formula (III-i) is a compound of formula (III-a) in which $R_c$ is H-Lys-ψ$(CH_2N)$-(D)Pro-Tyr-Tyr-NH—$(CH_2)_5$—CO— (SEQ ID NO: 4).

The present invention also relates to the compounds corresponding to one of the following formulae:

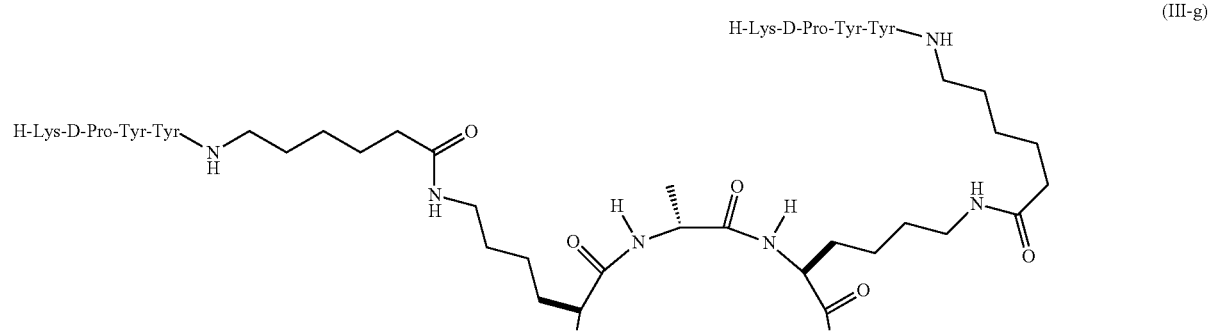

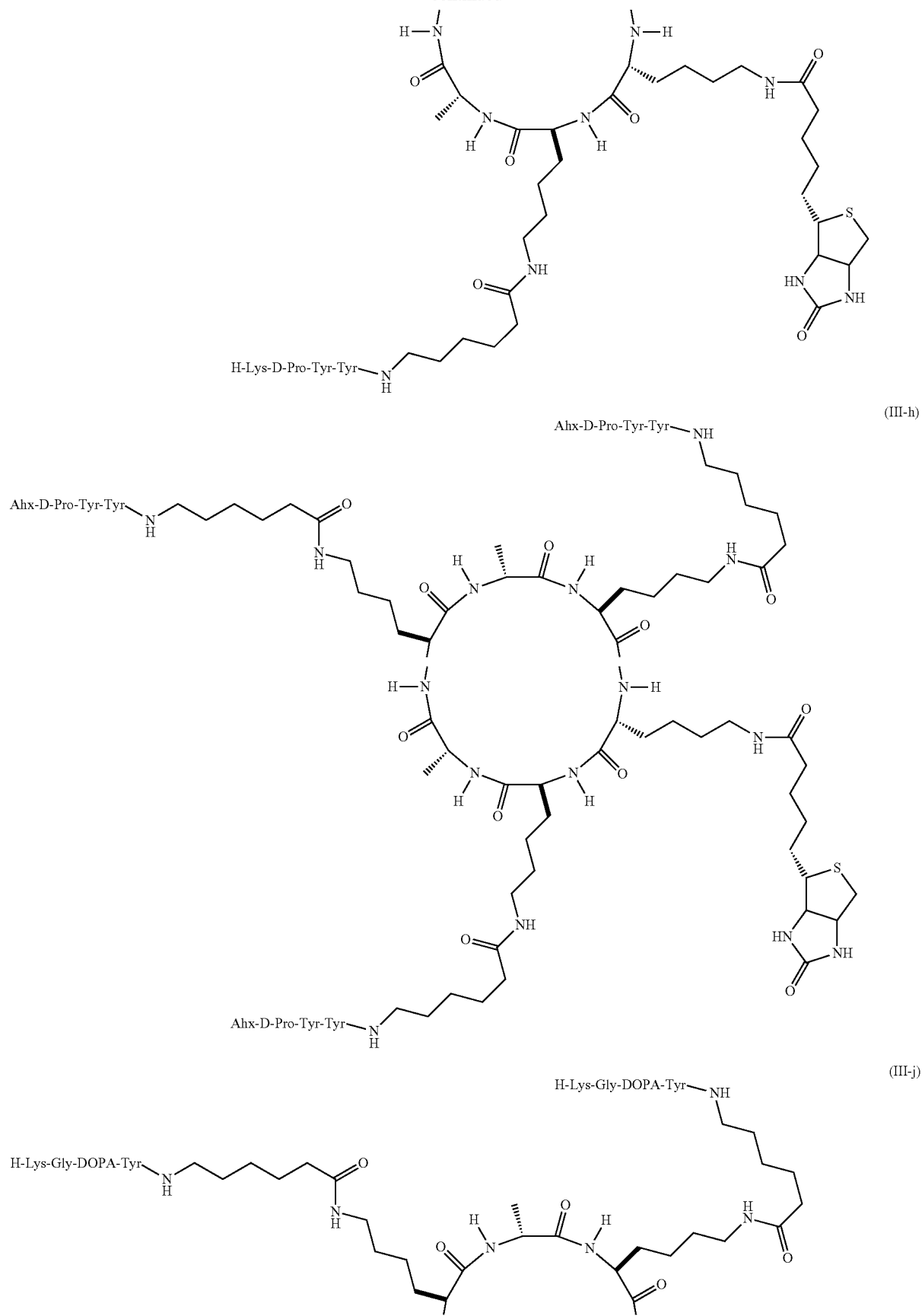

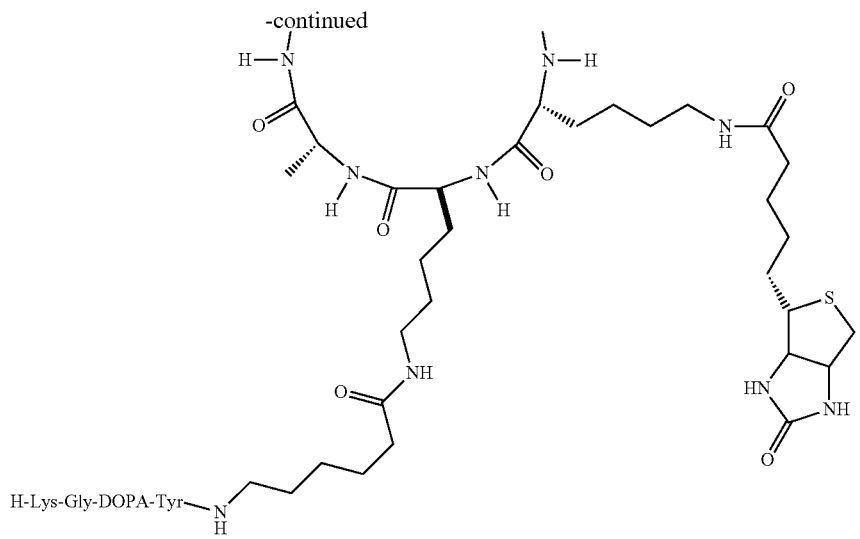

H-Lys-Gly-DOPA-Tyr—

Compound (III-g) is a biotin-labelled compound of formula (III-e). This compound also corresponds to a compound of formula (III-b) in which $R_c$ is an H-Lys-(D) Pro-Tyr-Tyr- (SEQ ID NO: 6) group.

Compound (III-h) is a biotin-labelled compound of formula (III-f). This compound also corresponds to a compound of formula (III-b) in which $R_c$ is an Ahx-(D) Pro-Tyr-Tyr- (SEQ ID NO: 7) group.

Compound (III j) is a biotin-labelled compound. This compound also corresponds to a compound of formula (III-b) in which $R_c$ is an H-Lys-Gly-DOPA-Tyr-NH—$(CH_2)_5$—CO— (SEQ ID NO: 5) group.

The present invention also relates to a pharmaceutical composition characterized in that it comprises, as active ingredient, a compound as defined above, corresponding to formula (I), in combination with a pharmaceutically acceptable vector.

The present invention also relates to a vaccine composition, characterized in that it comprises, as active ingredient, a compound as defined above, corresponding to formula (I), in combination with a pharmaceutically acceptable adjuvant.

The present invention also relates to the use of compounds as defined above, corresponding to formula (I), for the preparation of a medicament intended for the treatment of pathologies involving the inhibition or the activation of the immune response.

The immune response must be inhibited in the course of inflammatory diseases (inflammatory rheumatism), auto-immune diseases, hypersensitivity reactions in general and allergies in particular, graft rejections, reactions of the graft against the host.

The immune response must be activated in vaccinations in general, in cancer immunotherapy, in bacterial or viral diseases inducing an immunosuppression (measles, AIDS, herpes virus, cytomegalovirus etc.), in the treatment of bacterial, viral diseases or diseases involving non-conventional infectious agents (prions) in individuals exhibiting a primary or secondary immune deficit.

The present invention also relates to the use as mentioned above, for the preparation of a medicament intended for the treatment of pathologies involving the inhibition of the immune response, such as graft rejections, allergies or auto-immune diseases.

Diseases involving the inhibition of the immune response comprise auto-immune diseases such as diabetes, multiple sclerosis, disseminated erythematous lupus or rheumatoid arthritis, graft rejections, in particular within the framework of allografts, xenografts or reactions of the graft against the host, as well as hypersensitivity reactions such as allergies, in particular allergic rhinitis and atopic dermatitis, or granulomas.

The compounds according to the present invention, used within the framework of the inhibition of the immune response, can be administered by intravenous route, by the mucous-membrane routes (oral, airways, nasal, vaginal), by sub-cutaneous, intradermal or epicutaneous route.

The present invention also relates to a pharmaceutical composition, characterized in that it comprises a compound according to the present invention, for the treatment of pathologies involving the inhibition of the immune response, which compound is present in the pharmaceutical composition in quantities such that it can be administered at a rate of approximately 100 ng to approximately 5 mg per day and per individual.

The present invention also relates to the use as mentioned above, for the preparation of a medicament intended for the treatment of pathologies involving the boosting of the immune response, such as cancers or parasitic, bacterial, or viral infections or infections involving non-conventional infectious agents such as prions.

Cases involving the activation of the immune response comprise vaccinations in general, in particular vaccines against influenza or against infantile diseases, cancer immunotherapy, in particular within the framework of melanomas or cancers with metastases, or bacterial or viral diseases inducing immunosuppression, in particular within the framework of measles, AIDS, herpes virus or cytomegalovirus, or vaccines intended for individuals exhibiting a primary or secondary immune deficit.

The compounds according to the present invention, used within the framework of the activation of the immune response, can be administered by intravenous route, by the mucous-membrane routes (oral, airways, nasal, vaginal), by sub-cutaneous, intradermal or epicutaneous route.

The present invention also relates to a pharmaceutical composition, characterized in that it comprises a compound according to the present invention, for the treatment of pathologies involving the activation of the immune response, which compound is present in the pharmaceutical composition in quantities such that it can be administered at a rate of approximately 100 ng to approximately 5 mg per day and per individual.

The present invention also relates to a process of preparation on a solid support of a compound of formula (I) as defined above, said process being characterized in that it comprises the following stages:
- the formation of a linear precursor of Y, which precursor is constituted by a chaining of amino acids forming a growing peptide chain, synthesized by successive cycles of coupling between N-protected amino acid residues, three of which carry an amine-type group, and the amine function of the growing peptide chain, and of deprotection, the first amino acid residue being attached to a solid support,
- the cyclization of the abovementioned protected linear precursor of Y,
- the cleavage of said protective groups, in order to release said protected amine functions,
- the coupling of the abovementioned released amine functions with a peptide which is already formed or formed in situ by the sequential assembly of the amino acid residues corresponding to the $R_c$ group, and
- the cleavage of the molecule from the solid support, after the deletion of all the protective groups present on the functionalized side chains of the $R_c$ group, in order to obtain the compound according to the invention.

The compounds of the invention are obtained by synthesis on solid support according to the process described hereafter. The Y group is first constructed on solid support by synthesis of its linear precursor and cyclization. Thus, a first amino acid residue, the acid function of which is suitably protected (allyl ester for example), is attached to the support by a reductive amination reaction, using a resin functionalized by an aldehyde (commercial resins). The linear precursor of Y is then assembled by successive cycles of coupling (in standard manner in peptide synthesis) with an N-protected amino acid (N-Fmoc-Xaa-OH for example, Xaa representing any amino acid or growing peptide) and of deprotection (20% piperidine in DMF for the cleavage of an Fmoc group). The techniques of washing and of filtration of the resin as well as of deprotection of the Fmoc group are those commonly used in peptide synthesis in solid phase. The three amino acids carrying an amine-type chain are functionalized and the amine function is protected by a protective group orthogonal to the others (TEOC or methyltrityl for example). At the end of the assembly, the last N-protective group is cleaved (in the presence of 20% piperidine in DMF in the case of an Fmoc group) and the protection of the C-terminal ester is cleaved. The linear precursor is then cyclized "head to tail" in the presence of a coupling reagent (standard in peptide synthesis) and a tertiary base such as DIEA or collidine for example. The cyclization reaction can be followed by a colorimetric test such as the Kaiser test (Kaiser et al., 1970). At the end of the cyclization, the protective groups of the amino acids possessing a protected amine function are cleaved and the spacer arm, suitably protected (Fmoc-Ahx (6-amino hexanoic acid)-COOH for example), is coupled in the presence of a coupling agent to the three free amine functions. On completion of this coupling, the protective group of the spacer arm is cleaved and the $R_c$ group is assembled by standard peptide synthesis methods. At the end of the synthesis and once the last protective group is removed, the molecule is cleaved from the resin, for example by treatment with trifluoroacetic acid, lyophilized after precipitation from ether and purified by reversed-phase preparative HPLC on a C18 column for example.

The present invention also relates to biotin-labelled compounds corresponding to the following formula

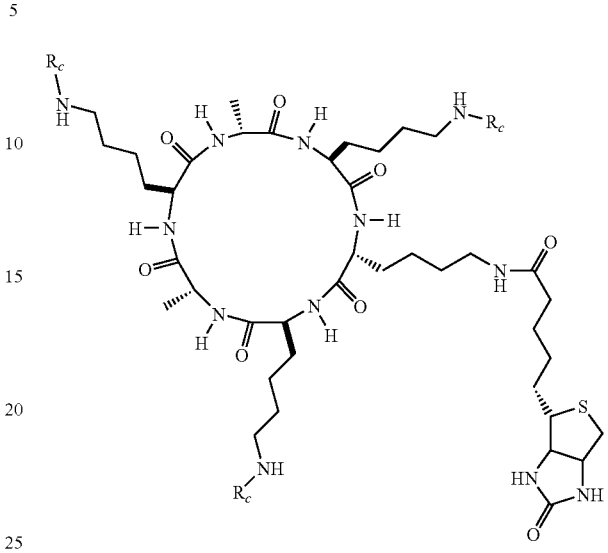

in which:
$R_c$ represents a group of formula H—$X_a$—$X_b$—$X_c$—$X_d$—$X_e$—$(X_f)_i$— or H—$X'_a$-L-$X'_b$—$X_c$—$X_d$—$X_e$—$(X_f)_i$—,
in which:
i represents 0 or 1,
$X_a$ is chosen from the following amino acid residues:
  lysine;
  arginine;
  ornithine;
  the β-amino acids corresponding to lysine, arginine or ornithine, carrying the substitution in α or β position;
  tranexamic acid;
  N-methyl-tranexamic acid;
  8-amino-3,6-dioxaoctanoic acid;
  4(piperidin-4-yl)butanoic acid;
  3(piperidin-4-yl)propionic acid;
  N-(4-aminobutyl)-glycine;
  $NH_2$—$(CH_2)_n$—COOH, n varying from 1 to 10;
  $NH_2$—$(CH_2$—$CH_2$—O$)_m$—$CH_2CH_2COOH$, m varying from 3 to 6;
  4-carboxymethyl-piperazine;
  4-(4-aminophenyl)butanoic acid;
  3-(4-aminophenyl)propanoic acid;
  4-aminophenylacetic acid;
  4-(2aminoethyl)-1-carboxymethyl-piperazine;
  trans-4-aminocyclohexanecarboxylic acid;
  cis-4-aminocyclohexanecarboxylic acid;
  cis-4-aminocyclohexane acetic acid;
  trans-4-aminocyclohexane acetic acid;
  4-amino-1-carboxymethyl piperidine;
  4-aminobenzoic acid;
  4(2-aminoethoxy)benzoic acid;
$X_b$ is chosen from the following amino acid residues:
  glycine;
  asparagine;
  D-alanine;
  D-valine;
  L-proline substituted or non-substituted in β, γ or δ position;

D-proline substituted or non-substituted in γ, γ or δ position;
N-alkylated natural amino acids, the alkyl group being a methyl, ethyl or benzyl group;
acyclic dialkylated amino acids of the following formula:

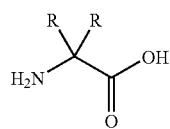

(A)

R representing H, Me, Et, Pr or Bu;
cyclic dialkylated amino acids of the following formula:

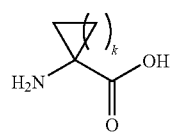

(B)

k representing 1, 2, 3 or 4;
$X_c$ is chosen from the following amino acid residues:
tyrosine;
phenylalanine;
3-nitro-tyrosine;
4-hydroxymethyl-phenylalanine;
3,5-dihydroxy-phenylalanine;
2,6-dimethyl-tyrosine;
3,4-dihydroxy-phenylalanine (DOPA);
$X_d$ is chosen from the following amino acid residues:
tyrosine;
phenylalanine;
3-nitro-tyrosine;
4-hydroxymethyl-phenylalanine;
3,5-dihydroxy-phenylalanine;
2,6-dimethyl-tyrosine;
3,4-dihydroxy-phenylalanine;
$X_e$ is chosen from the following amino acid residues:
NH$_2$—(CH$_2$)$_n$—COOH, n varying from 1 to 10;
NH$_2$—(CH$_2$—CH$_2$—O)$_m$—CH$_2$CH$_2$COOH, m varying from 3 to 6;
8-amino-3,6-dioxaoctanoic acid;
tranexamic acid;
N-methyl-tranexamic acid;
4(piperidin-4-yl)butanoic acid;
3(piperidin-4-yl)propionic acid;
N-(4-aminobutyl)-glycine;
4-carboxymethyl-piperazine;
4-(4-aminophenyl)butanoic acid;
3-(4-aminophenyl)propanoic acid;
4-aminophenylacetic acid;
4-(2aminoethyl)-1-carboxymethyl-piperazine;
trans-4-aminocyclohexanecarboxylic acid;
cis-4-aminocyclohexanecarboxylic acid;
cis-4-aminocyclohexane acetic acid;
trans-4-aminocyclohexane acetic acid;
4-amino-1-carboxymethyl piperidine;
4-aminobenzoic acid;
4(2-aminoethoxy)benzoic acid;

$X_f$ is chosen from the following amino acid residues:
NH$_2$—(CH$_2$)$_n$—COOH, n varying from 1 to 10;
NH$_2$—(CH$_2$—CH$_2$—O)$_m$—CH$_2$CH$_2$COOH, m varying from 3 to 6;
8-amino-3,6-dioxaoctanoic acid;
tranexamic acid;
N-methyl-tranexamic acid;
4(piperidin-4-yl)butanoic acid;
3(piperidin-4-yl)propionic acid;
N-(4-aminobutyl)-glycine;
4-carboxymethyl-piperazine;
4-(4-aminophenyl)butanoic acid;
3-(4-aminophenyl)propanoic acid;
4-aminophenylacetic acid;
4-(2aminoethyl)-1-carboxymethyl-piperazine;
trans-4-aminocyclohexanecarboxylic acid;
cis-4-aminocyclohexanecarboxylic acid;
cis-4-aminocyclohexane acetic acid;
trans-4-aminocyclohexane acetic acid;
4-amino-1-carboxymethyl piperidine;
4-aminobenzoic acid;
4(2-aminoethoxy)benzoic acid;
-L- represents a pseudopeptide-type bond between the $X'_a$ and $X'_b$ residues, chosen in particular from the list below:
-L-=-ψ(CH$_2$CH$_2$)—; -ψ(CH(F$_k$)=CH(F$_k$'))—; -ψ(CH$_2$NH)—; -ψ(NHCO)—; -ψ(NHCONH)—; -ψ(CO—O)—; -ψ(CS—NH)—; -ψ(CH(OH)—CH(OH))—; -ψ(S—CH$_2$)—; -ψ(CH$_2$—S)—; -ψ(CH(CN)—CH$_2$)—; -ψ(CH(OH))—; -ψ(COCH$_2$)—; -ψ(CH(OH)CH$_2$)—; -ψ(CH(OH)CH$_2$NH)—; -ψ(CH$_2$)—; -ψ(CH(F$_k$)—; -ψ(CH$_2$O)—; -ψ(CH$_2$—NHCONH)—; -ψ(CH(F$_k$)NHCONF$_k$')—; -ψ(CH$_2$—CONH)—; -ψ(CH(F$_k$)CONH)—; -ψ(CH(F$_k$)CH(F$_k$')CONH)—;
or -ψ(CH$_2$N)—; -ψ(NHCON)—; -ψ(CS—N)—; -ψ(CH(OH)CH$_2$N)—; -ψ(CH$_2$—NHCON)—; -ψ(CH$_2$—CON)—; -ψ(CH(F$_k$)CON)—; -ψ(CH(F$_k$)CH(F$_k$')CON)— when $X'_b$ represents the side chain of a proline,
$F_k$ and $F_k'$ representing, independently of one another, a hydrogen, a halogen, an alkyl group of 1 to 20 carbon atoms, or an aryl group the ring structure of which contains from 5 to 20 carbon atoms,
$X'_a$ represents the side chain of lysine, arginine or ornithine; and
$X'_b$ represents the side chain of one of the following amino acid residues:
glycine;
asparagine;
D-alanine;
D-valine;
L-proline substituted or non-substituted in β, γ or δ position;
D-proline substituted or non-substituted in β, γ or δ position;
N-alkylated natural amino acids, the alkyl group being a methyl, ethyl or benzyl group;
acyclic dialkylated amino acids of the following formula:

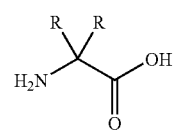

(A)

R representing H, Me, Et, Pr or Bu;

cyclic dialkylated amino acids of the following formula:

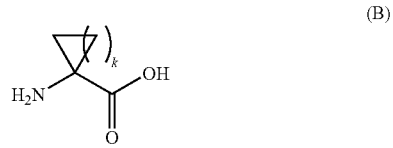

(B)

k representing 1, 2, 3 or 4.

LIST OF THE ABBREVIATIONS

Figure 1:
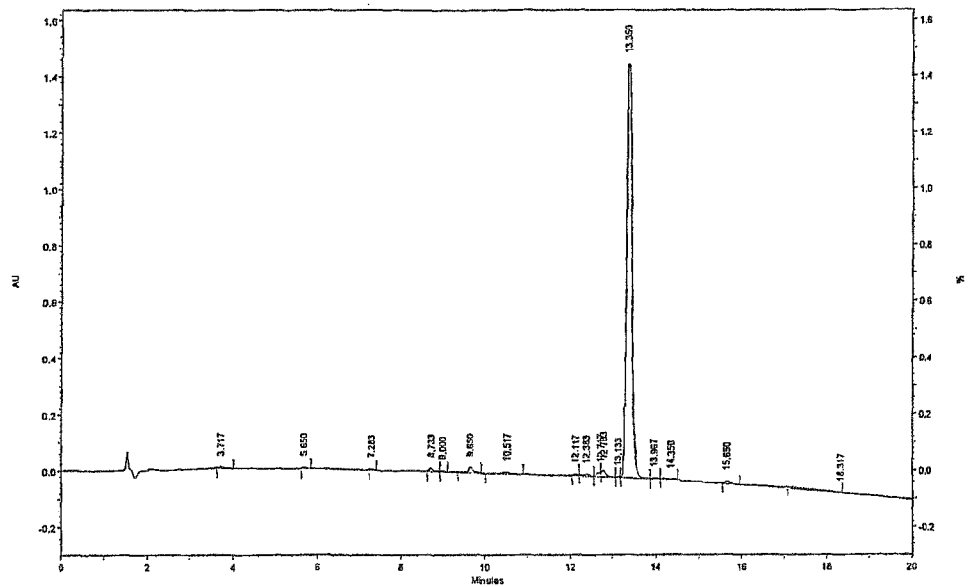
FIG. 1 represents the HPLC chromatogram of the protected pentapeptide (1) of Example 5.

ACN acetonitrile
AcOH acetic acid

BOP benzotriazol-1-yloxy-tris(dimethylamino)phosphonium hexafluorophosphate
TLC thin-layer chromatography
CMA mixture of chloroform, methanol and acetic acid
HPLC high performance liquid chromatography
DBU 1,8-diazabicyclo[5.4.0]undecen-7-ene
DCM dichloromethane
DEA diethylamine
DIC diisopropylcarbodiimide
DIEA diisopropylethylamine
$DiOC_6$ 3.3'-dihexyloxacarbocyanine iodide
DMAP 4-dimethyl aminopyridine
DMF dimethylformamide
EDC 1-ethyl-3-(3-dimethylaminopropyl)carbodiimide methiodide
HATU O-(7-azabenzotriazol-1-yl)-1,1,3,3-tetramethyluranium hexafluorophosphate
HOAt 7-azabenzotriazole
HoBt 1-hydroxybenzotriazole
IpOH isopropanol
NMM N-methyl morpholine
OAll —O-allyl
OMtt —O-methyltrityl
TFA trifluoroacetic acid

EXPERIMENTAL PART

Example 1

Synthesis of Protected and Deprotected Pentapeptides

I—Protected Pentapeptide L44' and Deprotected Pentapeptide L44

The deprotected pentapeptide L44 corresponds to the following formula:

H-Ahx-(D)Pro-Tyr-Tyr-Ahx-OH    (SEQ ID NO: 3)

1) Preparation of the Protected Pentapeptide Boc-Ahx-(D)Pro-Tyr(tBu)-Tyr (tBu)-Ahx-OH (SEQ ID NO: 8) (L44')

1.4 g (1 eq.) of 2-chlorotritylchloride resin (R1-A) (1.3 mmol/g) is placed in a syringe and washed twice under stirring with distilled DCM. A solution of 1.3 g (2 eq.) of Fmoc-6-aminocaproic acid and 1.9 ml (6 eq.) of DIEA in DCM is then added to the resin. After stirring for three hours, the mixture is filtered and washed with DCM. The resin is then placed in methanol to swell for an hour under stirring, after which it is filtered and washed with DMF, IpOH, DCM, ether. R-2A is obtained after drying.

R-2A obtained previously is placed under stirring in a 25% piperidine/DMF solution for 20 minutes. The resin is then filtered in order to produce R3-A and the solution is collected. A UV test of the collected solution makes it possible to determine the substitution of the resin R-2A (0.6 mmol/g).

General Procedure for the Coupling of an Amino Acid:

A solution of 5 eq. of Fmoc-Xaa-OH, 5 eq. of BOP and 5 eq. of HoBt in DMF is added to 1 eq. of resin R2-A. 15 eq. of DIEA are then added to the system, then the mixture is stirred for 30 minutes. This operation is repeated a second time. The coupling is verified by a ninhydrin test. Deprotection of the Fmoc group is carried out in a 25% piperidine/DMF solution under stirring for 30 minutes. A second coupling can be carried out again.

The resin R-4B is obtained after the incorporation of the different desired amino acids for synthesizing the peptide.

A mixture of 1,1,1,3,3,3-hexafluoro-2-propanol and DCM (60/40) is added to the resin R4-B. The syringe is stirred for 2 hours then filtered and rinsed several times with DCM. This operation is repeated a second time. The solutions are combined and evaporated in order to produce the protected peptide L44'.

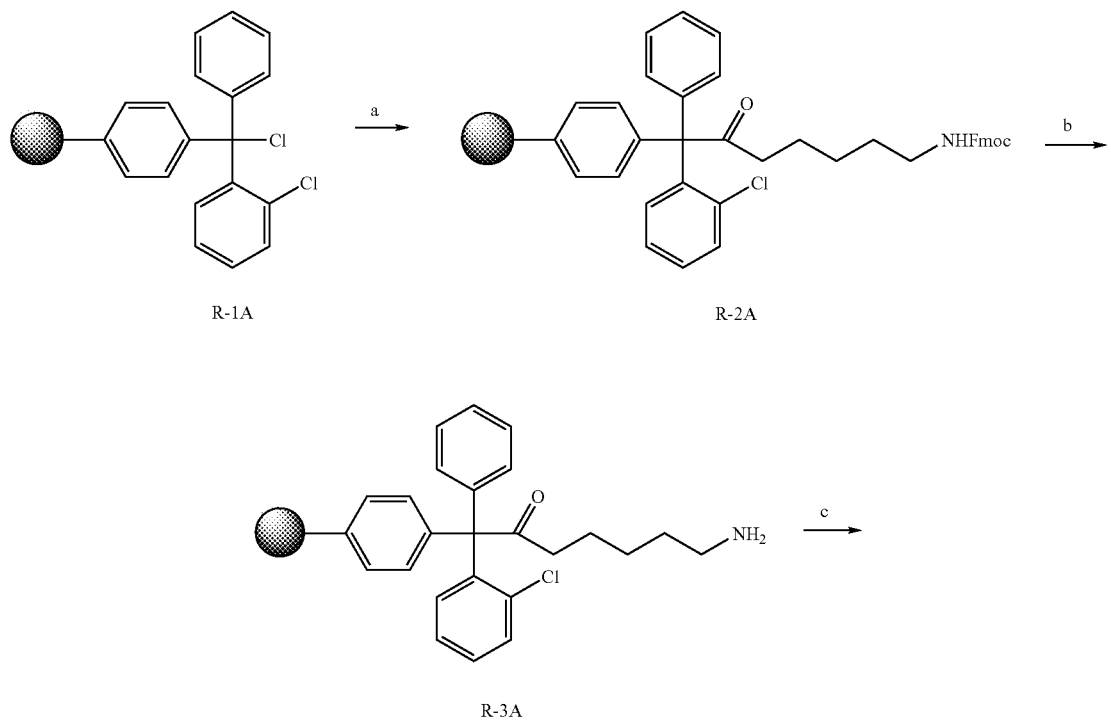

R-1A

R-2A

R-3A

-continued

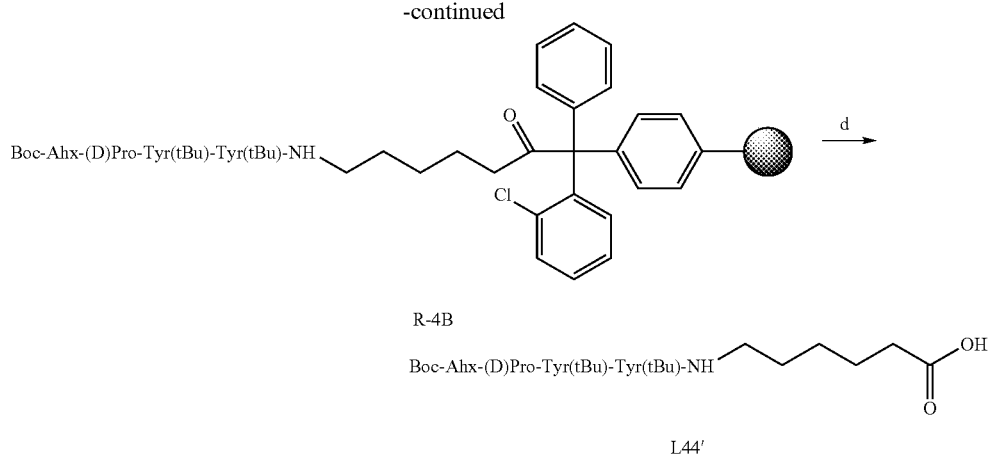

R-4B

Boc-Ahx-(D)Pro-Tyr(tBu)-Tyr(tBu)-NH~~~~~~COOH

L44' a) Fmoc-6-aminocaproic acid, DIEA, DCM; b) 25% piperidine/DMF;
c) Fmoc-Xaa-OH, BOP, HoBt, DIEA, DMF; d) 1,1,1,3,3,3-hexafluoro-2-propanol
dichloromethane (DCM) (60/40)

The peptide L44' is characterized by:

HPLC: $t_R$ 14.909 min (linear gradient, 30-100% B, 20 min)

MALDI-TOF: calculated for $C_{48}H_{73}N_5O_{10}Na$ [M+Na$^+$]: 903.12; observed: 902.57.

2) Preparation of the Deprotected Pentapeptide L44: NH$_2$-Ahx-(D)Pro-Tyr-Tyr-Ahx-OH (SEQ ID NO: 3)

The peptide L44' is treated with TFA in the presence of water. After stirring for 30 minutes, the solution is precipitated from ether, filtered and lyophilized in order to produce L44.

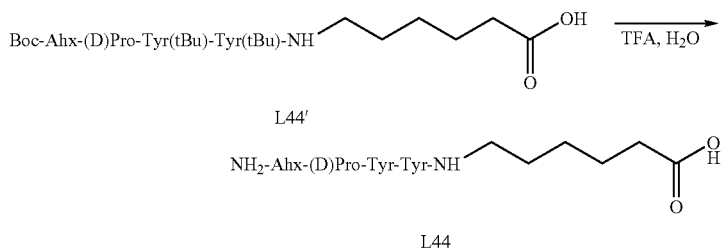

L44

This peptide L 44 is characterized by:

HPLC: $t_R$ 10.272 min (linear gradient, 5-65% B, 20 min)

MALDI-TOF: calculated for $C_{35}H_{50}N_5O_8$ [M+H$^+$]: 667.8; observed: 668.2; calculated for $C_{35}H_{49}N_5O_8Na$ [M+Na$^+$]: 690.8; observed: 690.23.

II—Protected Pentapeptide L37' and Deprotected Pentapeptide L37

The deprotected pentapeptide L37 corresponds to the following formula:

```
H-Lys-(D)Pro-Tyr-Tyr-Ahx-OH    (SEQ ID NO: 2)
```

1) Preparation of the Protected Pentapeptide L37': Boc-Lys(Boc)-(D)Pro-Tyr(tBu)-Tyr(tBu)-Ahx-OH (SEQ ID NO: 9)

1.4 g (1 eq.) of 2-chlorotritylchloride resin (R1-A) (1.3 mmol/g) is placed in a syringe and washed twice under stirring with distilled DCM. A solution of 1.3 g (2 eq.) of Fmoc-6-aminocaproic acid and 1.9 ml (6 eq.) of DIEA in DCM is then added to the resin. After stirring for three hours, the mixture is filtered and washed with DCM. The resin is then placed in methanol to swell for an hour under stirring, after which it is filtered and washed with DMF, IpOH, DCM, ether. R-2A is obtained after drying.

R-2A obtained previously is placed under stirring in a 25% piperidine/DMF solution for 20 minutes. The resin is then filtered in order to produce R3-A and the solution is collected.

A UV test of the collected solution makes it possible to determine the substitution of the resin R-2A (0.6 mmol/g).

General Procedure for the Coupling of an Amino Acid:

A solution of 5 eq. of FmocXaaOH, 5 eq. of BOP, and 5 eq. of HoBt in DMF is added to 1 eq. of resin R2-A. 15 eq. of DIEA is then added to the system, then the mixture is stirred for 30 minutes. This operation is repeated a second time. The coupling is verified by a ninhydrin test. Deprotection of the Fmoc group is carried out in a 25% piperidine/DMF solution under stirring for 30 minutes. A second coupling can be carried out again.

The resin R-4A is obtained after the incorporation of the different desired amino acids for synthesizing the peptide.

A mixture of 1,1,1,3,3,3-hexafluoro-2-propanol and DCM (60/40) is added to the resin R4-A. The syringe is stirred for 2 hours then filtered and rinsed several times with DCM. This operation is repeated a second time. The solutions are combined and evaporated in order to produce the peptide L37'.

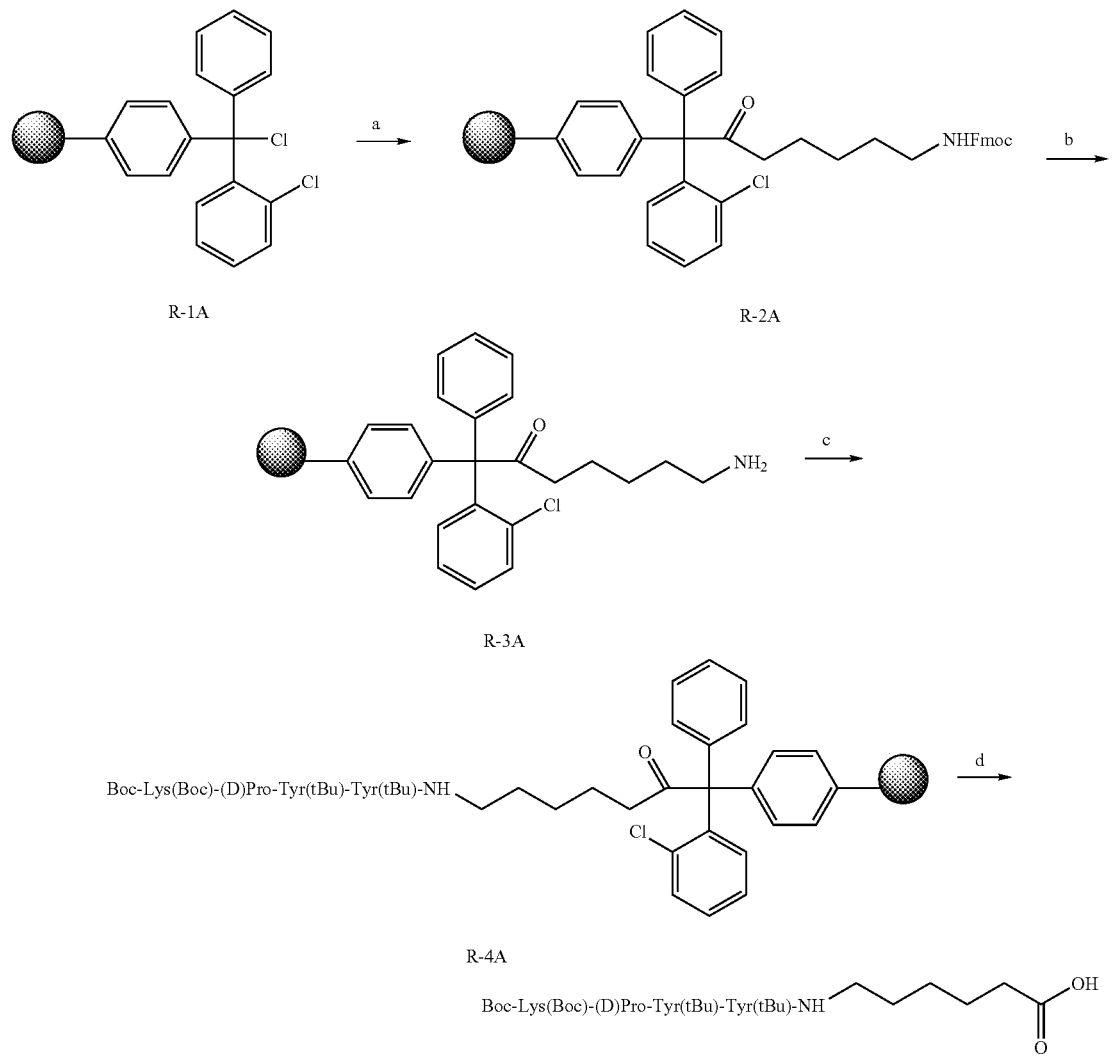

R-1A
R-2A
R-3A
R-4A
L37' a) Fmoc-6-aminocaproic acid, DIEA, DCM; b) 25% piperidine/DMF;
c) Fmoc-Xaa-OH, BOP, HoBt, DIEA, DMF; d) 1,1,1,3,3,3-hexafluoro-2-propanol
dichloromethane (DCM) (60/40)

The peptide L37' is characterized by:

HPLC: $t_R$ 15.605 min (linear gradient, 30-100% B, 20 min)

MALDI-TOF: calculated for $C_{53}H_{82}N_6O_{12}Na^+$ [M+Na$^+$]: 1018.25; observed: 1018.40; calculated for $C_{53}H_{82}N_6O_{12}K^+$ [M+K$^+$]: 1034.25; observed: 1034.64.

2) Preparation of the Deprotected Pentapeptide L37: NH$_2$-Lys-(D)Pro-Tyr-Tyr-Ahx-OH (SEQ ID NO: 2)

The peptide L37' is treated with TFA in the presence of water. After stirring for 30 minutes, the solution is precipitated from ether, filtered and lyophilized in order to produce L37.

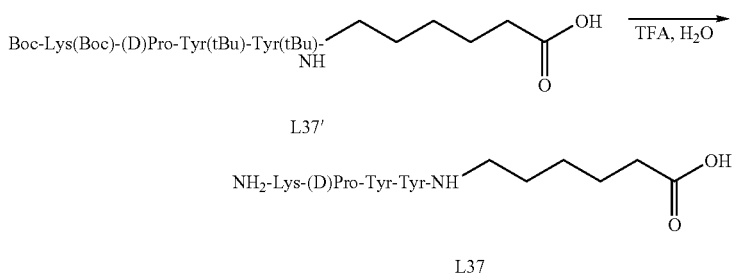

L37'

L37

This peptide L37 is characterized by:
HPLC: $t_R$ 9.065 min (linear gradient, 5-65% B, 20 min)
MALDI-TOF: calculated for $C_{35}H_{51}N_6O_8$ [M+H$^{+}$]: 683.81; observed: 682.91; calculated for $C_{35}H_{50}N_6O_8Na$ [M+Na$^{+}$]: 705.81; observed: 705.22; calculated for $C_{35}H_{50}N_6O_8K^{+}$ [M+K$^{+}$]: 721.81; observed: 721.67.

The deprotected pentapeptide L45 is synthesized according to the same protocol as that used for the synthesis of L37 and L44.

III—Protected Pentapeptide L63' and Deprotected Pentapeptide L63

The deprotected pentapeptide L63 corresponds to the following formula:

H-Lys-ψ(CH₂N)DPro-Tyr-Tyr-Ahx-OH    (SEQ ID NO: 4)

1) Preparation of the Protected Pentapeptide Boc-Lys(Boc)ψ(CH₂N)$_D$Pro-Tyr(tBu)-Tyr(tBu)-Ahx-OH (SEQ ID NO: 11) (L63')

0.3 g (1 eq.) of 2-chlorotritylchloride resin (R1-A) (1.6 mmol/g) is placed in a syringe and washed twice under stirring with distilled DCM. A solution of 340 mg (2 eq.) of Fmoc-6-aminocaproic acid and 478 µl (6 eq.) of DIEA in DCM is then added to the resin. After stirring for three hours, the mixture is filtered and washed with DCM. The resin is then placed in methanol to swell for an hour under stirring, after which it is filtered and washed with DMF, IpOH, DCM, ether. R-2A is obtained after drying.

R-2A obtained previously is placed under stirring in a 25% piperidine/DMF solution for 20 minutes. The resin is then filtered in order to produce R3-A and the solution is collected. A UV test of the collected solution makes it possible to determine the substitution of the resin R-2A (0.44 mmol/g).

General Procedure for the Coupling of an Amino Acid:

A solution of 5 eq. of Fmoc-Xaa-OH, 5 eq. of BOP, and of 5 eq. of HoBt in DMF is added to 1 eq. of resin R2-A. 15 eq. of DIEA are then added to the system, then the mixture is stirred for 30 minutes. This operation is repeated a second time. The coupling is verified by a ninhydrin test. Deprotection of the Fmoc group is carried out in a 25% piperidine/DMF solution under stirring for 30 minutes. A second coupling can be carried out again.

The resin R-4C is obtained after the incorporation of the D-Proline residue.

A solution of Boc-Lys(Boc)-H (3 eq) in DMF is added to 1 eq of resin R-4C. NaBH₃CN solubilized in DMF is then added to the system, then the mixture is stirred for 1 hour. This operation is repeated a second time. The coupling is verified by a ninhydrin test. The resin R-4D is obtained.

A mixture of 1,1,1,3,3,3-hexafluoro-2-propanol and DCM (60/40) is added to the resin R4-D. The syringe is stirred for 2 hours then filtered and rinsed several times with DCM. This operation is repeated a second time with DCM. The solutions are combined and evaporated in order to produce the protected peptide L63'.

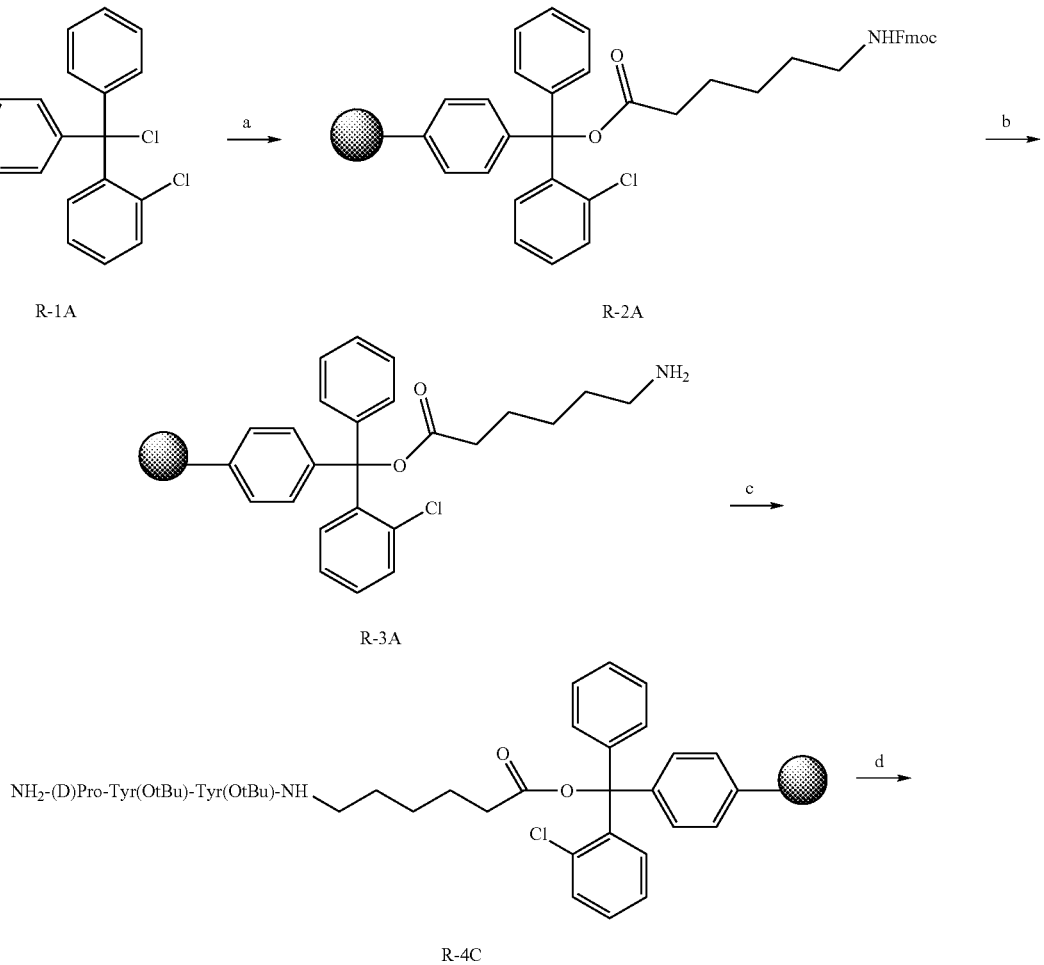

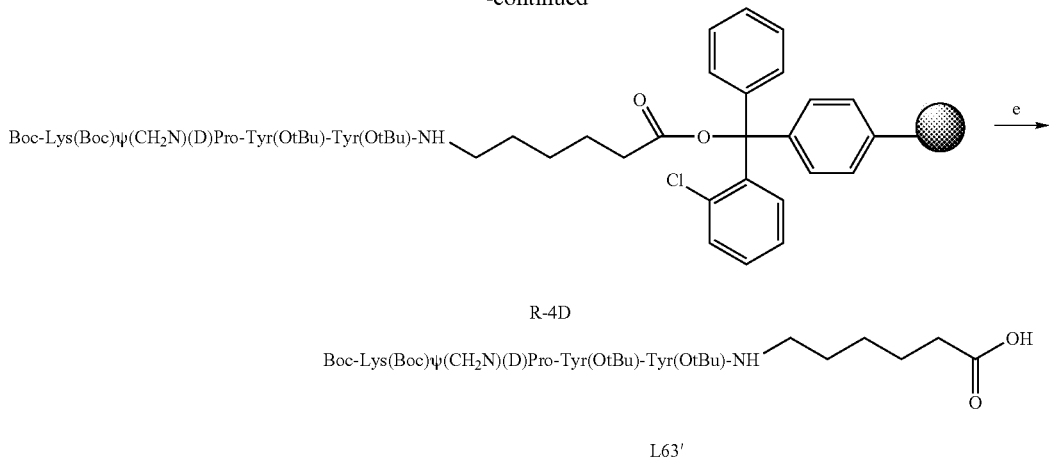

R-4D

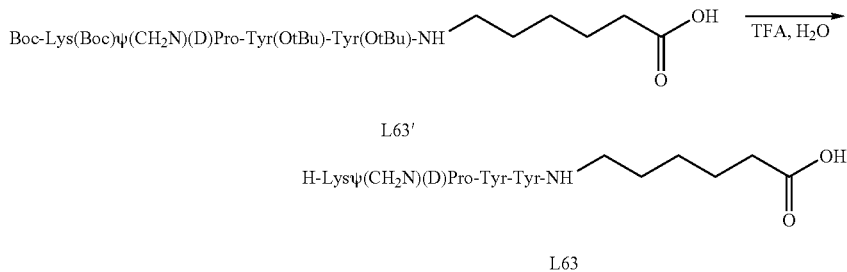

L63' a) Fmoc-6-aminocaproic acid, DIEA, DCM; b) 25% piperidine/DMF; c) Fmoc-Xaa-OH, BOP, HoBt, DIEA, DMF; d) Boc-Lys(Boc)-H, NaBH₃CN e) 1,1,1,3,3,3-hexafluoro-2-propanol/DCM (60/40)

The peptide L63' is characterized by:

HPLC: $t_R$ 13.77 min (linear gradient, 30-100% B, 20 min)

MALDI-TOF: calculated for $C_{53}H_{84}N_6O_{11}H^+$: 982.28; observed [M+H$^{+}$]=982.38; calculated for $C_{53}H_{84}N_6O_{11}Na^+$: 1004.28; observed 1004.44; calculated for $C_{53}H_{84}N_6O_{11}K^+$: 1020.28; observed 1020.45.

2) Preparation of the Protected Pentapeptide NH2-Lys ψ(CH₂N)$_D$Pro-Tyr-Tyr-Ahx-OH (SEQ ID NO: 4) (L63)

The peptide L63 is treated with TFA in the presence of water. After stirring for 30 minutes, the solution is precipitated from ether, filtered and lyophilized in order to produce L63.

ring with distilled DCM. A solution of 340 mg (2 eq.) of Fmoc-6-aminocaproic acid and 478 µl (6 eq.) of DIEA in DCM is then added to the resin. After stirring for three hours, the mixture is filtered and washed with DCM. The resin is then placed in methanol to swell for an hour under stirring, after which it is filtered and washed with DMF, IpOH, DCM, ether. R-2A is obtained after drying.

R-2A obtained previously is placed under stirring in a 25% piperidine/DMF solution for 20 minutes. The resin is then filtered in order to produce R3-A and the solution is collected. A UV test of the collected solution makes it possible to determine the substitution of the resin R-2A (0.44 mmol/g).

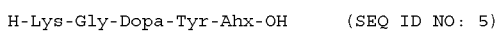

L63'

H-Lysψ(CH₂N)(D)Pro-Tyr-Tyr-NH~~~~~OH
                                      ‖
                                      O

L63

This peptide L63 is characterized by:

HPLC: $t_R$ 9.77 min (linear gradient, 5-65% B, 20 min)

MALDI-TOF: calculated for $C_{35}H_{52}N_6O_7Na^+$: 691.82; observed 689.68; calculated for $C_{35}H_{52}N_6O_7K^+$: 707.82; observed 707.15.

IV—Protected Pentapeptide L69' and Deprotected Pentapeptide L69

The deprotected pentapeptide L69 corresponds to the following formula:

```
H-Lys-Gly-Dopa-Tyr-Ahx-OH    (SEQ ID NO: 5)
```

1) Preparation of the Protected Pentapeptide Boc-Lys(Boc)-Gly-Dopa(Acetonid)-Tyr(tBu)-Ahx-OH (SEQ ID NO: 12) (L69')

0.3 mg (1 eq.) of 2-chlorotritylchloride resin (R1-A) (1.6 mmol/g) is placed in a syringe and washed twice under stir- General Procedure for the Coupling of an Amino Acid:

A solution of 5 eq. of Fmoc-Xaa-OH, 5 eq. of BOP and of 5 eq. of HoBt in DMF is added to 1 eq. of resin R2-A. 15 eq. of DIEA are then added to the system, then the mixture is stirred for 30 minutes. This operation is repeated a second time. The coupling is verified by a ninhydrin test. Deprotection of the Fmoc group is carried out in a 25% piperidine/DMF solution under stirring for 30 minutes. A second coupling can be carried out again.

The resin R-4E is obtained after the incorporation of the different desired amino acids for synthesizing the peptide.

A mixture of 1,1,1,3,3,3-hexafluoro-2-propanol and DCM (60/40) is added to the resin R4-E. The syringe is stirred for 2 hours then filtered and rinsed several times with DCM. This operation is repeated a second time with DCM. The solutions are combined and evaporated in order to produce the protected peptide L69'.

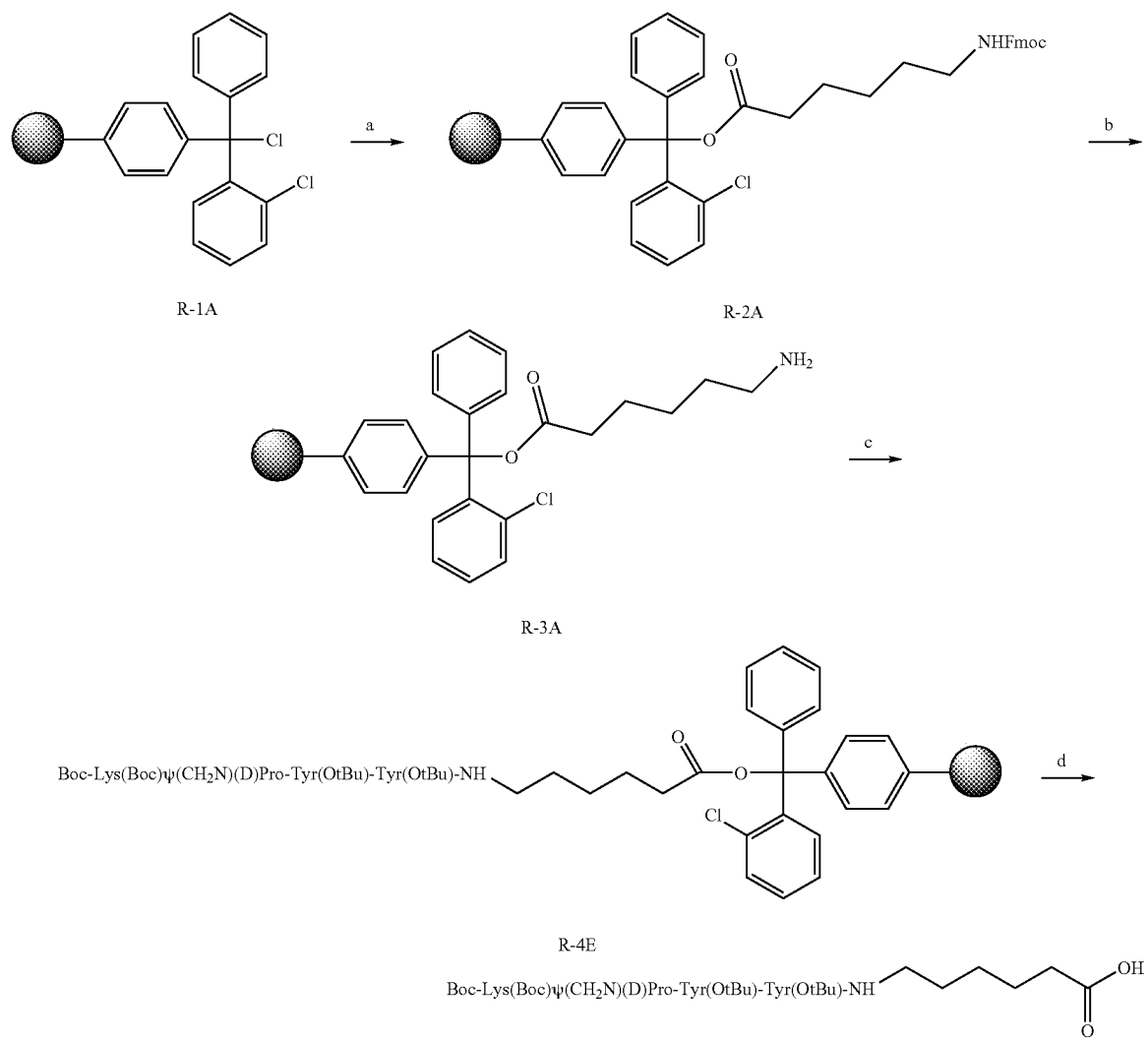

a) Fmoc-6-aminocaproic acid, DIEA, DCM; b) 25% piperidine/DMF; c) Fmoc-Xaa-OH, BOP, HoBt, DIEA, DMF; d) 1,1,1,3,3,3-hexafluoro-2-propanol/DCM (60/40)

The peptide L69' is characterized by:

HPLC: $t_R$ 12.83 min (linear gradient, 30-100% B, 20 min)

MALDI-TOF: calculated for $C_{49}H_{74}N_6O_{13}Na^+$: 978.15; observed 979.55; calculated for $C_{49}H_{74}N_6O_{13}K^+$: 994.15; observed 995.89.

2) Preparation of the Protected Pentapeptide H-Lys-Gly-Dopa-Tyr-Ahx-OH (SEQ ID NO: 5) (L69)

The peptide L69 is treated with TFA in the presence of water. After stirring for 30 minutes, the solution is precipitated from ether, filtered and lyophilized in order to produce L69.

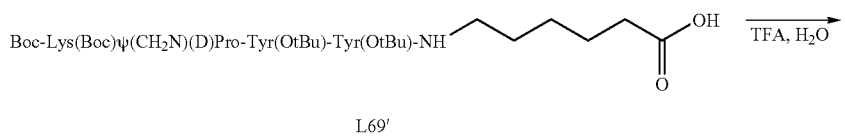

L69'

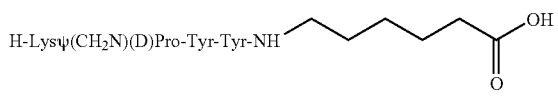

L69

This peptide L69 is characterized by:
HPLC: $t_R$ 9.18 min (linear gradient, 5-65% B, 20 min)
MALDI-TOF: calculated for $C_{32}H_{46}N_6O_9K^+$: 697.74; observed 697.40.
Example 2
Preparation of the Compound of Formula (V-b) (L36)
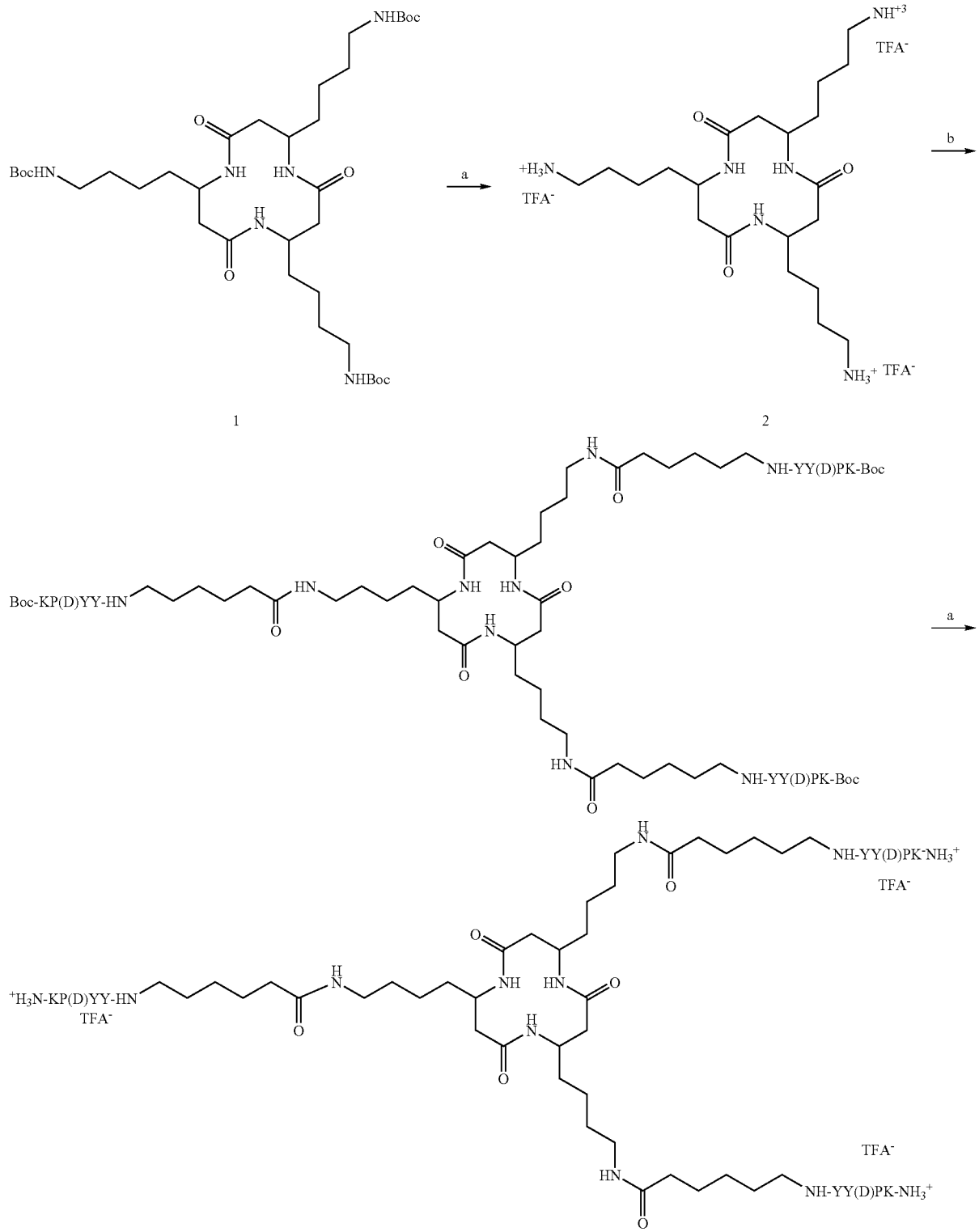
L36
a) TFA, H₂O; b) pentapeptide L37', BOP, DIEA, DMF 13 mg (1 eq.) of protected ring 1 is treated with TFA. After stirring for 30 minutes, the solution is evaporated with cyclohexane in order to produce compound 2.

Compound 2 is taken up in DMF. 56 mg (3.3 eq.) of pentapeptide L37' Boc-Lys(Boc)-(D)Pro-Tyr(tBu)-Tyr(tBu)-Ahx-OH (SEQ ID NO: 9) (see above), 25 mg (3.3 eq.) of BOP and 30 μL (10 eq.) of DIEA are added. The reaction is stirred for 25 hours at room temperature, then precipitated from NaHCO$_3$ (aq.). After filtration, the precipitate is washed successively with H$_2$O, KHSO$_4$ 1N, H$_2$O and AcOEt.

The solid formed is then treated with TFA in the presence of water. After stirring for 30 minutes, the solution is precipitated from ether and filtered in order to produce 35 mg of L36 ligand (crude reaction yield 86%). 11 mg of pure L36 is obtained after purification by RP-HPLC (yield after purification 27%).

The L36 ligand is characterized by:

HLPC: t$_R$ 10.115 min (linear gradient, 5-65% B, 20 min)

MALDI-TOF: calculated for C$_{126}$H$_{187}$N$_{24}$O$_{24}$ [M+H$^+$]: 2422; observed: 2420.68.

Example 3

Preparation of the Macrocycle for L40 and L43

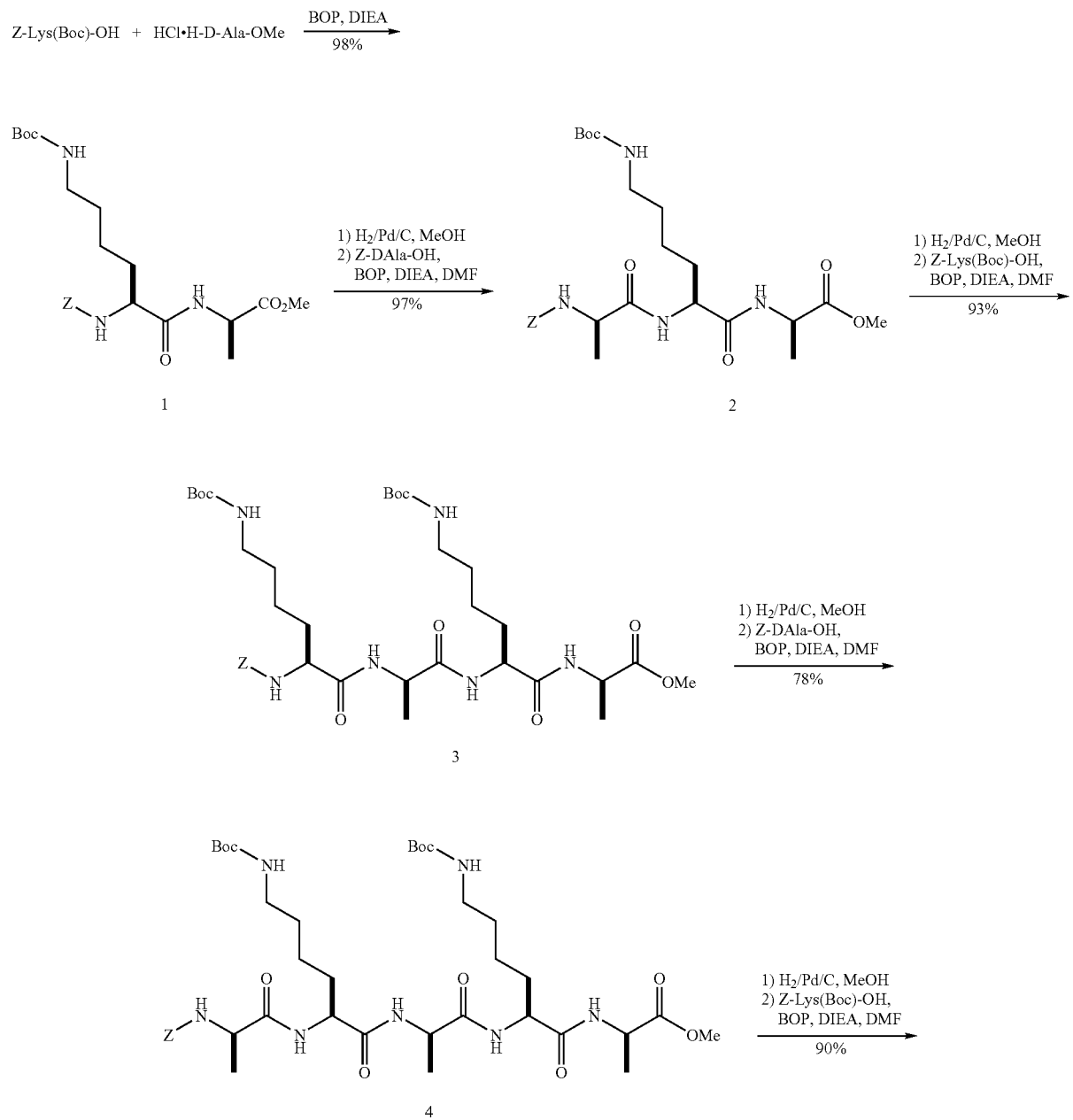

-continued
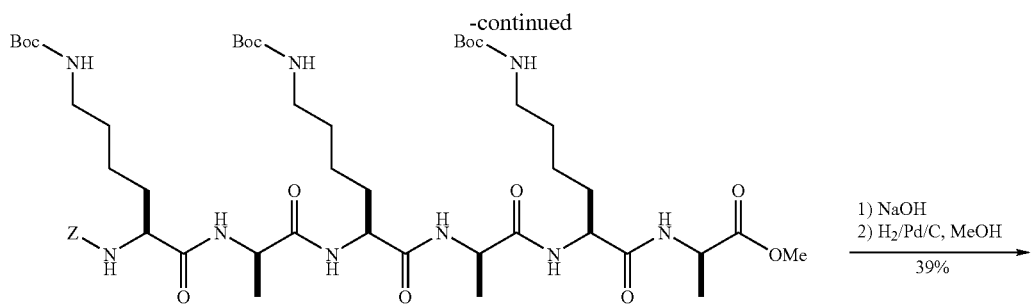
5
1) NaOH
2) H₂/Pd/C, MeOH
———————
39%
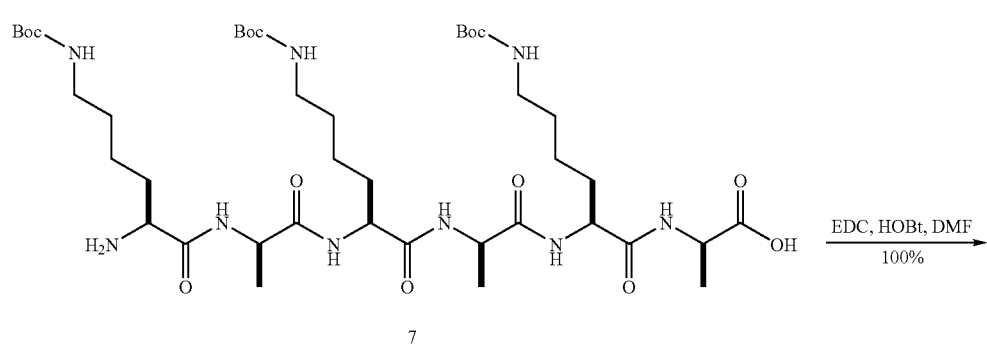
7
EDC, HOBt, DMF
———————
100%
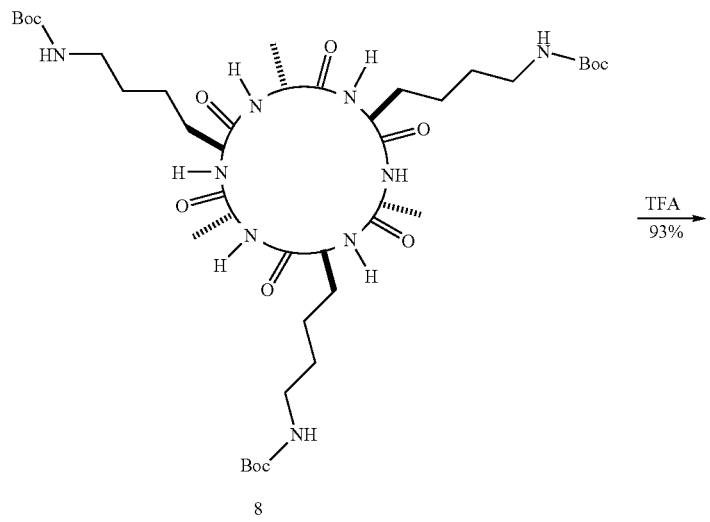
8
TFA
———
93%
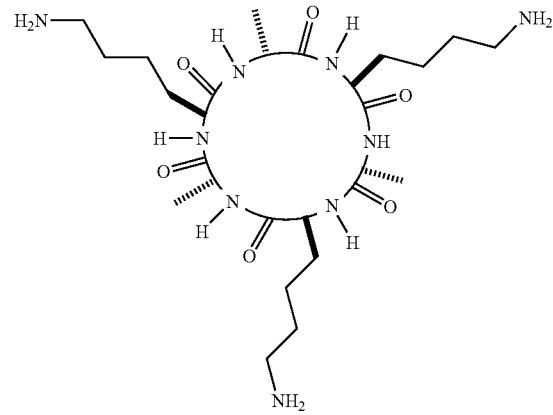
9

Compound 1

Z-Lys(Boc)-OH (5.99 g; 15.75 mmol) was dissolved in DMF (50 ml) containing HCl, H$_2$N-(D)Ala-OMe (2.09 g; 15 mmol), BOP (6.96 g; 15.75 mmol) and DIEA (7.6 ml; 45 mmol) was added to this solution. The reaction mixture is stirred for 2 hours at room temperature. Then a saturated solution of sodium bicarbonate (500 ml) is added under stirring, then ethyl acetate (200 ml) is added. The organic phase is washed with a saturated solution of sodium bicarbonate (2×100 ml), water (2×100 ml), a 1 M aqueous solution of potassium hydrogen sulphate (2×100 ml), water, brine (1×100 ml), the mixture is dried over sodium sulphate and concentrated under vacuum in order to obtain a white solid. Yield: 98% (6.85 g); HPLC: $t_R$=9.3 min, purity >97%, 30-100 over 20 min.

Compound 2

Compound 1 (4.66 g; 10 mmol) is dissolved in MeOH (100 ml) with HCl (10 mmol) at room temperature and hydrogenated in the presence of a 10% Pd/C catalyst. After 3 hours, the catalyst is removed by filtration and the filtrate is concentrated under vacuum in order to obtain a white solid. Yield: 100% (3.71 g), purity HPLC >97%, TLC Rf 0.3 CMA 60/10/5.

The HCl salt (3.68 g; 10 mmol) is dissolved in DMF (20 ml) containing Z-(D)Ala-OH (2.34 g; 10.5 mmol) and BOP (4.64 g; 10.5 mmol). DIEA (3.4 ml; 20 mmol) is added to this solution and the reaction mixture is stirred for 4 hours at room temperature. Then, a saturated solution of sodium bicarbonate (500 ml) is added under stirring, then ethyl acetate (200 ml) is added. The organic phase is washed with a saturated solution of sodium bicarbonate (2×100 ml), water (2×100 ml), a 1 M aqueous solution of potassium hydrogen sulphate (2×100 ml), water, brine (1×100 ml), the mixture is dried over sodium sulphate and concentrated under vacuum in order to obtain a white solid. Yield: 97% (5.2 g); HPLC: $t_R$=8.9 min, purity >88%, 30-100 over 20 min.

Compound 3

Compound 2 (5.1 g; 9.5 mmol) is dissolved in MeOH (100 ml) with HCl (9.5 mmol) at room temperature and hydrogenated in the presence of a 10% Pd/C catalyst. After 3 hours, the catalyst is removed by filtration and the filtrate is concentrated under vacuum. The expected HCl salt is crystallized from ether and dried under vacuum over KOH. Yield: 100% (4.2 g).

The HCl salt (4.2 g; 9.5 mmol) is dissolved in DMF (20 ml) containing Z-Lys(Boc)-OH (3.8 g; 10.5 mmol) and BOP (4.42 g; 10 mmol). DIEA (4.2 ml; 25 mmol) is added to this solution and the reaction mixture is stirred overnight at room temperature. Then, a saturated solution of sodium bicarbonate (500 ml) is added under stirring, then ethyl acetate (200 ml) is added. The organic phase is washed with a saturated solution of sodium bicarbonate (2×100 ml), water (2×100 ml), a 1 M aqueous solution of potassium hydrogen sulphate (2×100 ml), water, brine (1×100 ml), the mixture is dried over sodium sulphate and concentrated under vacuum to leave a residue which solidifies during triturarion in hexane. It is collected, washed with hexane, diisopropyl ether and dried under vacuum over KOH. Yield: 93% (6.8 g); HPLC: $t_R$=10.9 min, purity 90%, 30-100 over 20 min.

Compound 4

Compound 3 (6.8 g; 8.9 mmol) is dissolved in MeOH (100 ml) with HCl (8.9 mmol) at room temperature and hydrogenated in the presence of a 10% Pd/C catalyst. After 3 hours, the catalyst is removed by filtration and the filtrate is concentrated under vacuum in order to produce a white solid. Yield: 91% (5.4 g); TLC Rf 0.3 CMA 60/10/5.

The HCl salt (5.4 g; 8.1 mmol) is dissolved in DMF (25 ml) containing Z-(D)Ala-OH (1.9 g; 8.5 mmol) and BOP (3.8 g; 8.5 mmol). DIEA (4.2 ml; 25 mmol) is added to this solution and the reaction mixture is stirred for 6 hours at room temperature. Then, a saturated solution of sodium bicarbonate (500 ml) is added under stirring, then ethyl acetate (200 ml) is added. The organic phase is washed with a saturated solution of sodium bicarbonate (2×100 ml), water (2×100 ml), a 1 M aqueous solution of potassium hydrogen sulphate (2×100 ml), water, brine (1×100 ml), the mixture is dried over sodium sulphate and concentrated under vacuum to leave a residue which solidifies during triturarion in hexane. It is collected, washed with hexane, diisopropyl ether and dried under vacuum over KOH. Yield: 78% (5.3 g); HPLC: $t_R$=10.67 min, purity 77%, 30-100 over 20 min.

Compound 5

Compound 4 (5.3 g; 6.3 mmol) is dissolved in MeOH (100 ml) with HCl (6.3 mmol) at room temperature and hydrogenated in the presence of a 10% Pd/C catalyst. After 5 hours, the catalyst is removed by filtration and the filtrate is concentrated under vacuum. The expected HCl salt is crystallized from ether and dried under vacuum over KOH. Yield: 91% (4.7 g).

The HCl salt (4.7 g; 5.5 mmol) is dissolved in DMF (20 ml) containing Z-Lys(Boc)-OH (2.2 g; 5.8 mmol) and BOP (2.56 g; 5.8 mmol). DIEA (1.9 ml; 11 mmol) is added to this solution and the reaction mixture is stirred overnight at room temperature. Then, a saturated solution of sodium bicarbonate (500 ml) is added under stirring, then ethyl acetate (200 ml) is added. The organic phase is washed with a saturated solution of sodium bicarbonate (2×100 ml), water (2×100 ml), a 1 M aqueous solution of potassium hydrogen sulphate (2×100 ml), water, brine (1×100 ml), the mixture is dried over sodium sulphate and concentrated under vacuum to leave a residue which solidifies during triturarion in hexane. It is collected, washed with hexane, diisopropyl ether and dried under vacuum over KOH. Yield: 90% (5.3 g); HPLC: $t_R$=12.26 min, purity 60%, 30-100 over 20 min.

Compound 6

Compound 5 (5.3 g; 4.9 mmol) is dissolved in acetone (20 ml) and 1N NaOH soda (5.9 mmol) is added at 0° C. The reaction mixture is maintained at 0° C. for 1 hour before allowing it to warm to room temperature. After 6 hours, the reaction mixture is concentrated under vacuum. Then, ethyl acetate (100 ml) is added under stirring, then a 1 N aqueous solution of potassium hydrogen sulphate (2×100 ml), water, brine (1×100 ml), the mixture is dried over sodium sulphate and concentrated under vacuum to leave a residue which solidifies during triturarion in diisopropyl ether. It is collected, washed with diisopropyl ether and dried under vacuum over KOH. The crude peptide is purified by chromatography on a silica gel column using CMA 120/10/5. Yield: 44% (2.3 g); HPLC: $t_R$=11.28 min, purity 78%, 30-100 over 20 min.

Compound 7

Compound 6 (1.5 g; 1.46 mmol) is dissolved in MeOH (10 ml) at room temperature and hydrogenated in the presence of a 10% Pd/C catalyst. After 4 hours, the catalyst is removed by filtration and the filtrate is concentrated under vacuum. The expected HCl salt is crystallized from diisopropyl ether and dried under vacuum over KOH. Yield: 88% (1.17 g); HPLC: $t_R$=16.9 min, purity 70%, 5-65 over 20 minutes.

Compound 8

Compound 7 (800 mg; 0.87 mmol) is dissolved in DMF (80 ml) at room temperature containing EDC, HCl (201 mg; 1.05 mmol), HOBt (142 mg; 1.05 mmol) and DIEA (373 ml; 2.19 mmol) is added to this solution. The reaction mixture is stirred for 2 days at room temperature and the reaction mixture is concentrated under vacuum.

A saturated solution of sodium bicarbonate, then ethyl acetate (100 ml) are added under stirring. The organic phase is washed with a saturated solution of sodium bicarbonate (2×100 ml), then a 1N aqueous solution of potassium hydrogen sulphate (2×100 ml), water, brine (1×100 ml), the mixture is dried over sodium sulphate and concentrated under vacuum in order to produce a white solid. Yield: 100% (0.78 g); M+H$^+$=896.

Compound 9

Compound 8 (650 mg; 0.76 mmol) is dissolved in TFA (6 ml) for 1 hour at room temperature. The amine of the mixture is concentrated under vacuum. The expected amine is precipitated from ether (50 ml). It is collected, washed with ether and dried under vacuum. Yield: 98% (0.70 g); M+H=598.5 (calc.=597.6).

Example 4

Preparation of the Compound of Formula (III-e) (L40)

Compound L40 corresponds to the following formula:

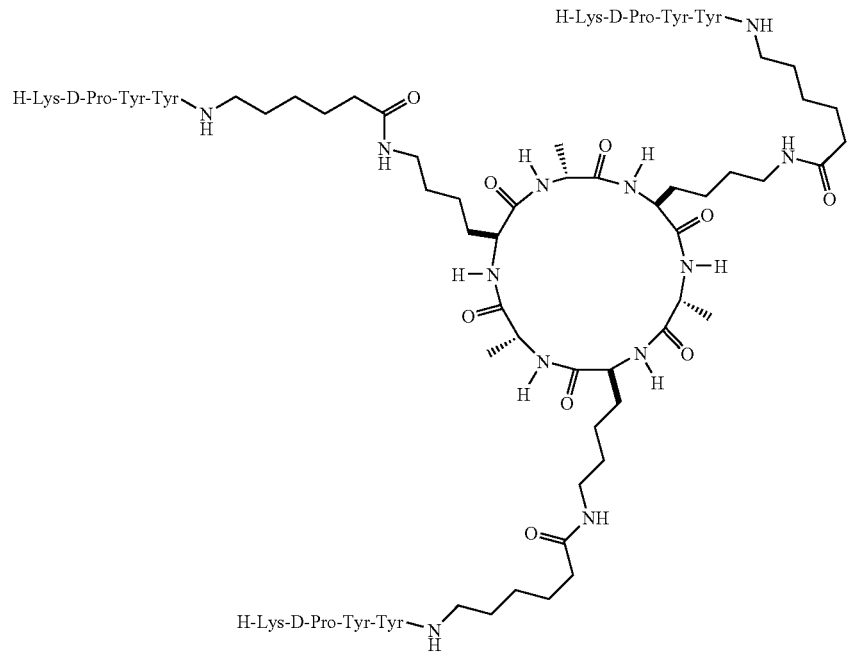

Reaction scheme

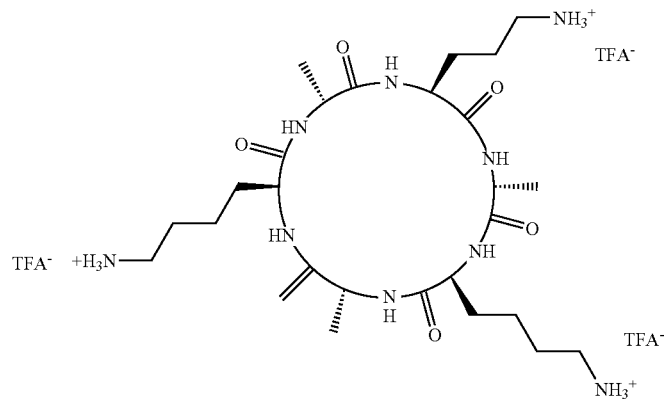

-continued

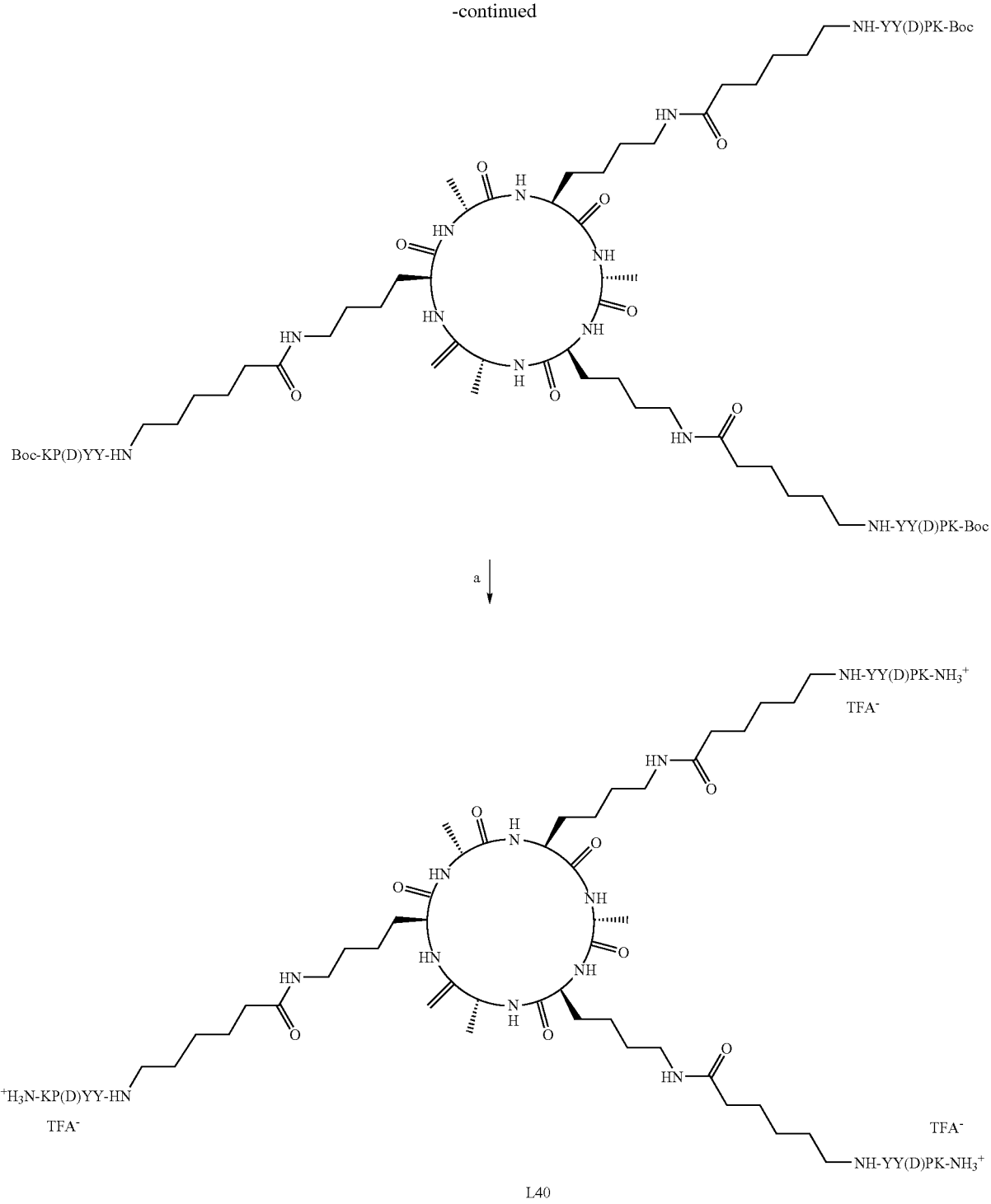

a) TFA, H₂O; b) pentapeptide L37', BOP, DIEA, DMF 35 mg (3.3 eq.) of pentapeptide Boc-Lys(Boc)-(D)Pro-Tyr (tBu)-Tyr(tBu)-Ahx-OH (SEQ ID NO: 9) (L37'), 16 mg (3.3 eq.) of BOP are added to 10 mg (1 eq.) of ring 9 in DMF (see Example 3) and 20 μL (10 eq.) of DIEA is added. The reaction mixture is stirred for 25 hours at room temperature, then precipitated from NaHCO₃ (aq.). After filtration, the precipitate is washed successively with H₂O, 1N KHSO₄, H₂O and AcOEt.

The solid formed is then treated with TFA in the presence of water. After stirring for 30 minutes, the solution is precipitated from ether and filtered in order to produce 40 mg of L40 ligand.

6 mg of pure L40 is obtained after purification by RP-HPLC (yield after purification 22%).

The L40 ligand is characterized by:
HPLC: $t_R$ 10.203 min (linear gradient, 5-65% B, 20 min)
MALDI-TOF: calculated for $C_{132}H_{196}N_{27}O_{27}$ [M+H$^+$]: 2593.16; observed: 2593.24; calculated for $C_{132}H_{195}N_{27}O_{27}Na$ [M+Na$^+$]: 2616.16; observed 2616.78.
Example 5
Preparation of the Compound of Formula (III-f) (L43)
Compound L43 corresponds to the following formula:
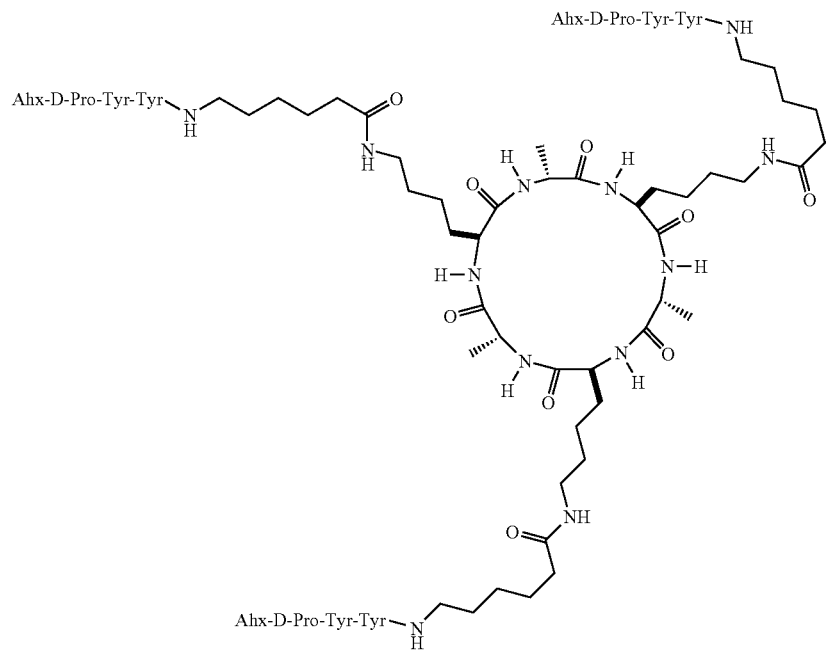
Reaction Scheme
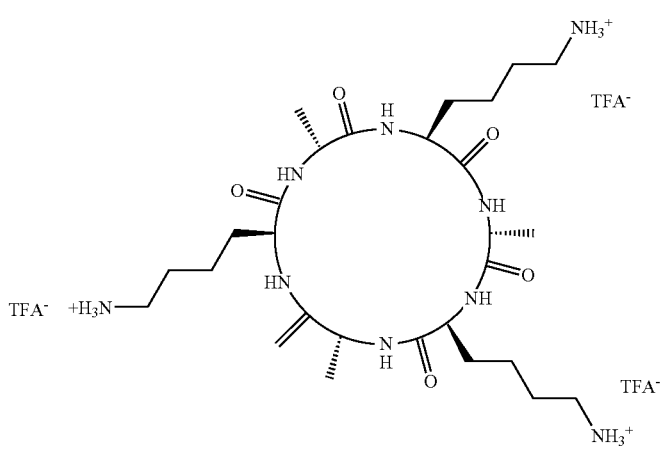

-continued

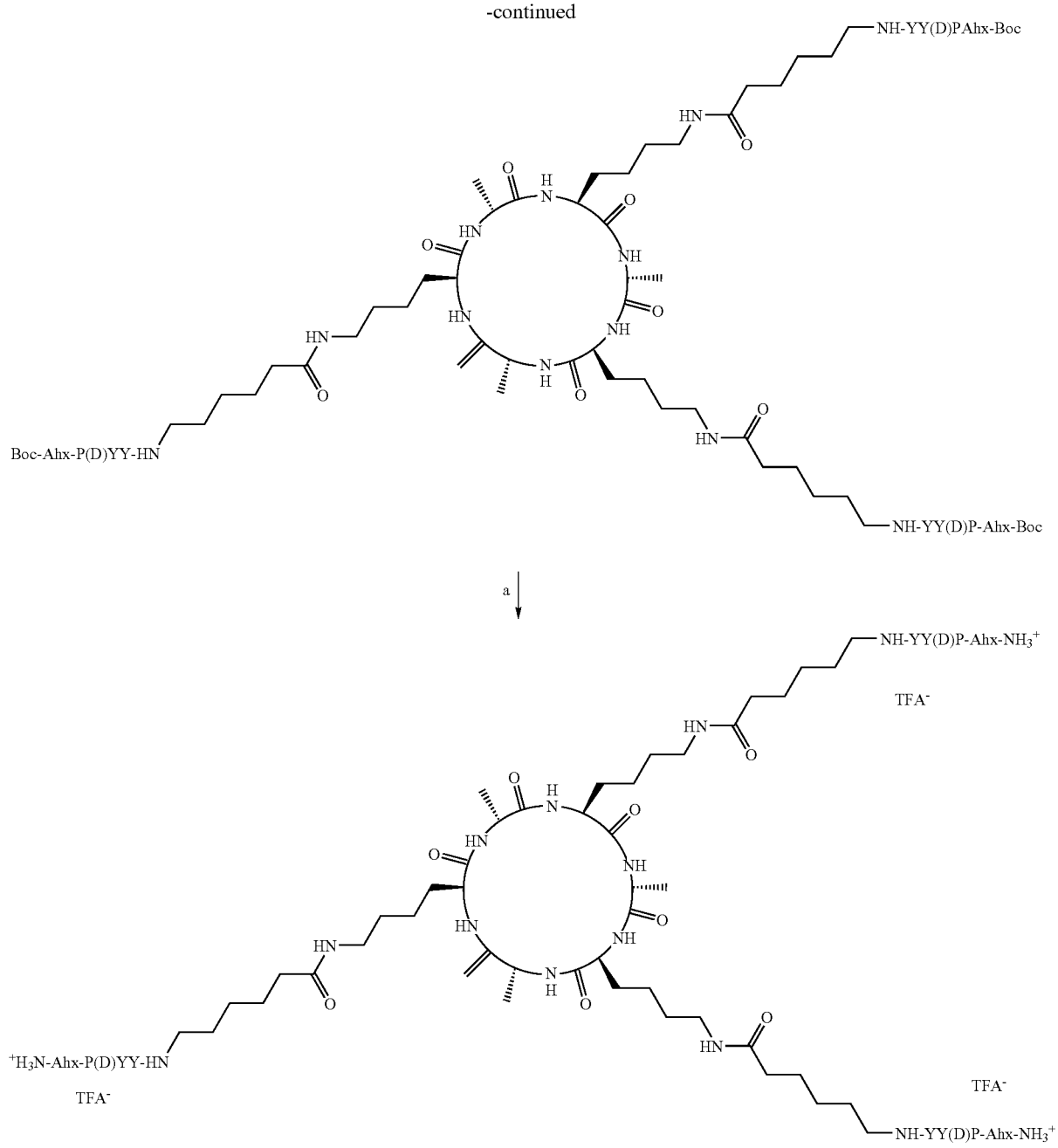

L43 a) TFA, H₂O; b) pentapeptide L44′, BOP, DIEA, DMF 35 mg (3.3 eq.) of pentapeptide Boc-Ahx-(D)Pro-Tyr(tBu)-Tyr(tBu)-Ahx-OH (SEQ ID NO: 8) (L44′), 16 mg (3.3 eq.) of BOP are added to 10 mg (1 eq.) of ring 9 in DMF (see example 3) and 20 μL (10 eq.) of DIEA is added. The reaction mixture is stirred for 25 hours at room temperature, then precipitated from NaHCO₃ (aq.). After filtration, the precipitate is washed successively with H₂O, KHSO₄ 1N, H₂O and AcOEt.

The solid formed is then treated with TFA in the presence of water. After stirring for 30 minutes, the solution is precipitated from ether and filtered in order to produce 20 mg of L43 ligand.

8 mg of pure L43 is obtained after purification by RP-HPLC (yield after purification 30%).

The L43 ligand is characterized by:

HLPC: $t_R$ 13.935 min (linear gradient, 5-65% B, 20 min)

MALDI-TOF: calculated for $C_{132}H_{193}N_{24}O_{27}$ [M+⁺]: 2548.11; observed: 2547.88; calculated for $C_{132}H_{192}N_{24}O_{27}Na^+$ [M+Na⁺]: 2571.11; observed: 2570.62; calculated for $C_{132}H_{1932}N_{24}O_{27}K^+$ [M+K⁺]: 2587.11; observed: 2586.13.

Example 6
Preparation of Compound L41
Compound L41 corresponds to the following formula:
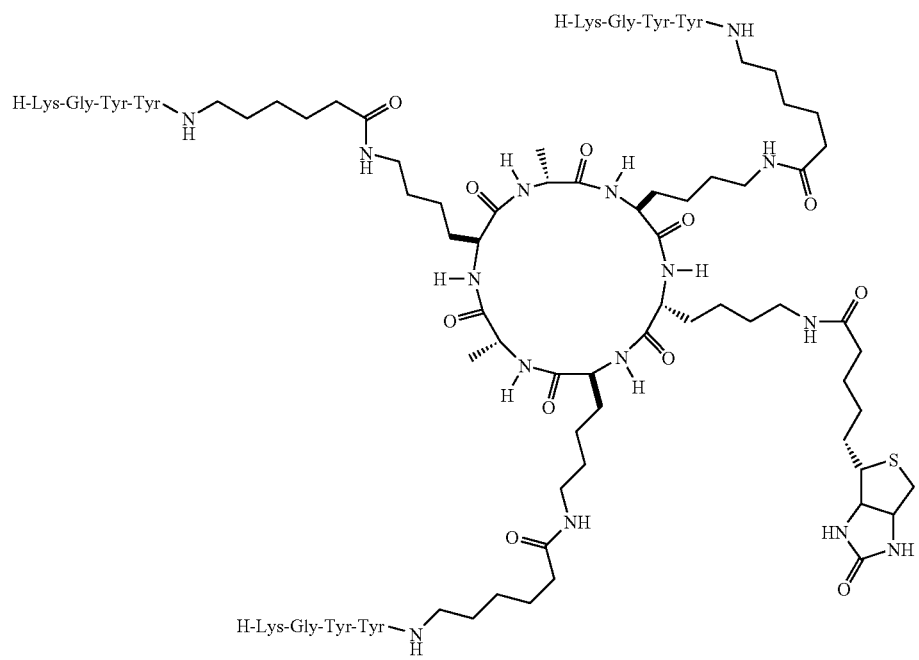
It can also be represented by the following formula:
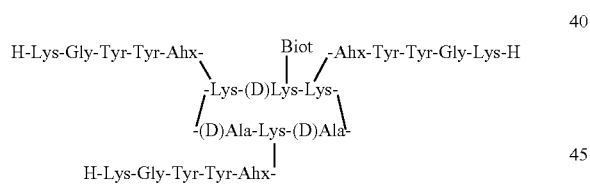
The synthesis strategy of compound A (L41) is described below. The synthesis of intermediates 1 and 2 was carried out in solid phase and the following stages were carried out in solution.
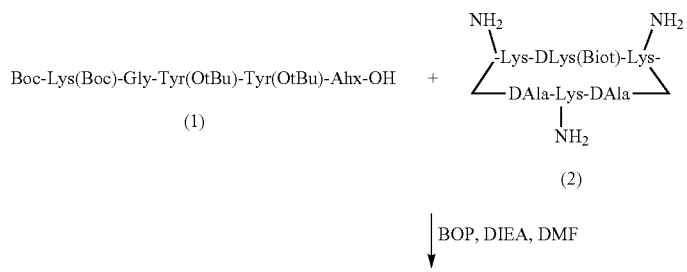

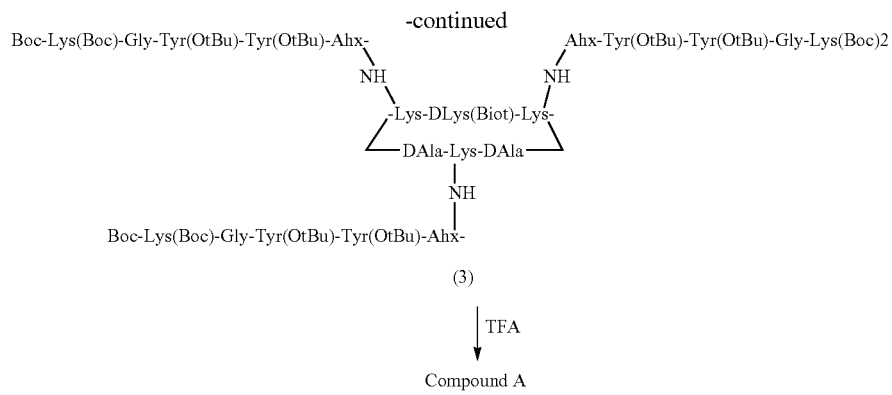

Compound A

1) Synthesis of the Pentapeptide Boc-Lys(Boc)-Gly-Tyr(OtBu)-Tyr(OtBu)-Ahx-OH (1) (SEQ ID NO: 13):

The synthesis of this peptide was carried out following a step-by-step solid-phase Fmoc strategy. The peptide was assembled on a 2-chlorotrityl resin (Senn chemicals, 1.3 mmoles/g) and the synthesis scale was 1.3 mmoles.

The coupling of the first amino acid is carried out in anhydrous dichloromethane (4 ml) with 2 equivalents of Fmoc-Ahx-OH and 6 equivalents of DIEA for 3 hours. The substitution test carried out, after washings and drying of the resin, shows a substitution level of 0.6 mmoles/g.

The coupling of the following amino acids, Fmoc-Tyr(OtBu)-OH, Fmoc-Gly-OH and Boc-Lys(Boc)-OH is carried out in DMF with 5 equivalents of amino acids in the presence of BOP/HOBt and of DIEA. A double coupling is carried out systematically.

Deprotection of the Fmoc groups is carried out using a 25% solution of piperidine in DMF for 20 minutes.

The cleavage of the peptide from the resin is carried out using a 1,1,1,3,3,3-hexafluoro-2-propanol/dichloromethane solution (60/40) for 2 hours at room temperature.

The resin is filtered and the filtrate is concentrated and dried under vacuum. The protected peptide is used directly without purification. The synthesis yield is quantitative.

The protected pentapeptide is analyzed by HPLC (column C18, Macherey Nagel, SP 250/10 nucleosil 300-7) using a water/acetonitrile/TFA mixture, a gradient of 30 to 100% B over 20 minutes (A: water, 0.1% TFA; B: acetonitrile, 0.08% TFA), a flow rate of 1.2 ml/minute and absorption at 210 nm) (FIG. 1). The purity level is 92%.

2) Synthesis of the Cyclized Hexapeptide (2):

The synthesis of the hexapeptide H-(D)Ala-Lys(Boc)-(D)Lys(Biot)-Lys(Boc)-(D)Ala-Lys(Boc)-OH (SEQ ID NO: 14) was carried out following a step-by-step solid-phase Fmoc strategy and according to the same protocol as that described for the synthesis of the pentapeptide using the following amino acids: Fmoc-Lys(Boc)-OH, Fmoc-(D)Ala-OH and Fmoc-(D)Lys(Biot)-OH (biotin-labelling). The synthesis yield is also quantitative and the peptide is used directly without any purification.

Figure 2:
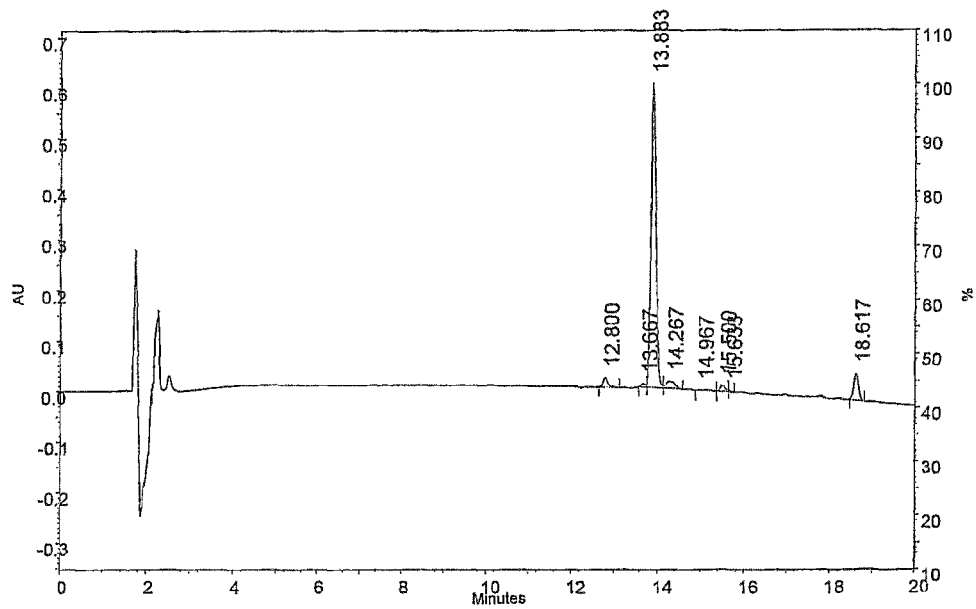
FIG. 2 represents the HPLC chromatogram of the non-cyclized hexapeptide (2) of Example 5.

The non-cyclized hexapeptide is analyzed by HPLC (column C18, Macherey Nagel, SP 250/10 nucleosil 300-7) using a water/acetonitrile/TFA mixture, a gradient of 20 to 80% B over 20 minutes (A: water, 0.1% TFA; B: acetonitrile, 0.08% TFA), a flow rate of 1.2 ml/minute and absorption at 210 nm) (FIG. 2).

The hexapeptide (660 mg; 0.55 mmol) is dissolved at room temperature in DMF (70 ml) containing EDC, HCl (127 mg; 0.66 mmol), HOBt (89 mg; 0.66 mmol) and DIEA (140 μl, 0.82 mmol). After 48 hours, the reaction medium is precipitated from a solution containing saturated NaHCO$_3$ (300 ml). The cyclized hexapeptide is then washed with a 1N KHSO$_4$ solution and a saturated solution of NaCl then dried under vacuum (540 mg; Yield: 83%).

Deprotection of the Boc groups is carried out with trifluoroacetic acid (3 ml) for 1 hour. The peptide is then precipitated by adding diethyl ether (50 ml), filtered and dried under vacuum (510 mg; Yield: 95%).

Figure 3:
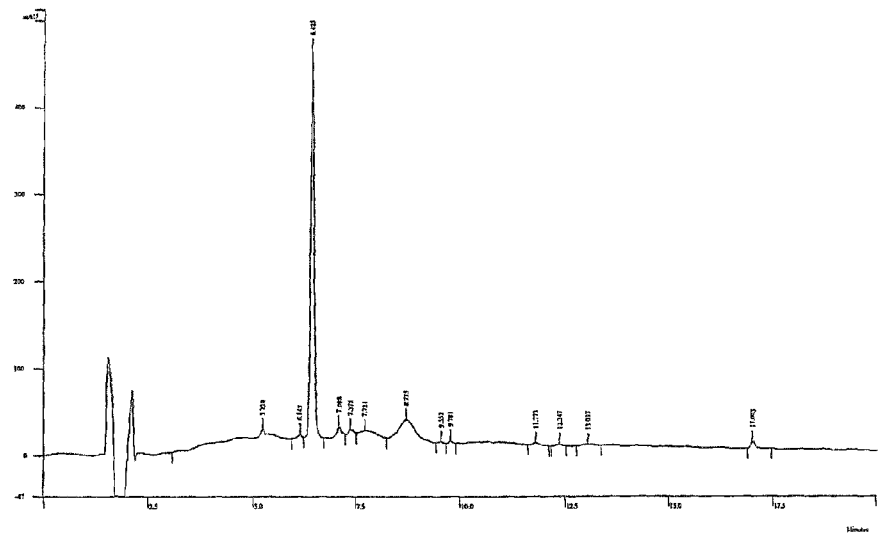
FIG. 3 represents the HPLC chromatogram of the cyclized and deprotected hexapeptide (3) of Example 5.

The cyclized and deprotected hexapeptide is analyzed by HPLC (column C18, Macherey Nagel, SP 250/10 nucleosil 300-7) using a water/acetonitrile/TFA mixture, a gradient of 5 to 65% B over 20 minutes (A: water; 0.1% TFA; B: acetonitrile; 0.08% TFA), a flow rate of 1.2 ml/minute and absorption at 210 nm) (FIG. 3).

3) Coupling of the Intermediates (1) and (2):

The cyclized and deprotected hexapeptide (2) (61 mg; 50 μmol) is dissolved at room temperature in DMF (2 ml) containing pentapeptide (1) (157 mg; 165 μmol), BOP (73 mg; 165 μmol), and DIEA (85 μl). After 48 hours, the reaction medium is precipitated from a solution containing saturated NaHCO$_3$ (300 ml). The precipitate is then washed with a 1N KHSO$_4$ solution and a saturated solution of NaCl then dried under vacuum (180 mg; Yield: 100%).

Deprotection of the Boc and tBu groups of compound (3) is carried out with trifluoroacetic acid (3 ml) for 1 hour. The peptide is then precipitated by adding diethyl ether (50 ml), filtered and dried under vacuum (160 mg before purification; Yield: 100%).

Figure 4:
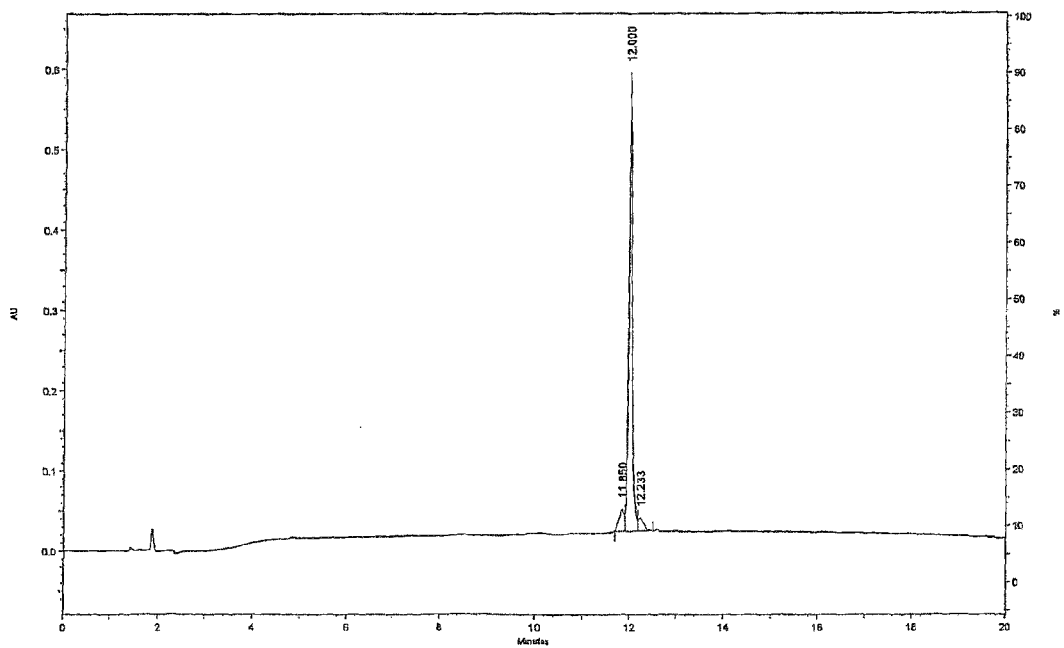
FIG. 4 represents the HPLC chromatogram of compound A of Example 5 (L41).

The peptide is then purified by reversed phase HPLC on a Perkin-Elmer preparative HPLC, on a column C18 (Macherey Nagel, SP 250/10 nucleosil 300-7) using a water/acetonitrile/TFA mixture, a gradient of 5 to 65% B over 30 minutes (A: water, 0.1% TFA; B: acetonitrile—0.08% TFA) and a flow rate of 6 ml/minute. The fractions having a purity greater than 97% are combined and lyophilized. (FIG. 4: HPLC profile of compound A after purification; purity level=97.2%).

The HPLC purification yield is 17%.

Example 7
Preparation of the Compound of Formula (III-i) (L62)
Compound L62 corresponds to the following formula:
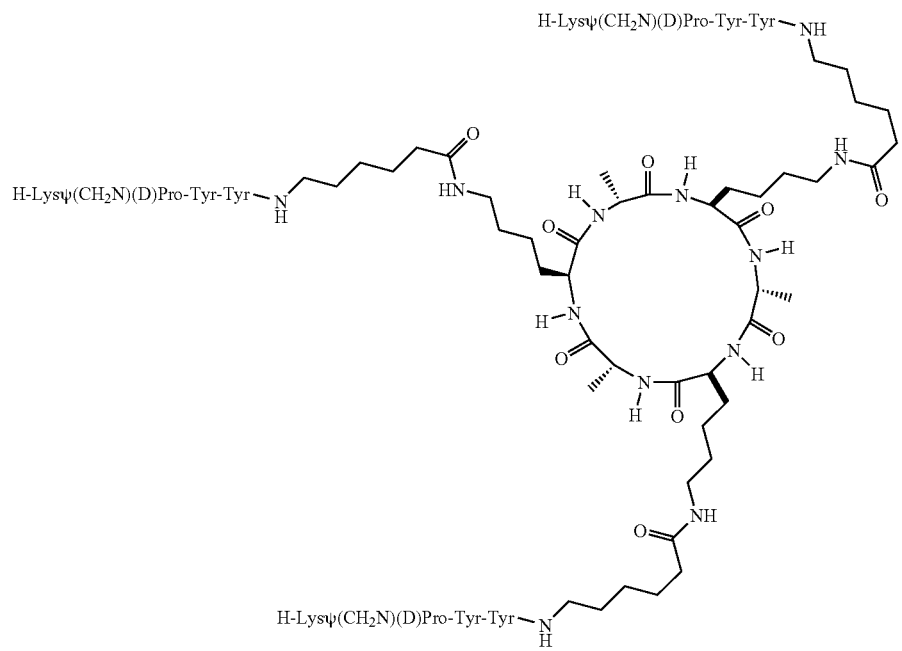
Reaction scheme
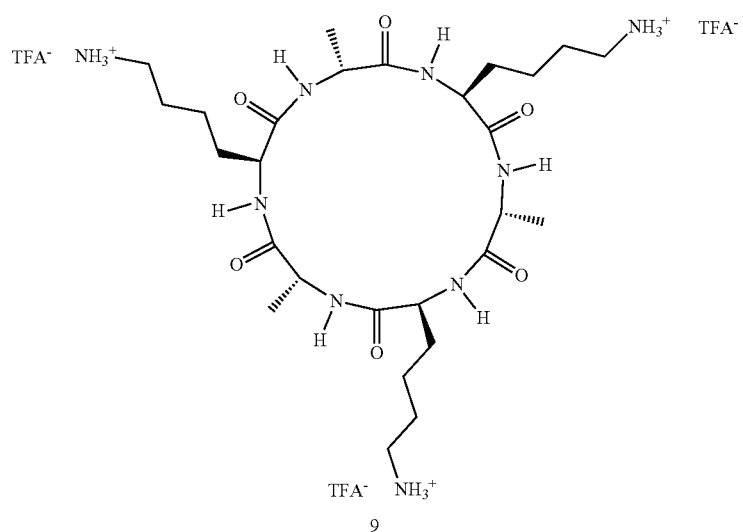
9
b ↓

-continued
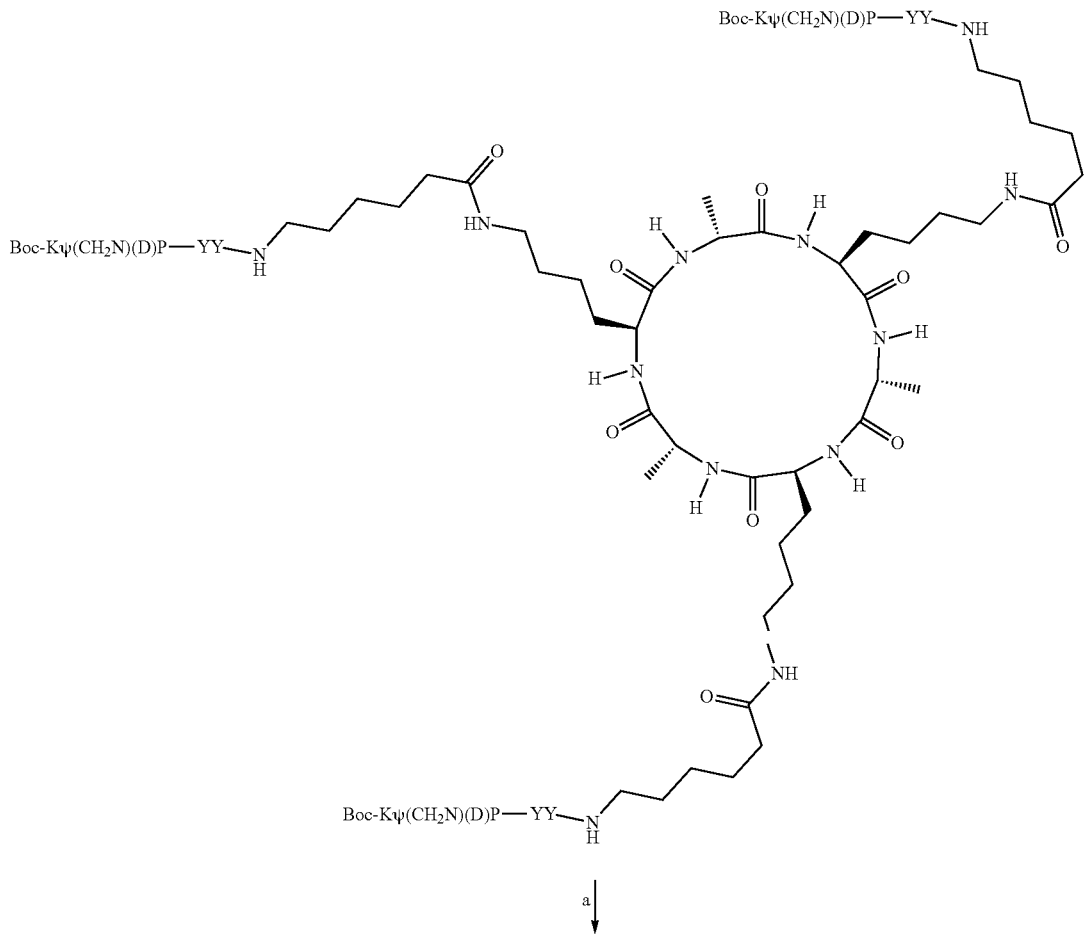
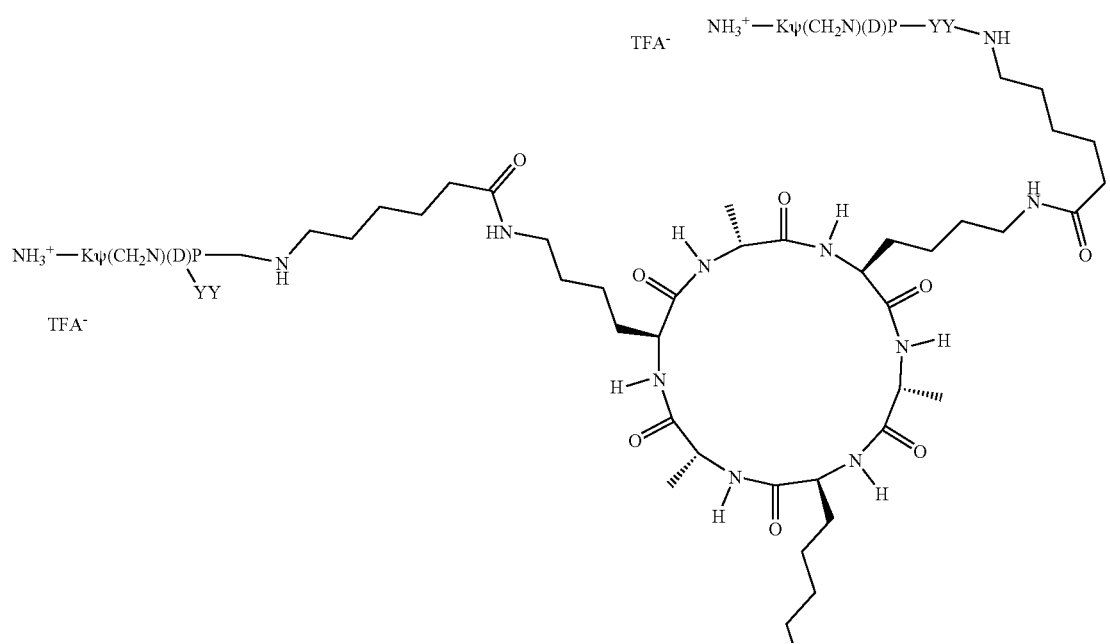

-continued

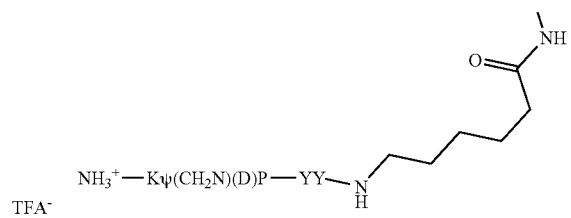

a) TFA, H2O; b) pentapeptide L63', BOP, DIEA, DMF 35 mg (3.3 eq.) of pentapeptide Boc-Lys(Boc)ψ(CH₂N)_DPro-Tyr(tBu)-Tyr(tBu)-Ahx-OH (SEQ ID NO: 11) (L63'), 16 mg (3.3 eq.) of BOP are added to 10 mg (1 eq.) of ring 9 in DMF (see Example 3) and 20 µl (10 eq.) of DIEA is added. The reaction mixture is stirred for 25 hours at room temperature, then precipitated from NaHCO₃ (aq). After filtration, the precipitate is washed successively with H₂O, 1N KHSO₄, H₂O and AcOEt.

The solid formed is then treated with TFA in the presence of water. After stirring for 30 minutes, the solution is precipitated from ether and filtered in order to produce 20 mg of L62 ligand.

2 mg of pure L62 is obtained after purification by RP-HPLC (yield after purification 7%).

The L62 ligand is characterized by:

HPLC: $t_R$ 11.6 min (linear gradient, 5-65% B, 20 min)

MALDI-TOF: calculated for $C_{132}H_{201}N_{27}O_{24}H^+$: 2550.21; observed 2551; calculated for $C_{132}H_{201}N_{27}O_{24}K^+$: 2590.21; observed 2590.

Example 8

Preparation of the Compound of Formula (III-j) (L68)

Compound L68 corresponds to the following formula:

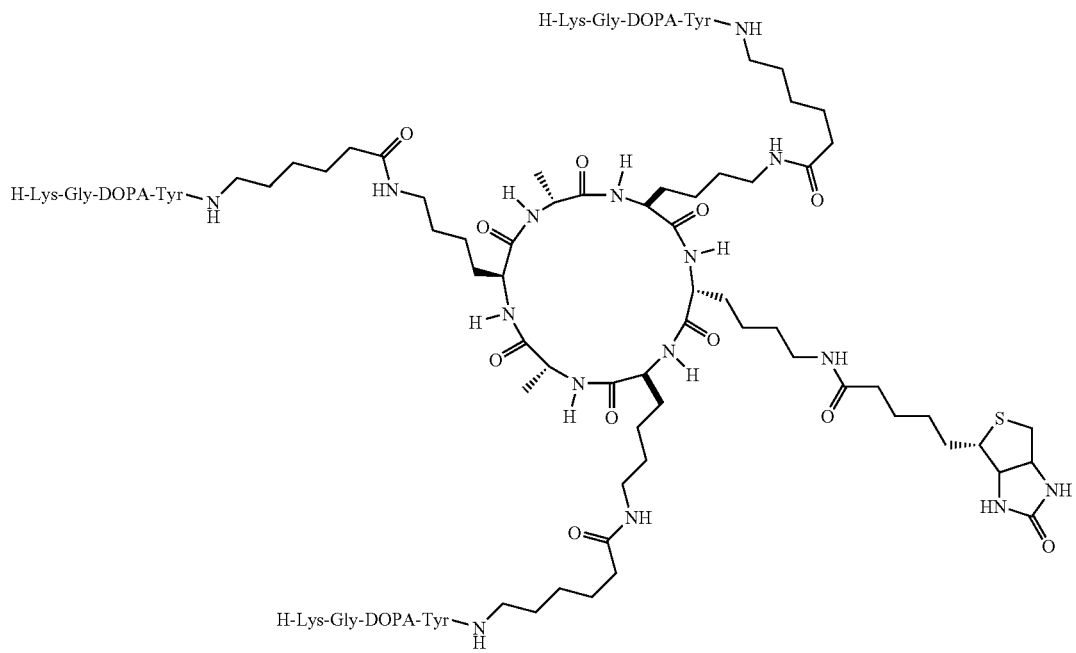

Reaction scheme
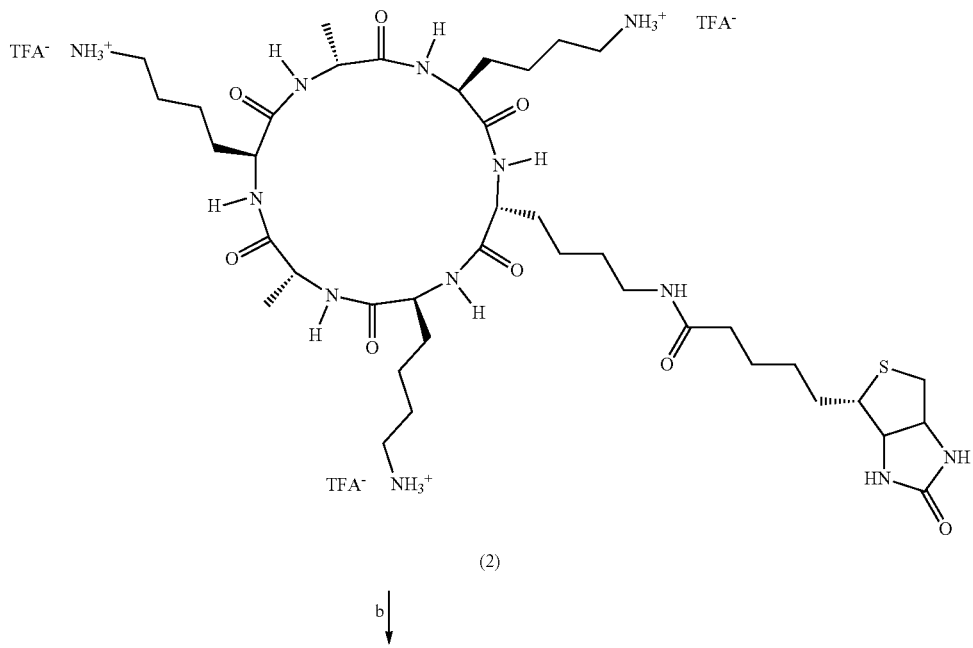
(2)
b ↓
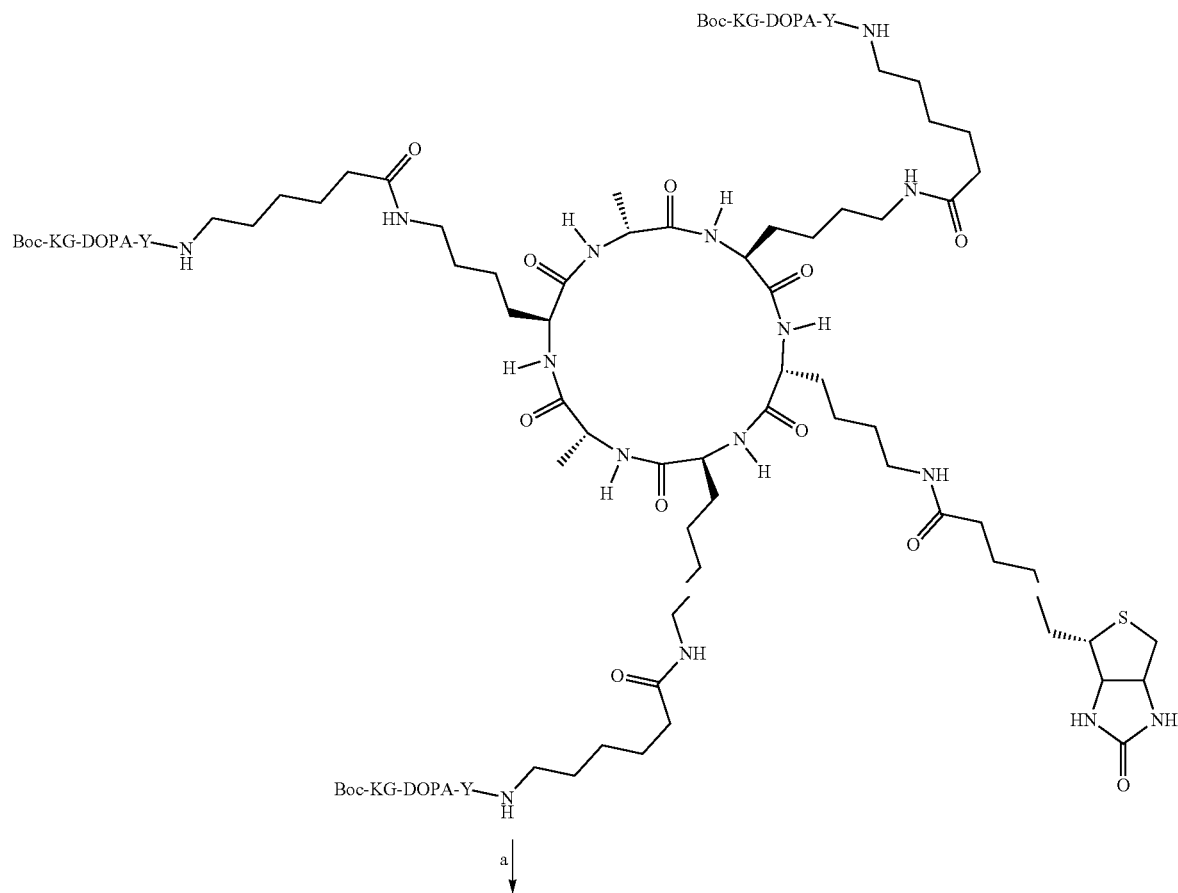
a ↓

-continued

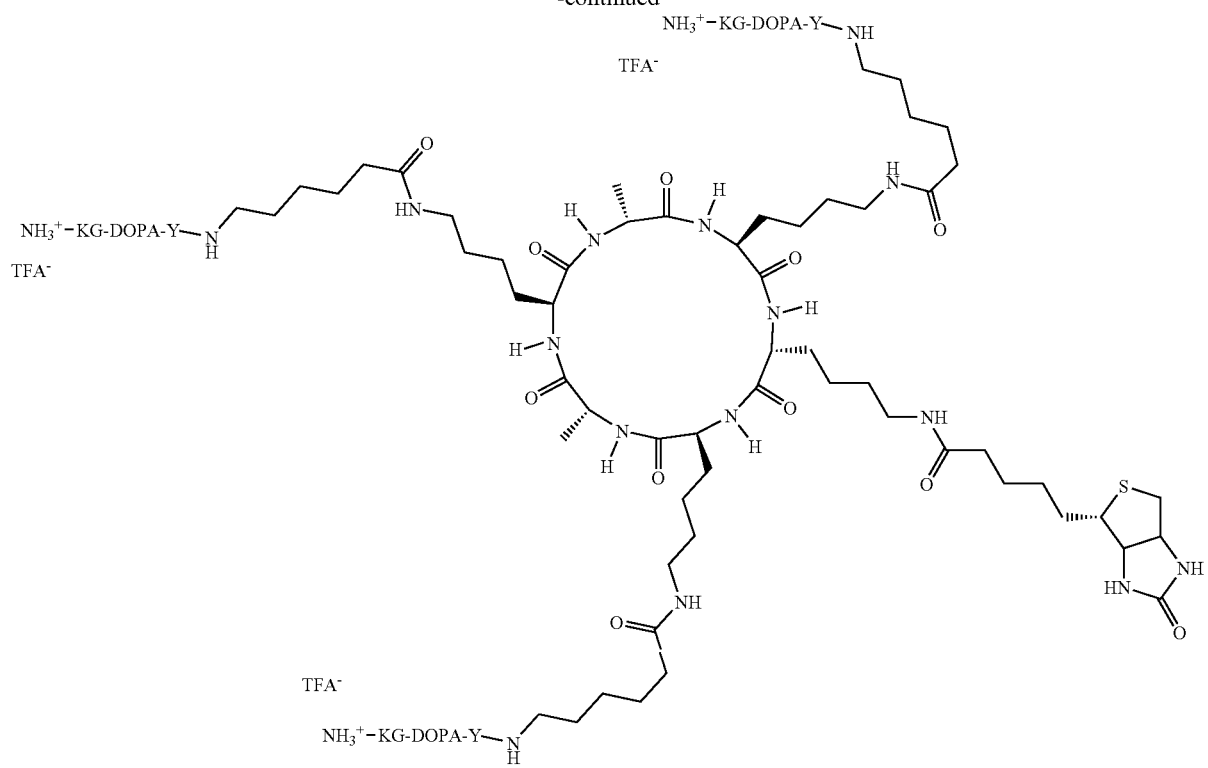

a) TFA, H2O; b) pentapeptide L69', BCIP, DIEA, DMF 39 mg (3.3 eq.) of pentapeptide Boc-Lys(Boc)-Gly-Dopa (Acetonid)-Tyr(tBu)-Ahx-OH (SEQ ID NO: 12) (L69'), 18 mg (3.3 eq.) of BOP are added to 15 mg (1 eq.) of biotin ring (2) in DMF (see Example 3) and 30 µl (10 eq.) of DIEA is added. The reaction mixture is stirred for 25 hours at room temperature, then precipitated from $NaHCO_3$ (aq). After filtration, the precipitate is washed successively with $H_2O$, 1N $KHSO_4$, $H_2O$ and AcOEt.

The solid formed is then treated with TFA in the presence of water. After stirring for 30 minutes, the solution is precipitated from ether and filtered in order to produce 50 mg of L68 ligand.

9 mg of pure L68 is obtained after purification by RP-HPLC (yield after purification 21%).

The L68 ligand is characterized by:

HPLC: $t_R$ 11.1 min (linear gradient, 5-65% B, 20 min)

MALDI-TOF: calculated for $C_{136}H_{204}N_{30}O_{32}SH^+$: 2804.35; observed 2802.96; calculated for $C_{136}H_{204}N_{30}O_{32}SNa^+$: 2827.35; observed 2824.91; calculated for $C_{136}H_{204}N_{30}O_{32}SK^+$: 2841.35; observed 2841.98.

Biological Tests

These tests are carried out in 3 phases. The most useful ligands are first chosen by means of simple lymphoma cell apoptosis activation tests, then their interaction with CD40 is finely analyzed with BIAcore technology, and finally the interaction of the biotinylated ligands with the membranous CD40 is studied by fluorescence microscopy and flow cytometry.

The agonist or antagonist effect of the ligands was tested by means of two standard biological tests. The first test is based on the property of certain B lymphomas of ceasing to proliferate and enter into apoptosis during the bridging of their membranous CD40 molecule (Tong et al., 1999). In fact, certain B lymphomas enter into apoptosis during the bridging of their CD40 molecule by an anti-CD40 antibody or by soluble CD40L independently of the CD95 molecule. This induction of apoptosis has the effect of reducing proliferation. The agonist ligands of CD40 will induce an increase in apoptosis and as a result a reduction in proliferation. In this test, the BL41 cells are incubated with CD40 ligands and after 24 hours either the inhibition of proliferation of these cells is measured by studying the incorporation of tritiated thymidine, or the percentage of apoptotic cells is measured by a flow cytometry study. In the second test, the expression of the membranous CD95 molecule by transformed B cells (Burkitt's lymphomas) after activation by the CD40-CD40L interaction (Schaffner et al., 1996) is studied. In this test, the CD40L partner is expressed on transfected fibroblasts (3T6-CD40L) (Buelens et al., 1997). The BL41 Burkitt's lymphoma cells are incubated with fibroblasts which are transfected or not transfected with CD40L. After 48 hours, the expression of CD95 is evaluated by flow cytometry. The expression of CD95 is induced in the presence of CD40L and a commercial anti-CD40L antibody inhibits the consequences of the CD40-CD40L interaction.

The agonist effect of the ligands is evaluated by measuring, after incubation of B cells with ligans, either the expression of CD95 using flow cytometry or the inhibition of proliferation and/or the increase of death by apoptosis. The antagonist effect is evaluated by measuring the reduction of the expression of CD95 induced by the CD40L in the presence of the different ligands.

A—Study of the Agonist Biological Effect of the Ligands

Principle

The agonist effect of the ligands was tested by means of a simple biological test which is based on the property of certain B lymphomas of entering into apoptosis during the bridging of their membranous CD40 molecule (Tong et al., 1999). In fact, these B lymphomas enter into apoptosis during the bridging of their CD40 molecule by an anti-CD40 antibody or by soluble CD40L. The agonist ligands of CD40 will similarly induce an increase in the apoptosis of Burkitt's lymphoma cells which is measured by a precise analysis with flow cytometry.

Operating Method

BL41 Burkitt's or Raji (ATCC CCL-86) lymphoma cells ($5.10^5$/mL) two similar cell lines, are cultured in the presence of the different ligands at the desired concentrations. After 16 hours, the cells are labelled with 3,3'-dihexyloxacarbocyanine iodide ($DiOC_6$) at 40 nM (Petit et al., 1995) in order to evaluate the percentage of apoptotic cells using flow cytometry. As a control, the effect of the ligands was tested on Jurkat T lymphoma cells which do not express CD40 and do not react in the presence of a soluble or membranous CD40 ligand.

Results

Figure 5A:
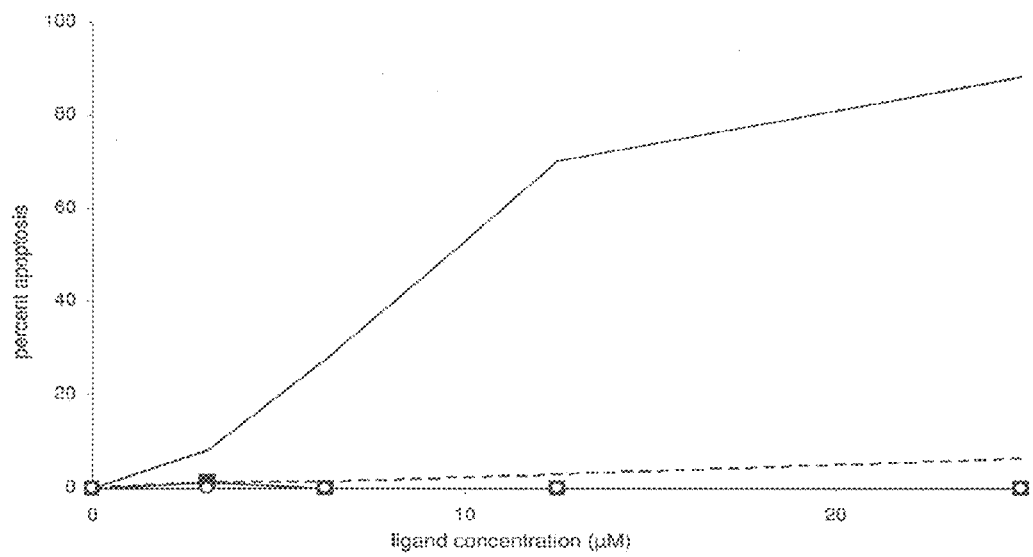
FIG. 5A represents the percentage of apoptosis of the BL41 cells, induced by the L36 ligand incubated for 16 hours, using flow cytometry after a labelling with $DiOC_6$. The solid curve corresponds to the dose-response of the apoptosis induced by the L36 ligand. The dotted curve corresponds to the dose-response of the apoptosis induced by the L36 ligand on the Jurkat cell line which does not express CD40. The solid curve with the black squares corresponds to the dose-response of the apoptosis induced by the control pentapeptide (L37) (H-Lys-(D)Pro-Tyr-Tyr-Ahx-OH (SEQ ID NO: 2)) on BL41 and the solid curve with the white circles corresponds to the dose-response of the apoptosis induced by the control pentapeptide (L37) on Jurkat.
Figure 5B:
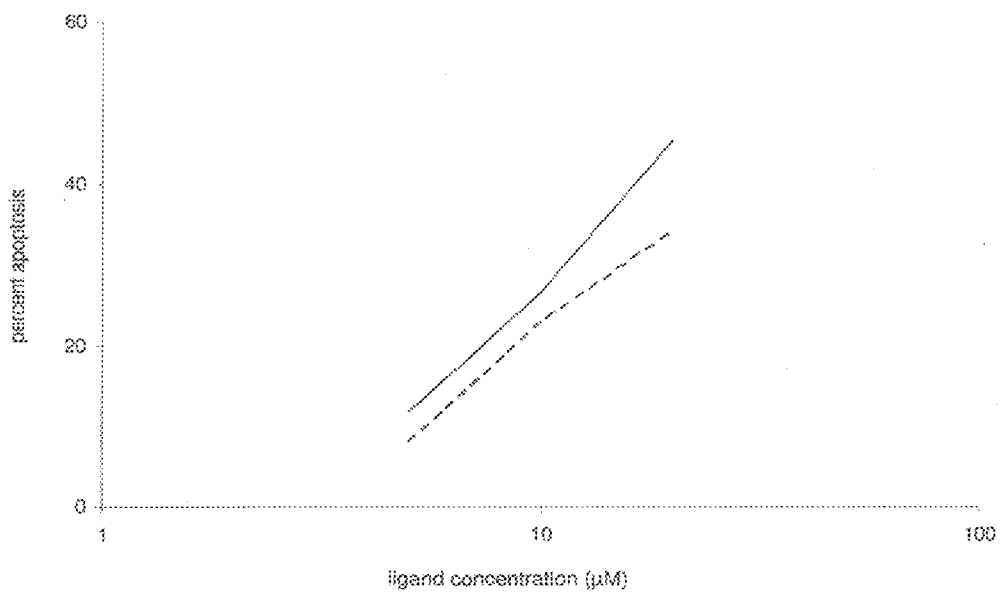
FIG. 5B represents the percentage of apoptosis of the BL41 cells, induced by the L4 and L41 ligands incubated for 16 hours, using flow cytometry after a labelling with $DiOC_6$. The solid curve corresponds to the dose-response of the apoptosis induced by the L4 ligand. The dotted curve corresponds to the dose-response of the apoptosis induced by the L41 ligand.
Figure 5C:
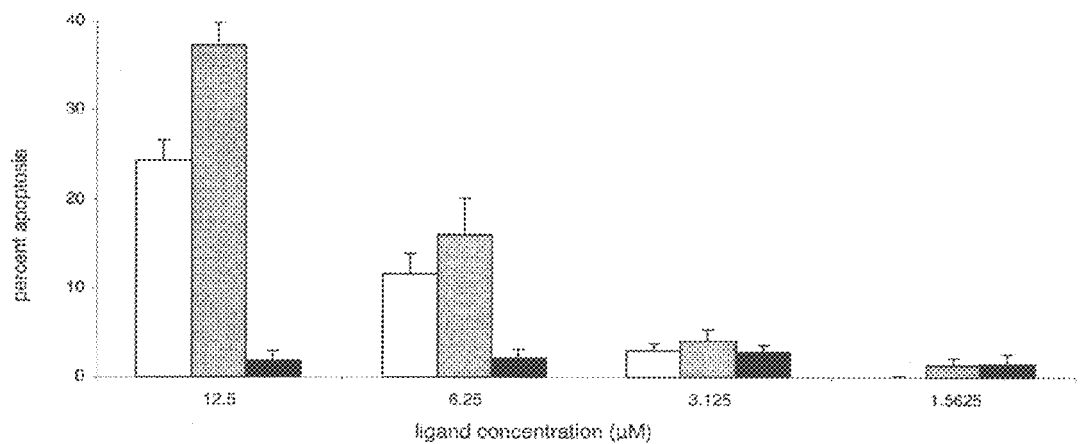
FIG. 5C represents the percentage of apoptosis of the BL41 cells, induced by the L4 and L40 ligands incubated for 16 hours, using flow cytometry after a labelling with $DiOC_6$. The values correspond to the averages plus or minus the mean deviations of 3 independent experiments on the BL41 cells. The white histograms correspond to the dose-response of the apoptosis induced by L4, the black histograms correspond to the dose-response of the apoptosis induced by L45 and the grey histograms correspond to the dose-response of the apoptosis induced by L40. The control peptide (L45) (H-Lys-Pro-Tyr-Tyr-Ahx-OH (SEQ ID NO: 10)) in which D-Proline is replaced by L-Proline has no activity.
Figure 5D:
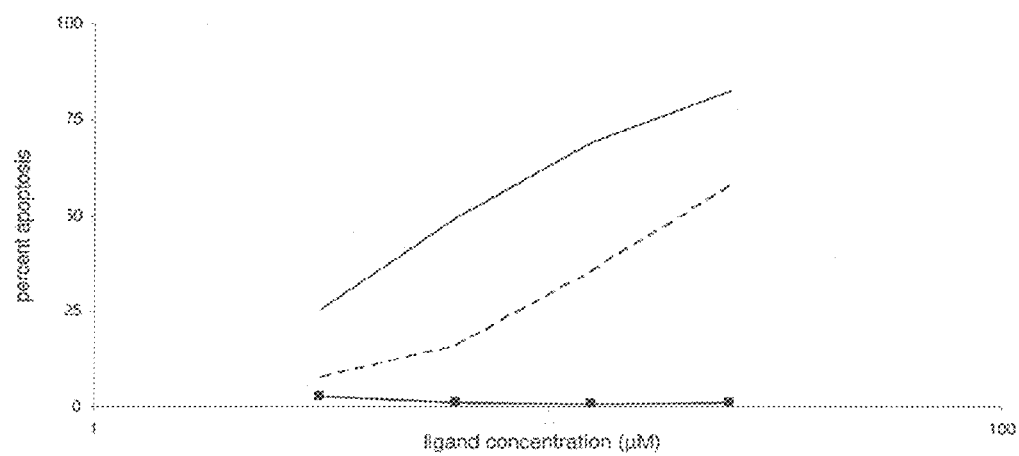
FIG. 5D represents the percentage of apoptosis of the Raji cells, induced by the L4, L43 and L44 ligands, incubated for 16 hours, using flow cytometry after a labelling with $DiOC_6$. The solid curve corresponds to the dose-response of the apoptosis induced by L4, the dotted curve corresponds to the dose-response of the apoptosis induced by L43 and the curve with the black squares corresponds to the dose-response of the apoptosis induced by L44.

The L36 (V-b) ligand strongly induces the apoptosis of BL41 cells since at 25 µM more than 80% of specific apoptosis is detected (FIG. 5A). The biotinylated ligand L41 has a biological activity comparable to its non-biotinylated homologue L4 (non-biotinylated L41) (FIG. 5B). The L40 ligand is more effective than L4 since at 12.5 µM, L40 induces 37.5% of specific apoptosis and L4 24% (FIG. 5C). Finally the L43 ligand is less effective than its homologue L4 (FIG. 5D). It can be noted that none of these ligands induces the apoptosis of cells of the Jurkat line.

Figure 8A:
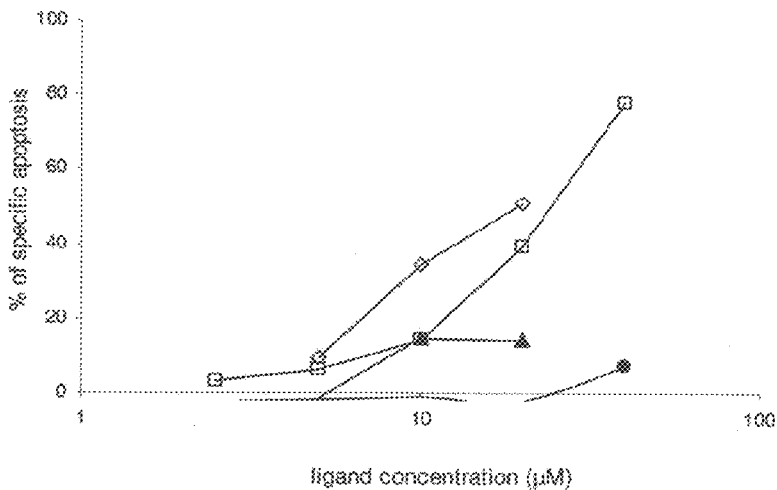
FIG. 8A represents the percentage of specific apoptosis of Burkitt Raji lymphoma (CD40+) and T Jurkat leukemia (CD40−) cells at $5 \times 10^5$ cells/ml after culture for 16 hours in the presence of different concentrations of the L4 and L62 ligands. The curve with the white diamonds corresponds to the dose-response of the apoptosis induced by L4 on the Raji cells; the curve with the white squares corresponds to the dose-response of the apoptosis induced by L62 on the Raji cells; the curve with the black triangles corresponds to the dose-response of the apoptosis induced by L4 on the Jurkat cells and the curve with the black circles corresponds to the dose-response of the apoptosis induced by L62 on the Jurkat cells.
Figure 8B:
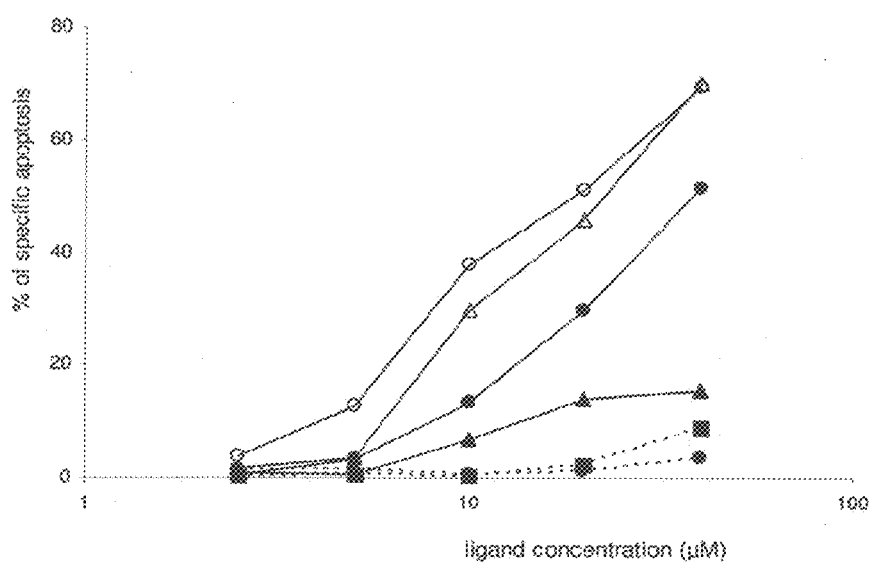
FIG. 8B represents the percentage of specific apoptosis of the Raji, Jurkat and Burkitt BL41 lymphoma (CD40+) cells treated with the different L62 and L40 ligands under the same conditions as in FIG. 8A during an independent experiment. The solid curve with the white circles corresponds to the dose-response of the apoptosis induced by L40 on the Raji cells; the solid curve with the white triangles corresponds to the dose-response of the apoptosis induced by L62 on the Raji cells; the solid curve with the black circles corresponds to the dose-response of the apoptosis induced by L40 on the BL41 cells; the solid curve with the black triangles corresponds to the dose-response of the apoptosis induced by L62 on the BL41 cells; the dotted curve with the black squares corresponds to the dose-response of the apoptosis induced by L40 on the Jurkat cells and the dotted curve with the black circles corresponds to the dose-response of the apoptosis induced by L62 on the Jurkat cells.

Moreover, according to FIGS. 8A and 8B, it is noted that the introduction of a reduced bond between the first two residues (L62) makes it possible to obtain an effective and selective ligand.

B—Study of the Interaction Between the Ligands and CD40

Principle

The BIAcore 3000 is a device which allows the study of the interactions between two molecules. Based on surface plasmon resonance, it makes it possible to carry out measurements in real time and thus to follow the interaction kinetics (association and dissociation) of an "analyte" (which is found in an injected solution) with a "ligand" (immobilized on a microchip supporting the measurement). Kinetic measurements at different concentrations of analyte make it possible to calculate the affinity constants of the interaction between the ligand and the analyte. The microchip contains four cells with different measurements, which makes it possible to directly compare a reference cell on which a non-pertinent protein (a protein which has no affinity for the analyte studied but close to the ligand) is immobilized, with the cell on which the ligand is immobilized.

The test is carried out in two stages: measurement of the direct interaction of the ligands with the CD40 immobilized on the microchip and measurement of the inhibition of the CD40-CD40L interaction by the ligands.

1—Interaction of the Ligands on the CD40

Operating Method

Rabbit antibodies directed against the constant part of mouse immunoglobulins were immobilized on a microchip. A mouse monoclonal antibody of isotype IgG2a (LG11.2) at 100 nM is immobilized in the reference cell with a flow of 5 µL/min for one minute. In the ligand cell, the recombinant CD40 associated with the constant part of the heavy chain of mouse IgG2a (human CD40 muIg fusion protein, ANCELL Corporation, Bayport, Minn.) is immobilized under the same conditions.

The CD40 ligands are then injected, as analytes, at different concentrations in the two cells (reference and ligand). The flow is 30 µL/min over 4 minutes in order to study the association then, in the absence of analyte, the conditions are identical in order to study the dissociation.

In order to regenerate the cells (i.e. to remove all the proteins adsorbed in a non-covalent manner), a 50 mM HCl solution is injected at 5 µL/min over 1 minute. The cells are then ready for a new analysis.

Results

Figure 6:
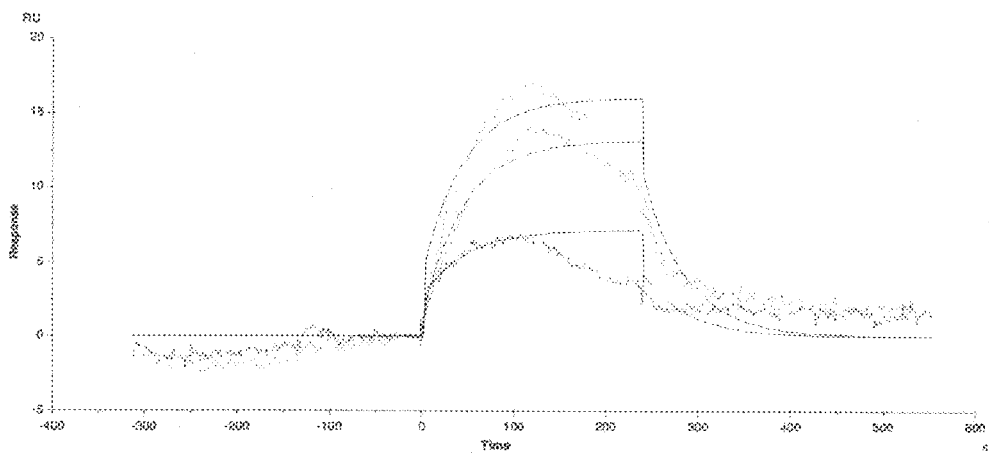
FIG. 6 represents sensorgrams measured for the direct interaction kinetics of the L40 ligand with CD40 (response as a function of time). Here, the L40 ligand is injected at concentrations of 25, 100 and 200 nM at a flow rate of 30 µl/min over 4 minutes.

The kinetics of direct association to CD40 of the L40 and L41 ligands were measured (FIG. 6) and made it possible to calculate dissociation constants of $3.1 \times 10^{-7}$M for L40 and $2.8 \times 10^{-8}$M for L41. For information, the dissociation constant calculated for L4 under the same conditions is $9.4 \times 10^{-8}$M.

2—Inhibition of the CD40-CD40L Interaction

Operating Method

Rabbit antibodies directed against the constant part of mouse immunoglobulins were immobilized on a microchip. A mouse monoclonal antibody of isotype IgG2a (LG11.2) at 40 nM is immobilized in the reference cell with a flow of 5 µL/min for two minutes. In the ligand cell, the recombinant CD40 associated with the constant part of the heavy chain of mouse IgG2a (human CD40 muIg fusion protein, ANCELL Corporation, Bayport, Minn.) is immobilized under the same conditions.

CD40L (human CD154 muCD8 fusion protein, ANCELL Corporation) at 35 nM is then injected, as analyte, in the two cells (reference and ligand) in the presence of the ligands at different concentrations. The flow, in the presence of analytes, is 10 µL/min over 5 minutes in order to study the association then, in the absence of analyte, the conditions are identical in order to study the dissociation.

In order to regenerate the cells (i.e. to remove all the proteins adsorbed in non-covalent manner), a 10 mM HCl solution is injected at 5 µL/min over 1 minute. The cells are then ready for a new analysis.

Results

The association of CD40L to CD40 was studied in the presence of different concentrations of L40 or L43 ligand. At 1 µM, the L40 ligand inhibits the binding of CD40L to CD40 100%, whilst under the same conditions the L43 ligand inhibits it 30%.

C—Study of the Interaction Between the Biotinylated Ligands and the Membranous CD40

Principle

The direct analysis of the interaction of a ligand with the membranous CD40 is made possible with the biotinylation of the ligands. The binding of these ligands to the CD40 is developed using a streptavidin, a ligand specific to and with a high affinity for biotin, labelled with a fluorochrome. The objective is the detection of the CD40 using specific ligands, in the same manner as with monoclonal anti-CD40 antibodies. These specific ligands not recognizing the same epitope as the anti-CD40 antibodies, it has been possible to use them in double-labelling experiments using fluorescence microscopy in order to confirm their colocalization with the anti-CD40 antibodies, i.e. their specificity to CD40.

Operating Method

For a flow cytometry analysis, $10^6$ cells are incubated with 2.5 µM of biotinylated ligand in 100 µl of phosphate buffer at 4° C. for 15 minutes. The cells are then placed in the presence of streptavidin labelled with the fluorochrome fluorescein isothiocyanate, diluted 500 times in 100 µl of phosphate buffer at 4° C. over 10 minutes. The cells thus labelled are analyzed using flow cytometry.

For fluorescence or confocal microscopy analysis, $10^6$ cells are fixed with 1% paraformaldehyde in the phosphate buffer overnight at 4° C. The next day, the cells are placed in the presence of 2.5 µM of biotinylated ligand and a monoclonal mouse antibody directed against CD40 diluted 100 times, the whole being in 100 µl of phosphate buffer containing 1% of bovine serum albumin at 4° C. for 30 minutes. The cells are then incubated with a streptavidin labelled with the fluorochrome Alexa$^{546}$ diluted 500 times and a goat antibody directed against the Fc part of the mouse antibody coupled to the fluorochrome Alexa$^{488}$ diluted 500 times, the whole being in 100 µl of phosphate buffer/bovine serum albumin at 4° C. for 15 minutes. The cells thus labelled are then resuspended in a mounting medium before arranging them between slide and lamellae and observing them under the microscope.

Results

Figure 7A:
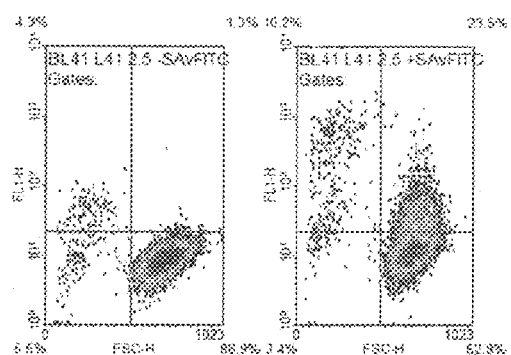
FIG. 7A represents the labelling under flow cytometry of the BL41 cells using the biotinylated L41 ligand developed by streptavidin-FITC. The y-axis corresponds to the fluorescence intensity (FL1-H) of the labelled cells with the L41 ligand then streptavidin, the x-axis corresponds to the size of the cells (FSC-H). The density curve on the left corresponds to the cells labelled with the biotinylated ligand but without streptavidin, that on the right corresponds to the cells labelled with the biotinylated ligand then the streptavidin coupled with the fluorochrome FITC. The grey to black colouring indicates a decreasing cell density at a point on the x-axis FSC and y-axis FL1.
Figure 7B:
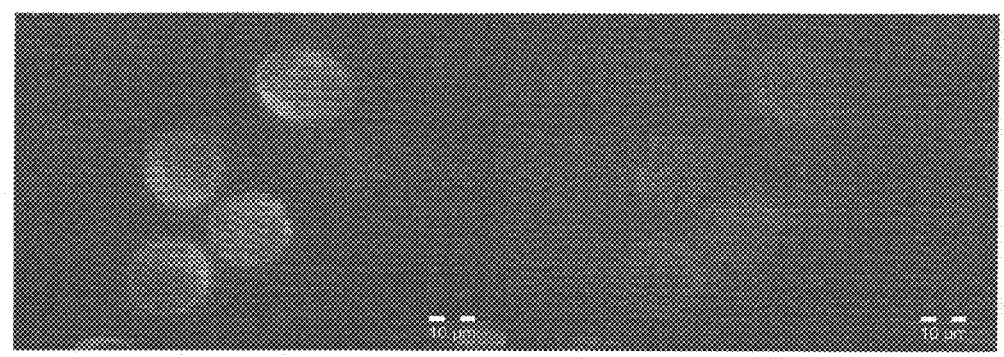
FIG. 7B represents the labelling under fluorescence microscopy of the BL41 cells using the biotinylated L41 ligand and an antibody directed against CD40, developed respectively by a streptavidin Alexa$^{546}$ and a goat antibody directed against the Fc part of the mouse antibody coupled with the fluorochrome Alexa$^{488}$. The grey colouring on the left side of the figure corresponds to the labelling of the antibody directed against CD40 and the grey colouring on the right side of the figure to the labelling of the biotinylated L41 ligand.

The biotinylated L41 ligand was used in labelling using flow cytometry. Its interaction with the membranous CD40 of the BL41 cells is developed using a streptavidin labelled with the fluorochrome fluorescein isothiocyanate (FITC) detected in the FL1 channel of the cytometer (FIG. 7A). The result of the double labelling using microscopy indicates that the L41 ligand is specific to CD40 since the labelling corresponds to that of the antibody directed against CD40 (FIG. 7B).

REFERENCES

Buelens, C., Verhasselt, V., De Groote, D., Goldman, M., Willems, F. (1997) Human dendritic cell responses to lipopolysaccharide and CD40 ligation are differentially regulated by interleukin-10, *Eur J Immunol.*, 27: 1848-52, Chaussabel, D., Jacobs, F., de Jonge, J., de Veerman, M., Carlier, Y., Thielemans, K., Goldman, M., Vray, B. (1999) CD40 ligation prevents *Trypanosoma cruzi* infection through interleukin-12 upregulation, *Infect Immun.*, 67: 1929-34, Diehl, L., den Boer, A. T., Schoenberger, S. P., van der Voort, E. I., Schumacher, T. N., Melief, C. J., Offring a, R., Toes, R. E. (1999) CD40 activation in vivo overcomes peptide-induced peripheral cytotoxic T-lymphocyte tolerance and augments anti-tumor vaccine efficacy, *Nat. Med.*, 5: 774-9, Howard, L. M., Miga, A. J., Vanderlugt, C. L., Dal Canto, M. C., Laman, J. D., Noelle, R. J., Miller, S. D. (1999) Mechanisms of immunotherapeutic intervention by anti-CD40L (CD154) antibody in an animal model of multiple sclerosis, *J Clin Invest.*, 103: 281-90, Kaiser, E. et coll. (1970) *Anal. Biochem.*, 34, 595-598, Kikuchi, T., Moore, M. A., Crystal, R. G. (2000) Dendritic cells modified to express CD40 ligand elicit therapeutic immunity against preexisting murine tumors, *Blood.* 96: 91-9, Kirk, A. D., Burkly, L. C., Batty, D. S., Baumgartner, R. E., Berning, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J., Harlan, D. M. (1999) Treatment with humanized monoclonal antibody against CD154 prevents acute renal allograft rejection in non-human primates, *Nat. Med.*, 5: 686-93, Lode, H. N., Xiang, R., Pertl, U., Forster, E., Schoenberger, S. P., Gillies, S. D., Reisfeld, R. A. (2000) Melanoma immunotherapy by targeted IL-2 depends on CD4(+) T-cell help mediated by CD40/CD40L interaction, *J Clin Invest.*, 105: 1623-30, Petit, P. X., Lecoeur, H., Zorn, E., Dauguet, C., Mignotte, B., Gougeon, M. L. (1995) Alterations in mitochondrial structure and function are early events of dexamethasone-induced thymocyte apoptosis, *J Cell Biol*, 130: 157-167, Schattner, E. J., Mascarenhas, J., Bishop, J., Yoo, D. H., Chadburn, A., Crow, M. K., Friedman, S. M. (1996) CD4$^+$ T-cell induction of Fas-mediated apoptosis in Burkitt's lymphoma B cells, *Blood*, 88: 1375-82, Sotomayor, E. M., Borrello, I., Tubb, E., Rattis, F. M., Bien, H., Lu, Z., Fein, S., Schoenberger, S., Levitsky, H. I. (1999) Conversion of tumor-specific CD4+T-cell tolerance to T-cell priming through in vivo ligation of CD40. *Nat. Med.*, 5: 780-7, Spatola, A. F., "Peptide Backbone Modifications" in Chemistry and Biochemistry of Amino Acids, Peptides and Proteins, vol. III, B. Weinstein, ed. Marcel Dekker, New York, 1983, pages 267-357, Tong, A. W., B. Seamour, J. Chen, D. Su, G. Ordonez, L. Frase, G. Netto, and M. J. Stone. 2000. CD40 ligand-induced apoptosis is Fas-independent in human multiple myeloma cells. *Leuk Lymphoma* 36:543-558.

The invention claimed is:

1. A compound corresponding to the following formula (I):

$$R_c \underset{R_c}{\overset{R_c}{\underset{|}{Y}}}$$ (I)

wherein:

Y represents a macrocycle functionalized by three amine or COOH functions, and corresponds to formula (II):

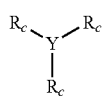 (II)

j is 0 or 1;

A represents an amino acid residue or an amino acid derivative selected from the group consisting of:

(1), (2), (3), (4), (5), (6), (7)

-continued

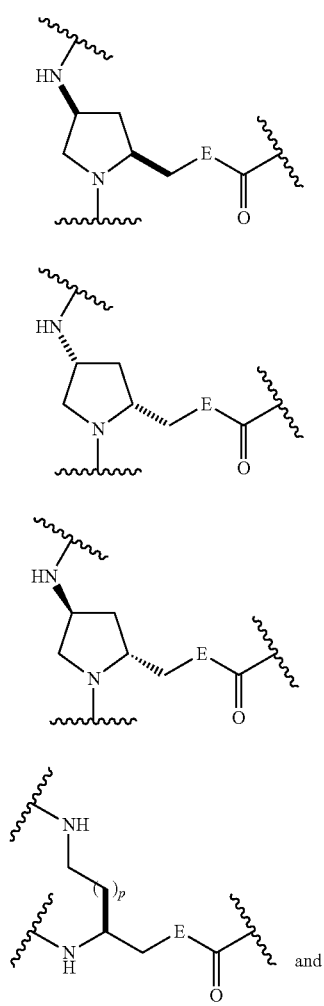

(8)

(9)

(10)

(11)

(12)

n representing 0, 1, 2 or 3;
p representing 0, 1, 2 or 3; and
E representing NH or O;
B¹ is an amino acid residue or an amino acid derivative selected independently from the group consisting of:

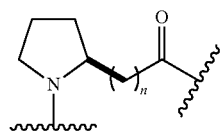

(13)

-continued

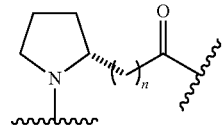

(14)

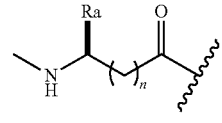

(15)

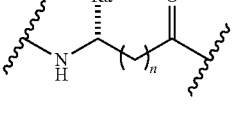

(16)

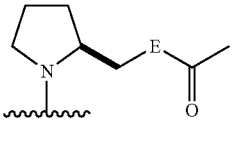

(17)

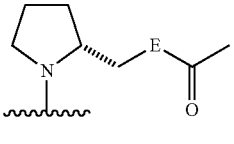

(18)

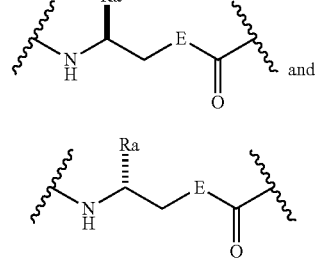

(19) and (20)

n representing 0, 1, 2 or 3;
p representing 0, 1, 2 or 3;
E representing NH or O; and
Ra representing a chain of a proteinogenic amino acid, C1-C8 alkylated;
B² is identical to B¹ or is selected independently from the group consisting of:

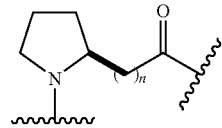

(13)

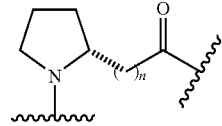

(14)

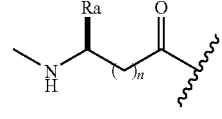

(15)

(16) 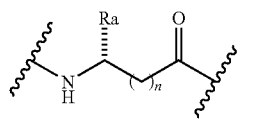

(17) 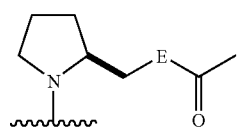

(18) 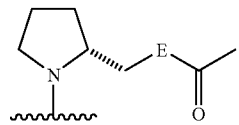

(19) 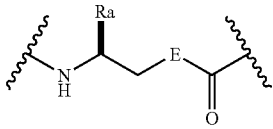

(20) 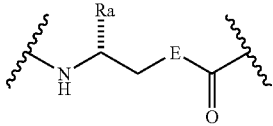

(21) 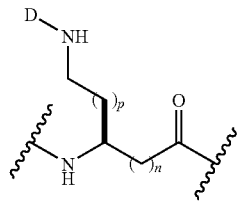

(22) 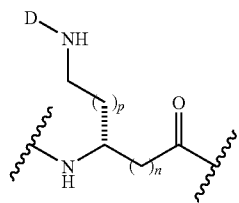

(23) 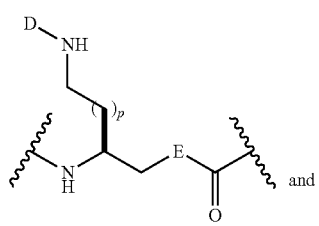 and

(24) 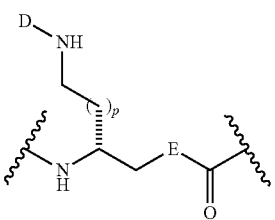

n representing 0, 1, 2 or 3;
p representing 0, 1, 2 or 3;
E representing NH or O;
Ra representing the chain of a proteinogenic amino acid, C1-C8 alkylated;
D representing one of the following groups: (+)-Biotinyl-, (+)-Biotinyl-$X_g$—, HS—$(CH_2)_q$—CO—, Pys-S—$(CH_2)_q$—CO—, Npys-S—$(CH_2)_q$—CO—, HS—$(CH_2)_q$—CO—$X_g$—, Pys-S—$(CH_2)_q$—CO—$X_g$—, and Npys-S—$(CH_2)_q$—CO—$X_g$—,
q representing an integer varying from 2 to 6; and
$X_g$ corresponding to a residue selected from one of the following groups:
—$NH_2$—$(CH_2)_n$—COOH, n varying from 1 to 10;
—$NH_2$—$(CH_2$—$CH_2$—$O)_m$—$CH_2CH_2COOH$, m varying from 3 to 6;
8-amino-3,6-dioxaoctanoic acid;
tranexamic acid;
N-methyl-tranexamic acid;
4(piperidin-4-yl)butanoic acid;
3(piperidin-4-yl)-propionic acid;
N-(4-aminobutyl)-glycine;
4-carboxymethyl-piperazine;
4-(4-aminophenyl)butanoic acid;
3-(4-aminophenyl)propanoic acid;
4-aminophenylacetic acid;
4-(2-aminoethyl)-1-carboxymethyl-piperazine;
trans-4-aminocyclohexane carboxylic acid;
cis-4-aminocyclohexane carboxylic acid;
cis-4-aminocyclohexane acetic acid;
trans-4-aminocyclohexane acetic acid;
4-amino-1-carboxymethyl piperidine;
4-aminobenzoic acid; and
4(2-aminoethoxy)benzoic acid;
$R_c$ represents a group of formula H—$X_a$—$X_b$—$X_c$—$X_d$—$X_e$—$(X_f)_i$— or H—$X'_a$-L-$X'_b$—$X_c$—$X_d$—$X_e$—$(X_f)_i$—, wherein:
i represents 0 or 1,
$X_a$ is an amino acid selected from the group consisting of: lysine; arginine; ornithine; β-amino acids corresponding to lysine, arginine or ornithine, carrying a substitution in α or β position; tranexamic acid; N-methyl-tranexamic acid; 8-amino-3,6-dioxaoctanoic acid; 4(piperidin-4-yl)butanoic acid; 3(piperidin-4-yl)propionic acid; N-(4-aminobutyl)-glycine; $NH_2$—$(CH_2)_n$—COOH, n varying from 1 to 10; $NH_2$—$(CH_2$—$CH_2$—$O)_m$—$CH_2CH_2COOH$, m varying from 3 to 6; 4-carboxymethyl-piperazine; 4-(4-aminophenyl)butanoic acid; 3-(4-aminophenyl)propanoic acid; 4-aminophenylacetic acid; 4-(2aminoethyl)-1-carboxymethyl-piperazine; trans-4-aminocyclohexanecarboxylic acid; cis-4-aminocyclohexanecarboxylic acid; cis-4-aminocyclohexane acetic acid; trans-4-aminocyclohexane acetic acid; 4-amino-1-carboxymethyl piperidine; 4-aminobenzoic acid; and 4(2-aminoethoxy)benzoic acid;
$X_b$ is an amino acid selected from the group consisting of: D-alanine; D-valine; L-proline substituted in β, γ or δ position; D-proline substituted or non-substituted in β, γ or δ position; N-alkylated natural amino acids, the alkyl group being a methyl, ethyl or benzyl group; acyclic dialkylated amino acids of the following formula:

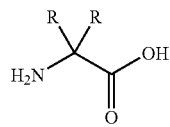

(A)

R representing H, Me, Et, Pr or Bu; and cyclic dialkylated amino acids of the following formula:

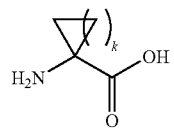

(B)

k representing 1, 2, 3 or 4;

$X_c$ is an amino acid selected from the group consisting of: tyrosine; phenylalanine; 3-nitro-tyrosine; 4-hydroxymethyl-phenylalanine; 3,5-dihydroxy-phenylalanine; 2,6-dimethyl-tyrosine; and 3,4-dihydroxy-phenylalanine (DOPA);

$X_d$ is an amino acid selected from the group consisting of: tyrosine; phenylalanine; 3-nitro-tyrosine; 4-hydroxymethyl-phenylalanine; 3,5-dihydroxy-phenylalanine; 2,6-dimethyl-tyrosine; and 3,4-dihydroxy-phenylalanine;

$X_e$ an amino acid selected from the group consisting of: $NH_2$—$(CH_2)_n$—COOH, n varying from 1 to 10; $NH_2$—$(CH_2$—$CH_2$—$O)_m$—$CH_2CH_2COOH$, m varying from 3 to 6; 8-amino-3,6-dioxaoctanoic acid; tranexamic acid; N-methyl-tranexamic acid; 4(piperidin-4-yl)butanoic acid; 3(piperidin-4-yl)propionic acid; N-(4-aminobutyl)-glycine; 4-carboxymethyl-piperazine; 4-(4-aminophenyl)butanoic acid; 3-(4-aminophenyl)propanoic acid; 4-aminophenylacetic acid; 4-(2aminoethyl)-1-carboxymethyl-piperazine; trans-4-aminocyclohexanecarboxylic acid; cis-4-aminocyclohexanecarboxylic acid; cis-4-aminocyclohexane acetic acid; trans-4-aminocyclohexane acetic acid; 4-amino-1-carboxymethyl piperidine; 4-aminobenzoic acid; and 4(2-aminoethoxy)benzoic acid;

$X_f$ is an amino acid selected from the group consisting of: $NH_2$—$(CH_2)_n$—COOH, n varying from 2 to 10; $NH_2$—$(CH_2$—$CH_2$—$O)_m$—$CH_2CH_2COOH$, m varying from 3 to 6; 8-amino-3,6-dioxaoctanoic acid; tranexamic acid; N-methyl-tranexamic acid; 4(piperidin-4-yl)butanoic acid; 3(piperidin-4-yl)propionic acid; N-(4-aminobutyl)-glycine; 4-carboxymethyl-piperazine; 4-(4-aminophenyl)butanoic acid; 3-(4-aminophenyl)propanoic acid; 4-aminophenylacetic acid; 4-(2aminoethyl)-1-carboxymethyl-piperazine; trans-4-aminocyclohexanecarboxylic acid; cis-4-aminocyclohexanecarboxylic acid; cis-4-aminocyclohexane acetic acid; trans-4-aminocyclohexane acetic acid; 4-amino-1-carboxymethyl piperidine; 4-aminobenzoic acid; and 4(2-aminoethoxy)benzoic acid;

-L- represents a pseudopeptide-type bond between the $X'_a$ and $X'_b$ residues, selected from the group of: -ψ($CH_2CH_2$)—; -ψ(CH($F_k$)=CH($F_k'$))—; -ψ($CH_2NH$)—; -ψ(NHCO)—; -ψ(NHCONH)—; -ψ(CO—O)—; -ψ(CS—NH)—; -ψ(CH(OH)—CH(OH))—; -ψ(S—$CH_2$)—; -ψ($CH_2$—S)—; -ψ(CH(CN)—$CH_2$)—; -ψ(CH(OH))—; -ψ(COCH$_2$)—; -ψ(CH(OH)$CH_2$)—; -ψ(CH(OH)$CH_2$NH)—; -ψ($CH_2$)—; -ψ(CH($F_k$))—; -ψ($CH_2$O)—; -ψ($CH_2$—NHCONH)—; -ψ(CH($F_k$)NHCON$F_k'$)—; -ψ($CH_2$—CONH)—; -ψ(CH($F_k$)CONH)—; and -ψ(CH($F_k$)CH($F_k'$)CONH)—; and when $X'_b$ represents the side chain of a proline, then -L- represents -ψ($CH_2N$)—; -ψ(NH-CON)—; -ψ(CS—N)—; -ψ(CH(OH)$CH_2N$)—; -ψ($CH_2$—NHCON)—; -ψ($CH_2$—CON)—; -ψ(CH($F_k$)CON)—; -ψ(CH($F_k$)CH($F_k'$)CON)—, $F_k$ and $F_k'$ representing, independently of one another, a hydrogen, a halogen, an alkyl group of 1 to 20 carbon atoms, or an aryl group the ring structure of which having from 5 to 20 carbon atoms;

$X'_a$ represents a side chain of lysine, arginine or ornithine; and $X'_b$ represents a side chain of an amino acid selected from the group consisting of: glycine; asparagine; D-alanine; D-valine; L-proline substituted or non-substituted in β, γ or δ position; D-proline substituted or non-substituted in β, γ or δ position; N-alkylated natural amino acids, the alkyl group being a methyl, ethyl or benzyl group; acyclic dialkylated amino acids of the following formula:

(A)

R representing H, Me, Et, Pr or Bu; and cyclic dialkylated amino acids of the following formula:

(B)

k representing 1, 2, 3 or 4.

2. The compound according to claim 1, wherein $X_a$ is not a lysine residue.

3. The compound according to claim 1, wherein the compound is labelled with biotin.

4. The compound according to claim 1, corresponding to one of the following formulae:

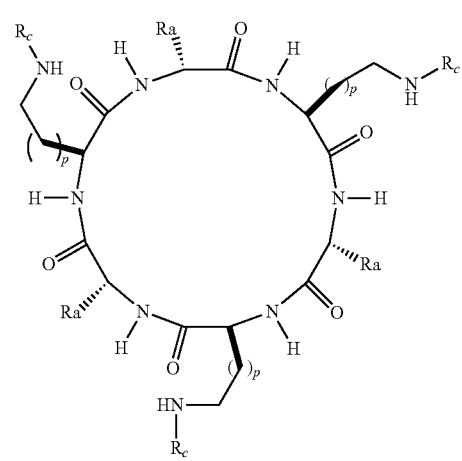
(III)
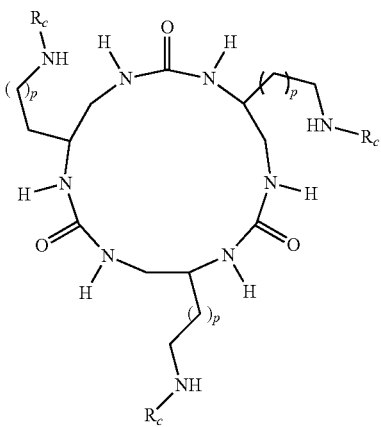
(VI)
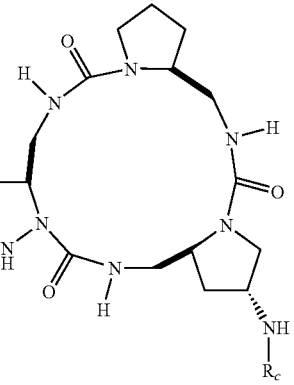
(VII)
$R_c$ being as previously defined,
Ra representing a chain of a proteinogenic amino acid, C1-C8 alkylated, and
p representing 0, 1, 2 or 3.
5. The compound according to claim 4, corresponding to the following formula (III-a):
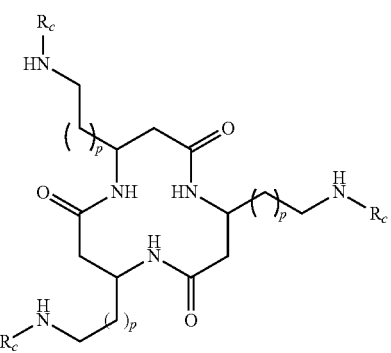
(IV)
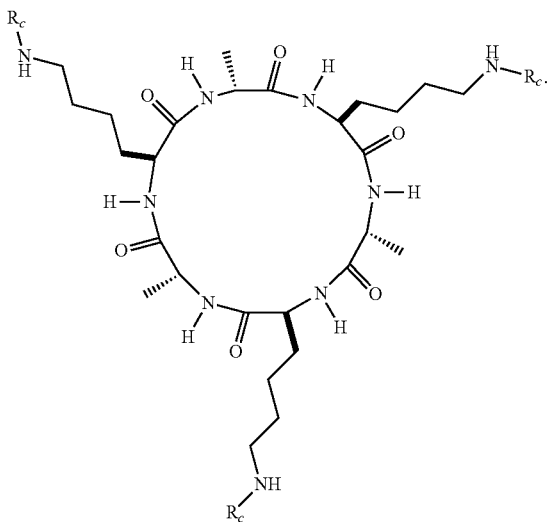
(III-a)
(V)

6. The compound according to claim 4, corresponding to the following formula (V-a):
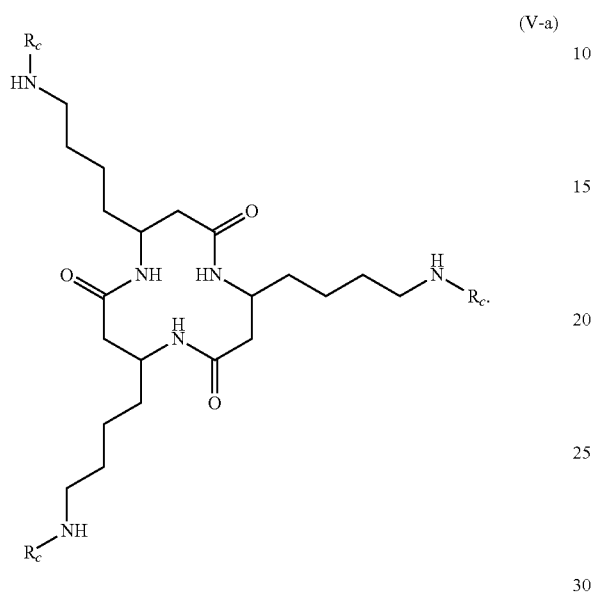
(V-a)
7. The compound according to claim 1, corresponding to one of the following formulae:
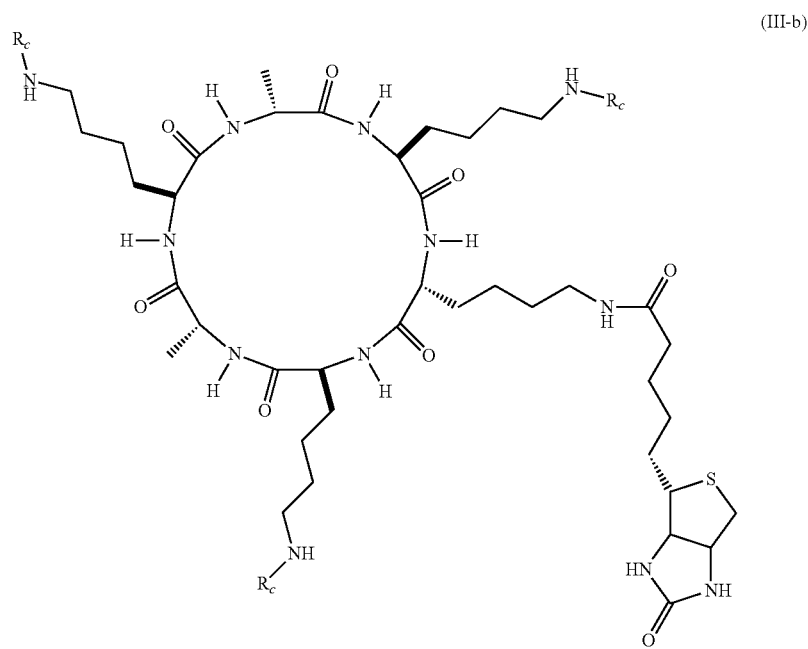
(III-b)

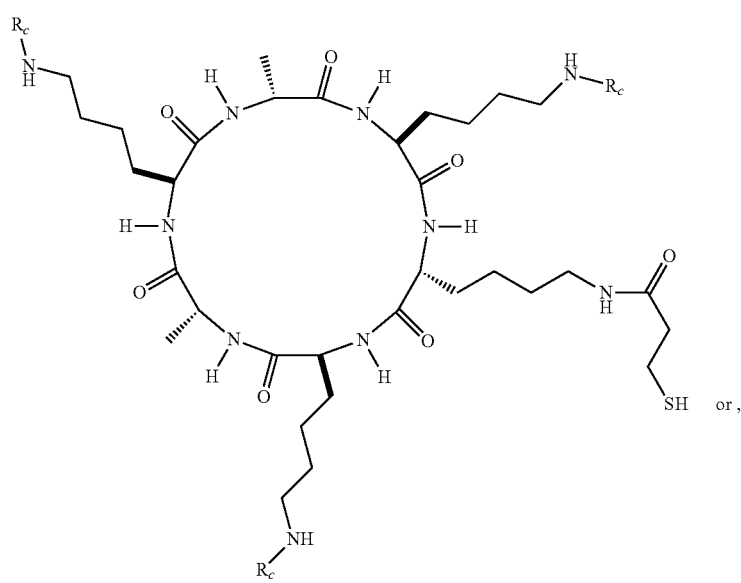
(III-c)
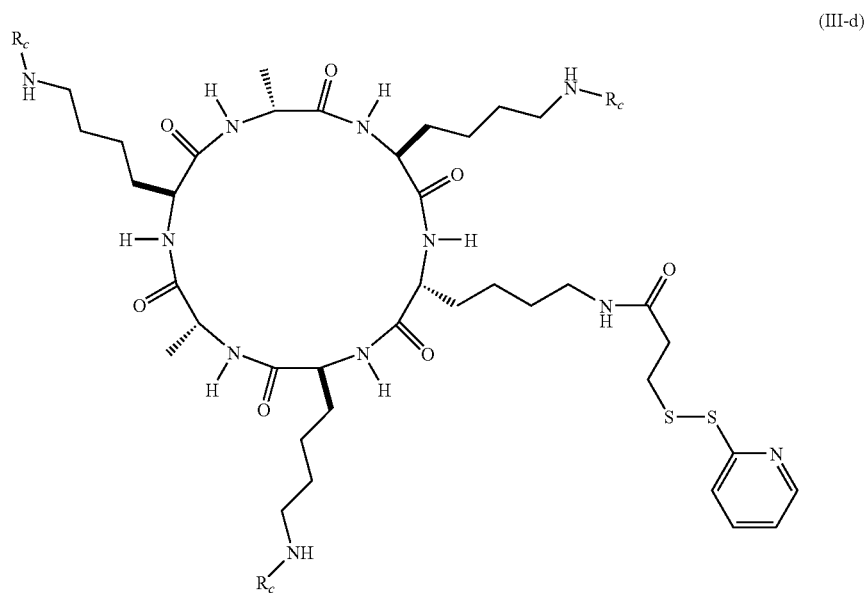
(III-d)
$R_c$ being as previously defined.
8. The compound according to claim 1, wherein $R_c$ is:
H-Lys-(D)Pro-Tyr-Tyr-NH—(CH$_2$)$_5$—CO—,
Ahx-(D) Pro-Tyr-Tyr-NH—(CH$_2$)$_5$—CO—, or
H-Lys-ψ(CH$_2$N)-(D)Pro-Tyr-Tyr-NH—(CH$_2$)$_5$—CO—,
-ψ(CH$_2$N)— corresponding to a pseudopeptide bond of methylene-amino type.
9. The compound according to claim 1, corresponding to one of the following formulae:

121  122
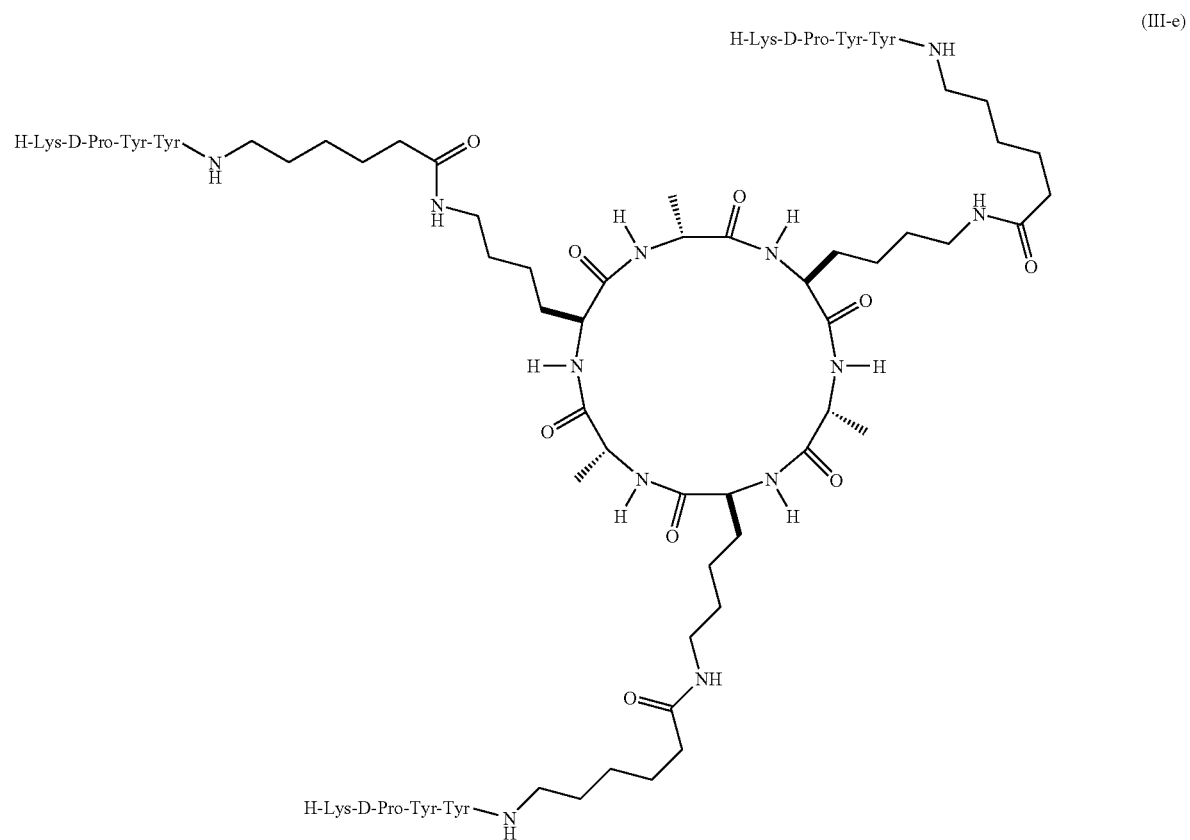
(III-e)
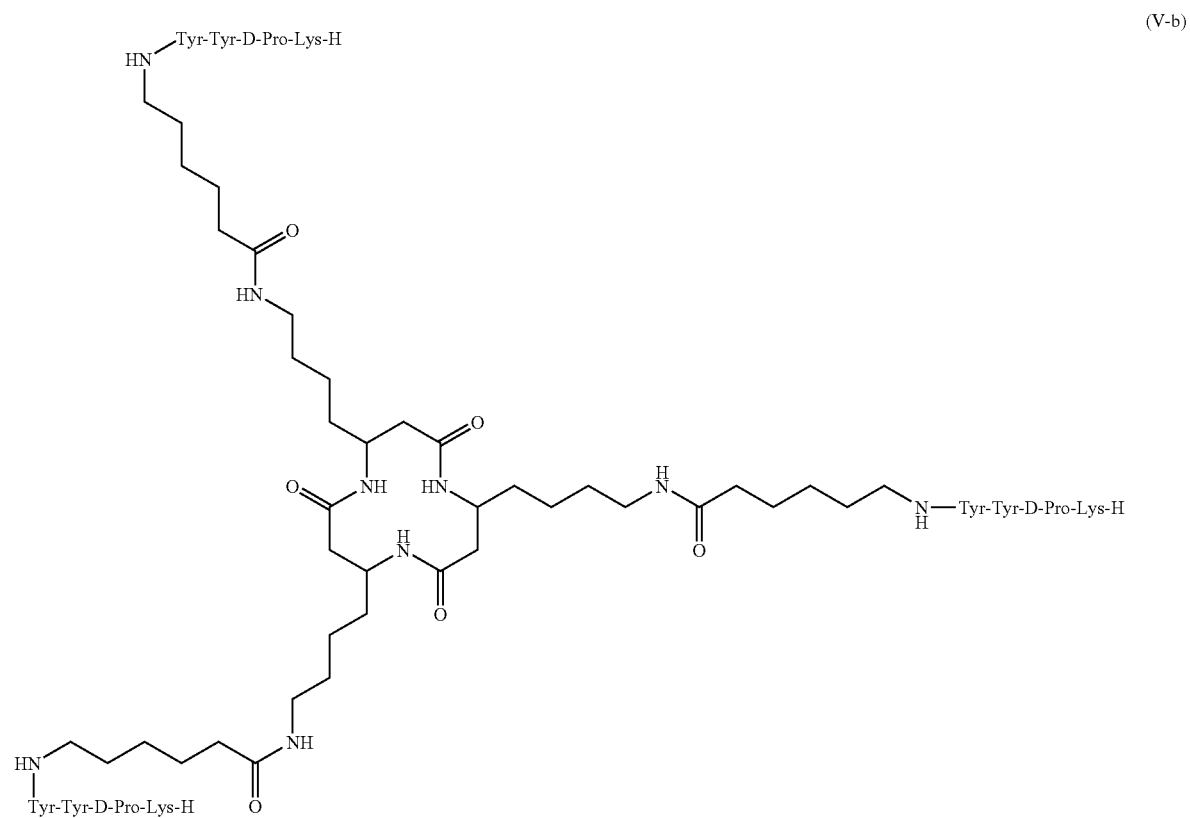
(V-b)

-continued
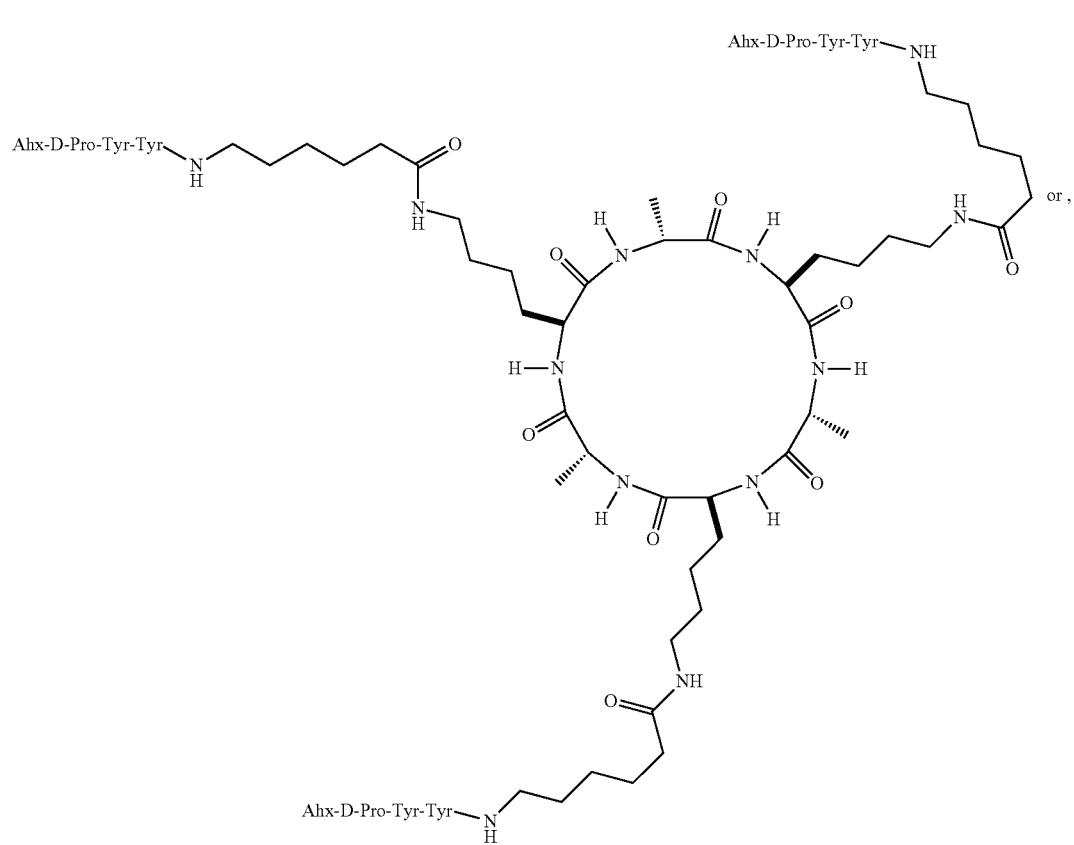
(III-f)
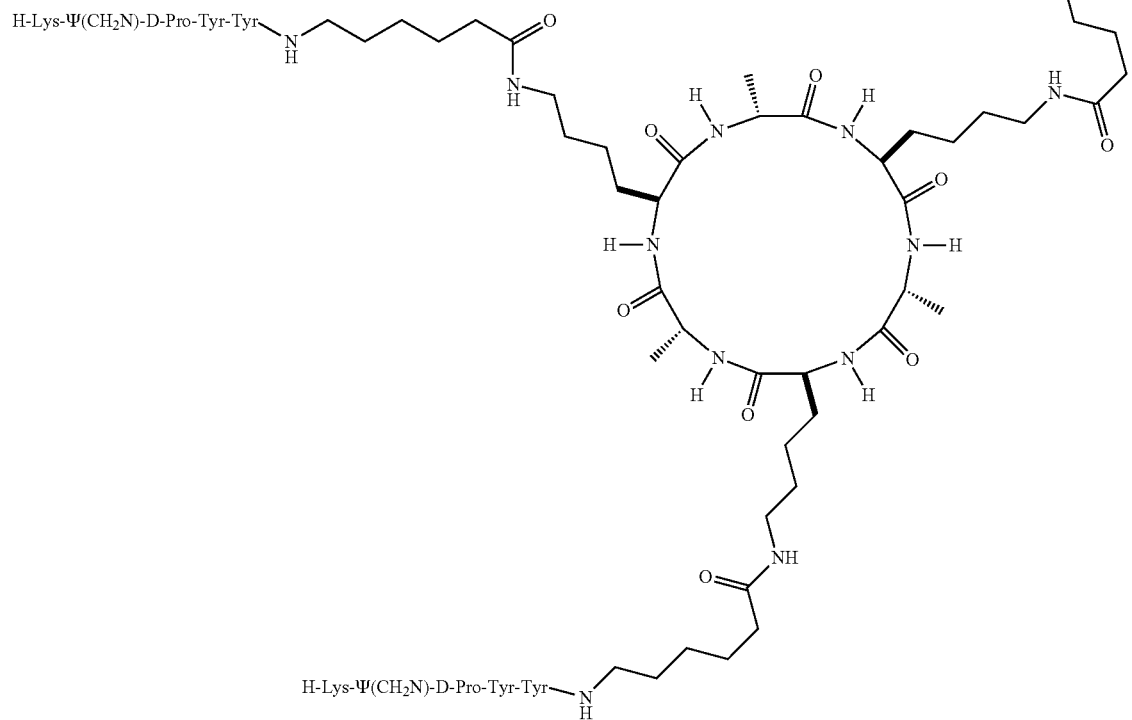
(III-i)

10. The compound according to claim 1, corresponding to one of the following formulae:
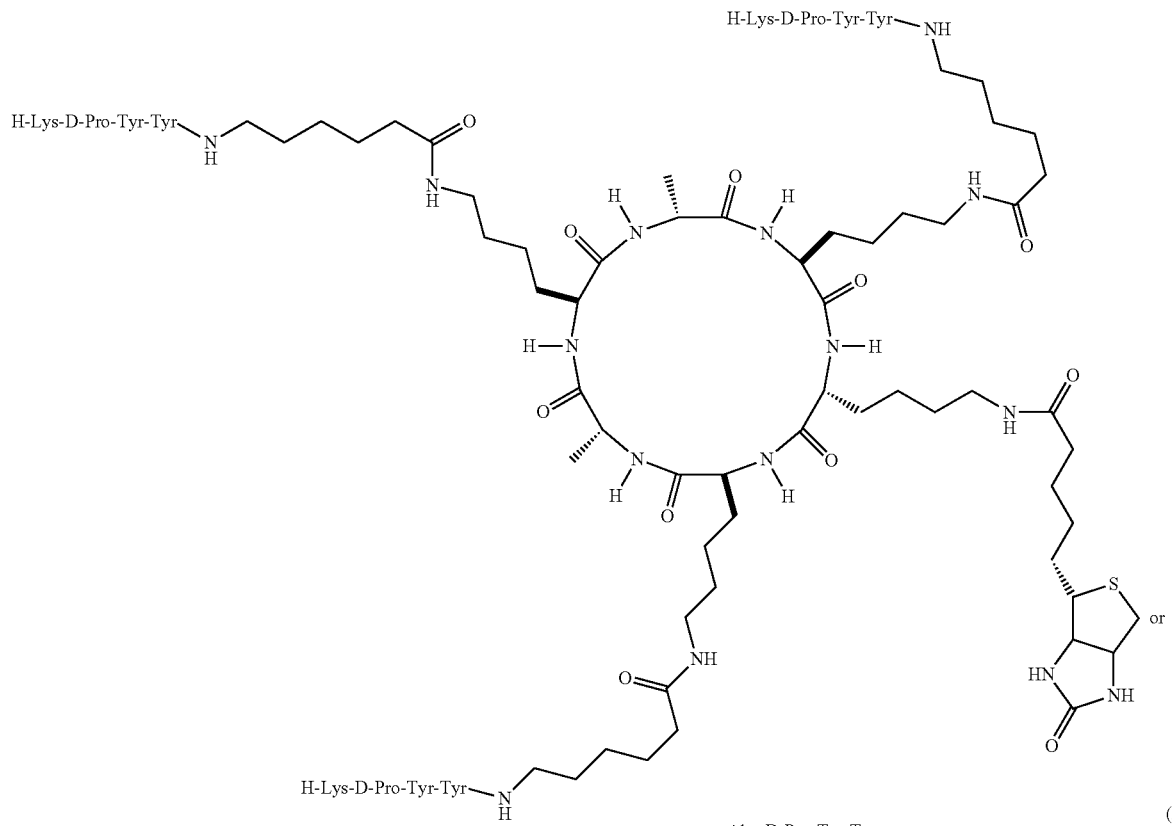
(III-g)
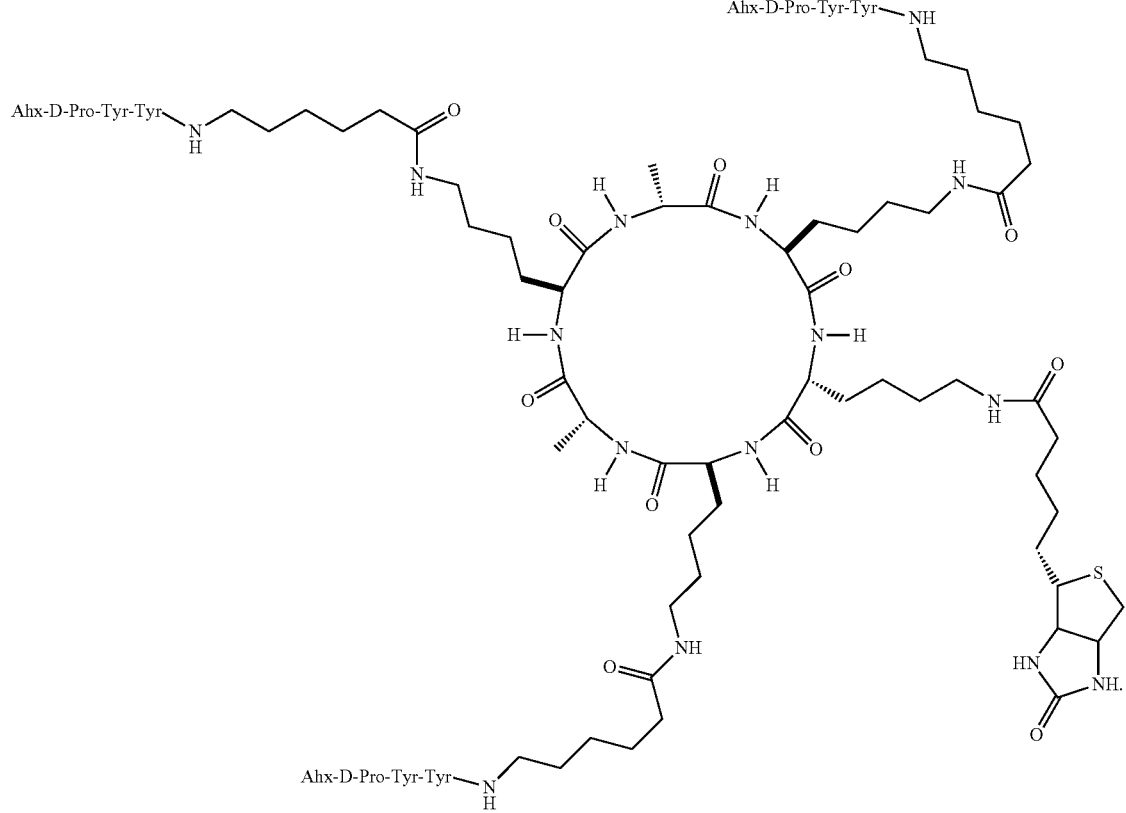
(III-h)

11. A pharmaceutical composition comprising, as active ingredient, a compound according to claim 1, in combination with a pharmaceutically acceptable vector.

12. A method for purifying CD40, comprising providing a support material having the compound of claim 1 grafted thereto;

contacting a sample comprising the CD40 receptor with said support material and allowing the CD40 receptor to bind to the compound grafted thereto; and collecting the CD40 receptor bound to the support.

13. A process for preparing the compound according to claim 1, comprising:

synthesizing a linear precursor of Y on a solid support by peptide synthesis of successive cycles of coupling between N-protected amino acid residues, wherein three amino acid residues carry the $R_a$ group and an amine function protected by a protective group cyclizing the synthesized linear precursor of Y, cleaving said protective groups, in order to release said protected amine functions, coupling the released amine functions with a peptide having the amino acid residues corresponding to the $R_c$ group as defined in claim 1, and cleaving the compound from the solid support.

* * * * *

UNITED STATES PATENT AND TRADEMARK OFFICE
CERTIFICATE OF CORRECTION

PATENT NO. : 8,357,654 B2  Page 1 of 1
APPLICATION NO. : 11/721910
DATED : January 22, 2013
INVENTOR(S) : Guichard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1529 days.

Signed and Sealed this
First Day of September, 2015

Michelle K. Lee
*Director of the United States Patent and Trademark Office*